US012662903B1

(12) United States Patent
Fowler

(10) Patent No.: US 12,662,903 B1
(45) Date of Patent: Jun. 23, 2026

(54) ASSESSING AND REMEDIATING WELL CLOGGING FROM PRECIPITATE, SYSTEMS, APPARATUSES, AND METHODS

(71) Applicant: SEVEE & MAHER ENGINEERS, INC., Cumberland, ME (US)

(72) Inventor: Bruce Austin Fowler, Portland, ME (US)

(73) Assignee: SEVEE & MAHER ENGINEERS, INC., Cumberland, ME (US)

( * ) Notice: Subject to any disclaimer, the term of this patent is extended or adjusted under 35 U.S.C. 154(b) by 0 days.

(21) Appl. No.: 18/612,891

(22) Filed: Mar. 21, 2024

Related U.S. Application Data

(60) Provisional application No. 63/537,495, filed on Sep. 9, 2023, provisional application No. 63/454,031, filed on Mar. 22, 2023.

(51) Int. Cl.
| | |
|---|---|
| *E21B 37/06* | (2006.01) |
| *E03B 3/15* | (2006.01) |
| *E21B 37/08* | (2006.01) |
| *E21B 49/08* | (2006.01) |
| *F04B 47/00* | (2006.01) |
| *G01N 33/18* | (2006.01) |

(52) U.S. Cl.
CPC .......... *E21B 37/06* (2013.01); *E21B 49/0875* (2020.05); *F04B 47/00* (2013.01); *E03B 3/15* (2013.01); *E21B 37/08* (2013.01); *G01N 33/18* (2013.01)

(58) Field of Classification Search
CPC ...... E21B 47/008; E21B 49/0875; E03B 3/16; G01N 3/16
See application file for complete search history.

(56) References Cited

U.S. PATENT DOCUMENTS

| | | | | |
|---|---|---|---|---|
| 1,280,345 A | * | 10/1918 | Wig | E02D 15/06 |
| | | | | 405/223 |
| 3,877,301 A | | 4/1975 | Jensen, Jr. | |
| 4,752,740 A | * | 6/1988 | Steininger | G01N 27/4168 |
| | | | | 324/438 |

(Continued)

FOREIGN PATENT DOCUMENTS

CN          115775438 A          3/2023

OTHER PUBLICATIONS

William C. Walton, Groundwater Resource Evaluation, 1970, pp. 216-219, McGraw Hill, Inc., USA.

(Continued)

*Primary Examiner* — Cathleen R Hutchins
(74) *Attorney, Agent, or Firm* — PELOQUIN, PLLC; Mark S. Peloquin, Esq.

(57)          ABSTRACT

Methods and systems are disclosed to assess clogging associated with a first well. The first well has a well screen or an open borehole in bedrock. A water sample is received from the first well during an ON state. Water is pumped from the first well during the ON state. A first oxidation reduction potential measurement and a first pH measurement are made on the water sample. First clogging specific information is determined for a first mineral or metal utilizing the first oxidation reduction potential measurement, the first pH measurement, and an Eh vs pH phase diagram for the first mineral or metal.

63 Claims, 59 Drawing Sheets

(56) References Cited

U.S. PATENT DOCUMENTS

| | | | | |
|---|---|---|---|---|
| 5,422,014 A | * | 6/1995 | Allen | C02F 1/008 |
| | | | | 210/743 |
| 5,795,996 A | * | 8/1998 | Chang | G01N 33/18 |
| | | | | 422/62 |
| 5,847,972 A | | 12/1998 | Eick | |
| 6,740,231 B1 | * | 5/2004 | Bauman | C02F 5/025 |
| | | | | 210/167.3 |
| 7,457,785 B1 | | 11/2008 | Greitzer | |
| 8,244,499 B2 | | 8/2012 | Lambie | |
| 10,030,502 B1 | | 7/2018 | Singer | |
| 10,677,032 B1 | * | 6/2020 | Norton | E21B 34/14 |
| 10,914,160 B2 | | 2/2021 | Duzan | |
| 11,021,937 B1 | | 6/2021 | Fowler | |
| 12,104,362 B1 | | 10/2024 | Fowler | |
| 2004/0030537 A1 | | 2/2004 | Barnard | |
| 2004/0109800 A1 | * | 6/2004 | Pahlman | B01D 53/565 |
| | | | | 422/177 |
| 2004/0133397 A1 | | 7/2004 | Bjornson | |
| 2006/0016763 A1 | * | 1/2006 | Kerfoot | B09C 1/08 |
| | | | | 210/759 |
| 2008/0162385 A1 | | 7/2008 | Madani | |
| 2008/0262736 A1 | * | 10/2008 | Thigpen | E21B 43/128 |
| | | | | 702/9 |
| 2009/0228129 A1 | | 9/2009 | Moyne | |
| 2010/0193183 A1 | | 8/2010 | Lambie | |
| 2011/0024361 A1 | * | 2/2011 | Schwartzel | C02F 1/467 |
| | | | | 204/290.01 |
| 2012/0267318 A1 | | 10/2012 | Hatten | |
| 2014/0342397 A1 | | 11/2014 | Andersen Gad | |
| 2015/0053414 A1 | | 2/2015 | Reid | |
| 2016/0237773 A1 | | 8/2016 | Dalton | |
| 2017/0241263 A1 | | 8/2017 | Heller | |
| 2017/0370819 A1 | | 12/2017 | Skands | |
| 2018/0155991 A1 | | 6/2018 | Arsalan | |
| 2018/0180657 A1 | | 6/2018 | Park | |
| 2018/0371890 A1 | | 12/2018 | Duzan | |
| 2019/0120087 A1 | | 4/2019 | De Oliveira | |
| 2019/0277686 A1 | | 9/2019 | Dechesne | |
| 2019/0346388 A1 | | 11/2019 | Zhang | |
| 2019/0353630 A1 | * | 11/2019 | Vepsäläinen | E21B 47/06 |
| 2020/0278373 A1 | | 9/2020 | Fukushi | |
| 2020/0340483 A1 | | 10/2020 | Philipp | |
| 2021/0062619 A1 | | 3/2021 | Camacho Cardenas | |
| 2021/0215158 A1 | | 7/2021 | Schou | |
| 2021/0365761 A1 | | 11/2021 | Paul | |
| 2023/0169146 A1 | | 6/2023 | Jones | |

OTHER PUBLICATIONS

George Houben, Water Well Rehabilitation and Reconstruction, pp. 248-254, 261-267, 270-271, McGraw Hill, New York, NY.

Christian Menz, Oxygen Delivering Processes in Groundwater and their Relevance for Iron-Related Well Clogging Processess, 2016, Dissertation, Freie University, Berlin, Germany.

C.G.E.M Van Beek, Cause and Prevention of Clogging of Well Bore Clogging By Particles, Springer-Verlag 2009.

Kalwa et al, Biological and Physical Clogging in Infiltration Wells: Effects of Well Diamter and Gravel Pack Groundwater, vol. 50 No. 6, pp. 819-828 (Year: 2021).

Cui et al, CN 115774538 A, English Machine Translation, pp. 1-11 (Year: 2023).

Song et al, Analysis of Potential Risks Associated With Urban Stormwater Quality, Int. J. Environ. Res. Public Health, 2019 (Year: 2019).

Correia et al, Laboratory Studies on Ochre Formation, Can. Geotech. J., 2022 (Year:2022).

Cabrera et al. Scientific Report of Wadi Wurayah Park, WWF, 2017 (Year: 2017).

W. C. Walton, Groundwater Resource Evaluation, McGraw-Hill Book Company 1970.

W. C. Walton, Illinois State Water Survey Bulletin 49, Plate 1, State of Illinois 1962.

Justin Blum, A Distance-Drawdown Analysis Procedure To Identify The Effects of Bedding-Plane Fractures And Improve The Estimates Of Hydraulic . . . , Minn. Dept.of Health 2019.

* cited by examiner

FIG. 5
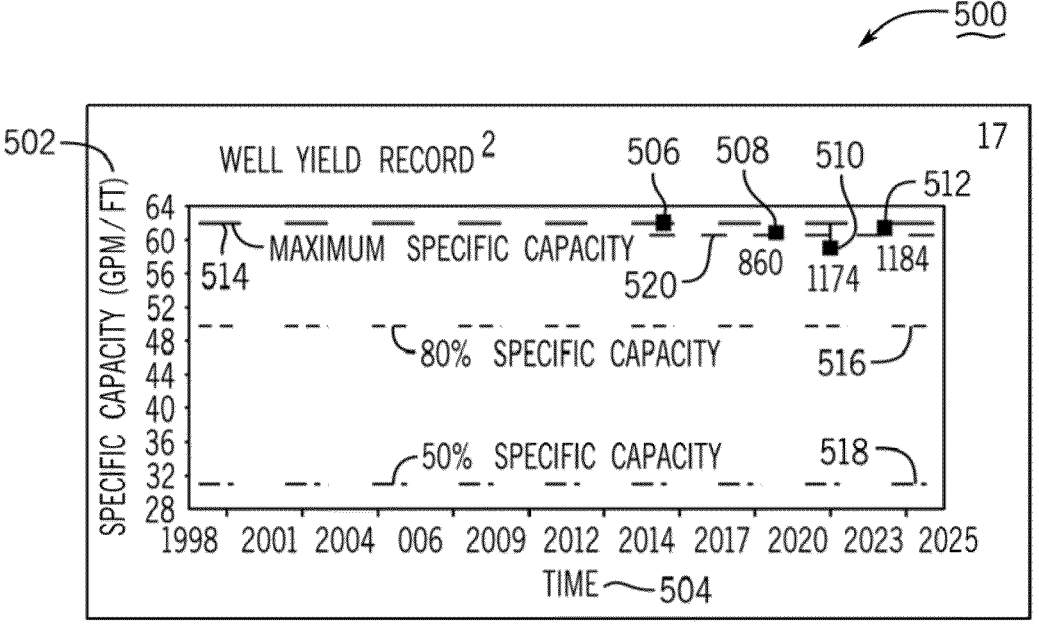
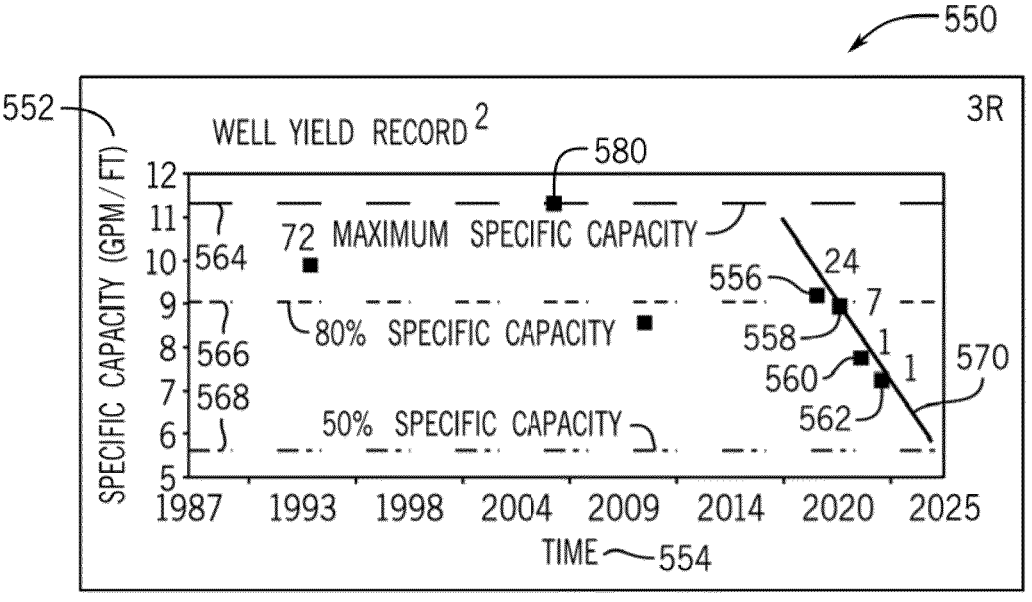

FIG. 9
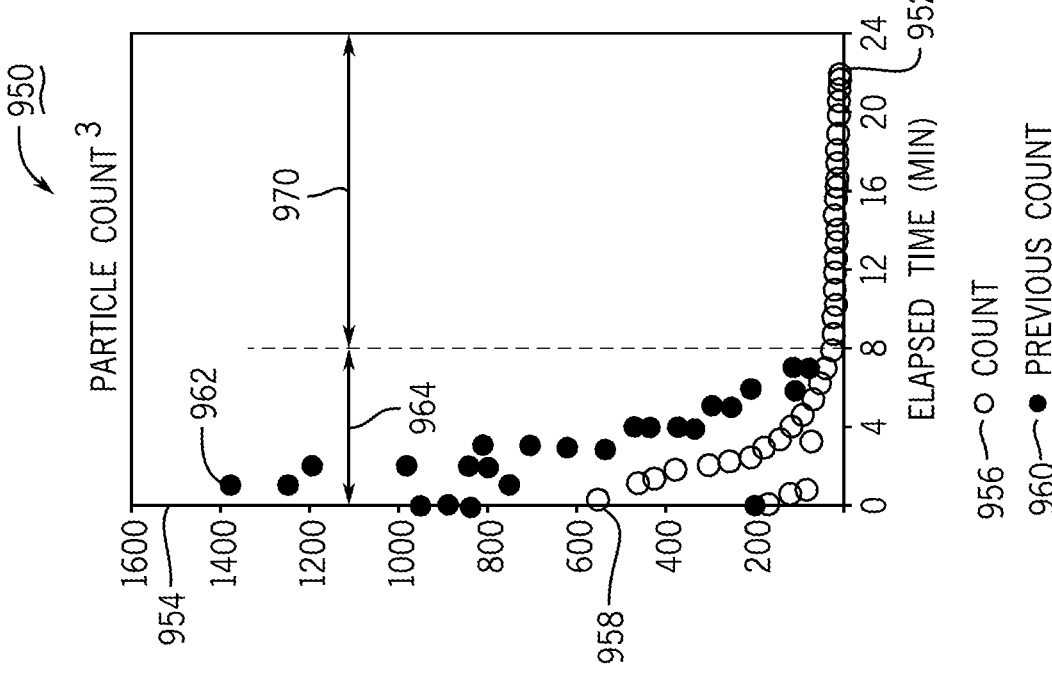
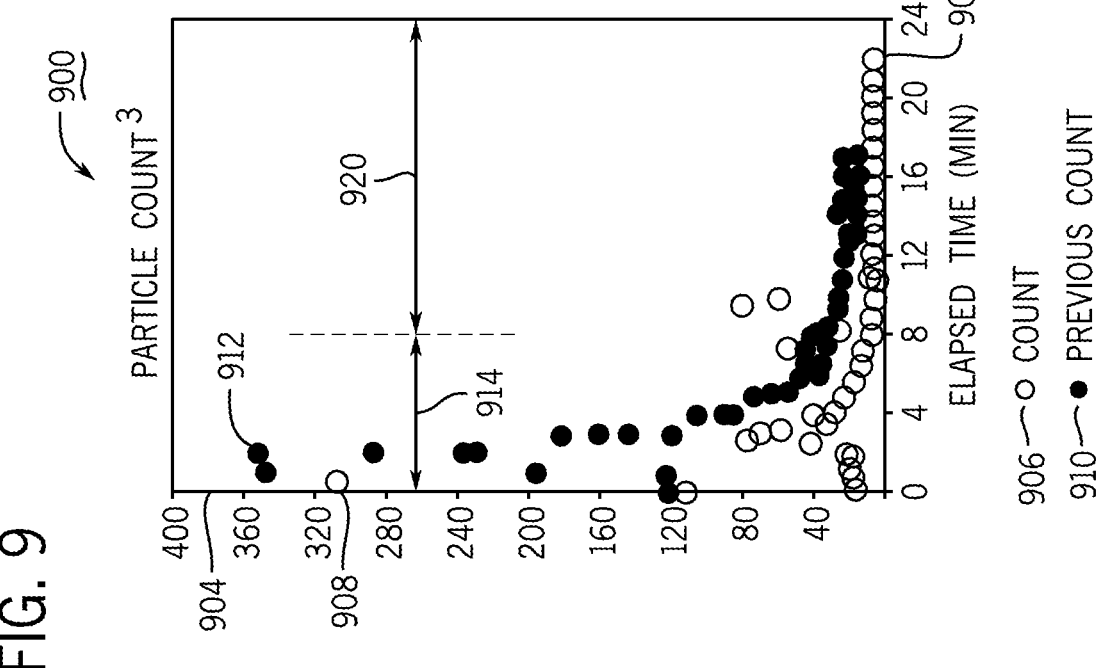

1000

START — 1002

WELL IN QUIESCENT STATE NO PUMPING — 1004

TURN PUMP ON — 1006

COLLECT WATER SAMPLE DURING START UP TRANSIENT OF WELL CAPTURE SURGE IN MOBILE PARTICLES — 1008

DETERMINE CONCENTRATION OF MOBILE PARTICLES IN WATER SAMPLE — 1010

ANALYZE MOBILE PARTICLE DATA FOR CLOGGING SPECIFIED INFORMATION — 1012

END — 1014

FIG. 12
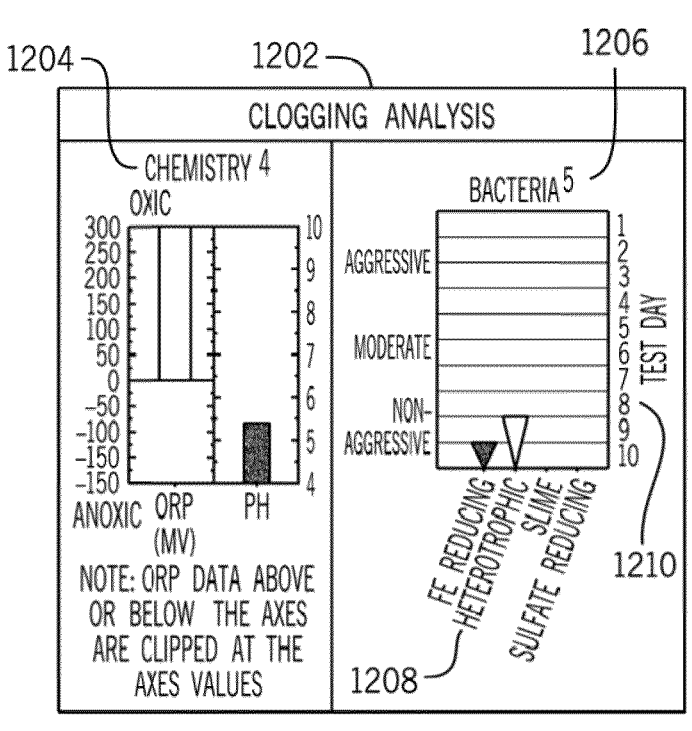
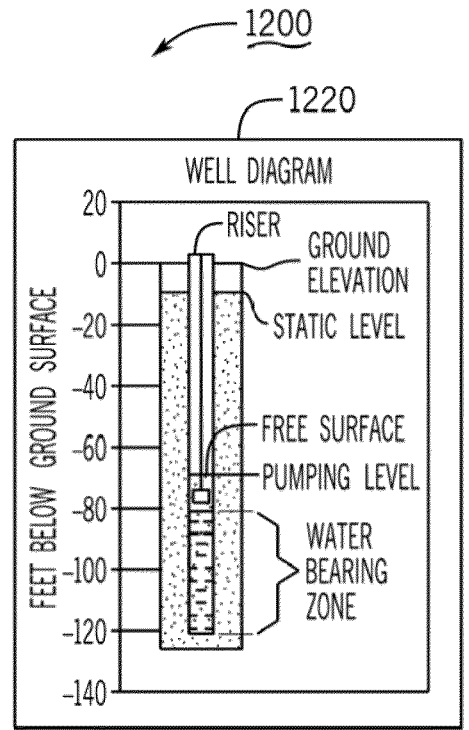
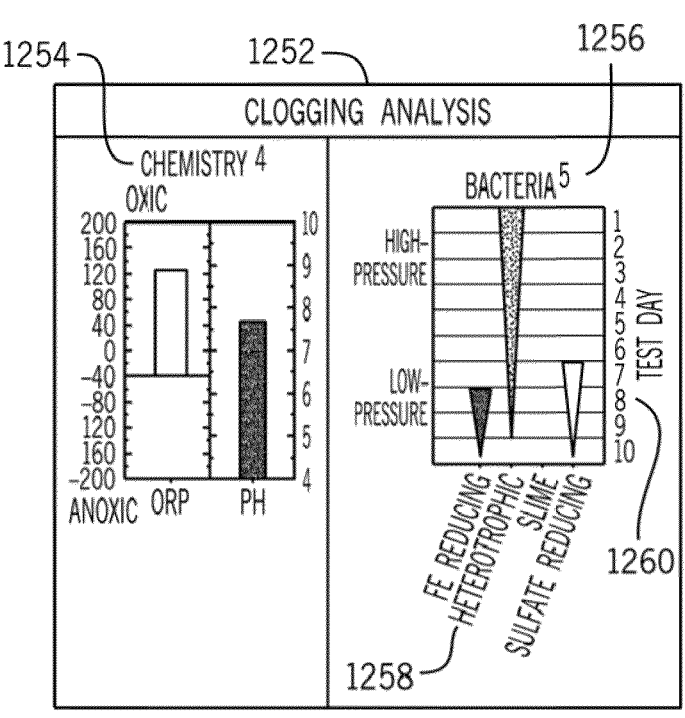
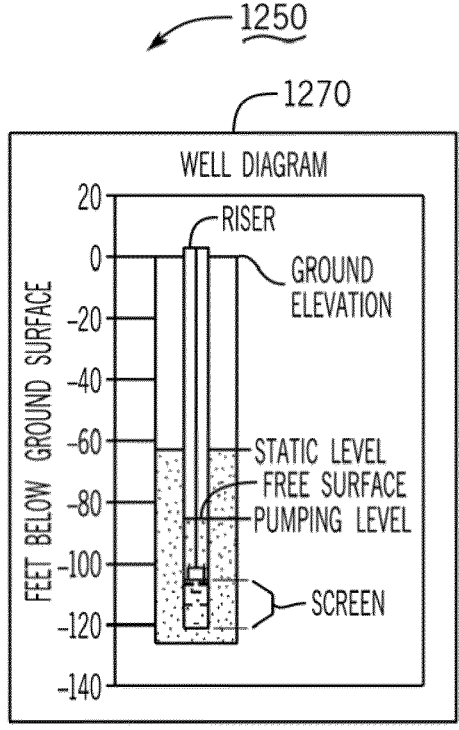

2000

START — 2002

MEASURE SPECIIC CAPACITY OF
WELL FOLLOWING PUMP OFF (FIG.19) — 2004

COMPARE SPECIFIC CAPACITY WITH A
TARGET VALUE FOR SPECIFIC CAPACITY — 2006

REPEAT PROCESS OF FIGURE 19
(STEPS 1906, 1908, 1910, AND 1912
AS NEEDED TO REACH THE TARGET — 2008

END — 2010

FIG. 23A

FIG. 24
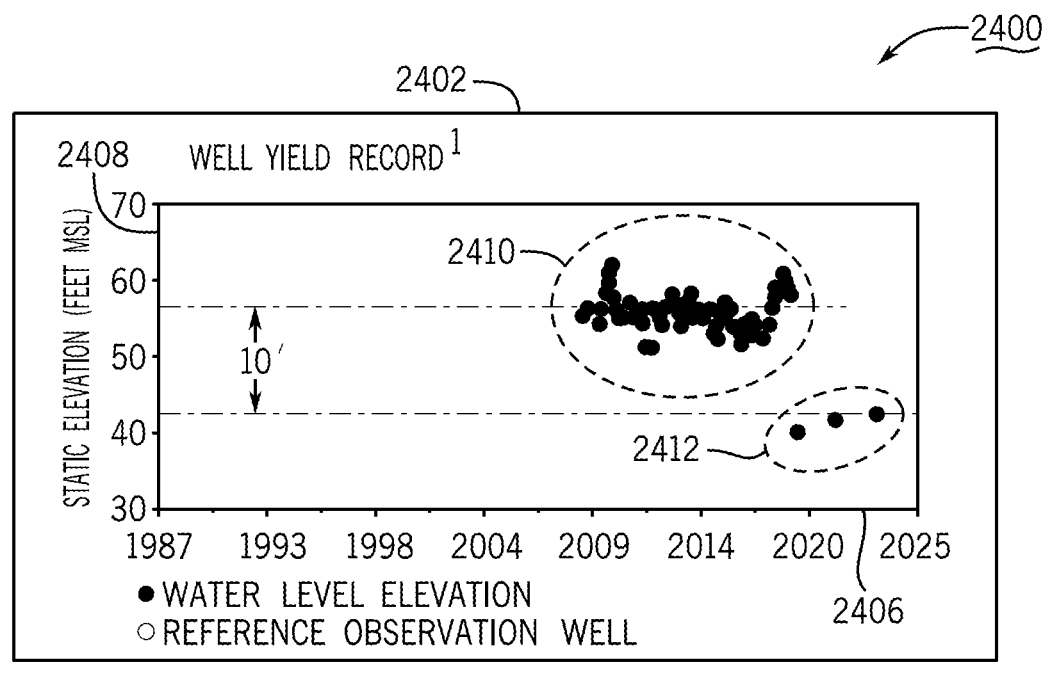
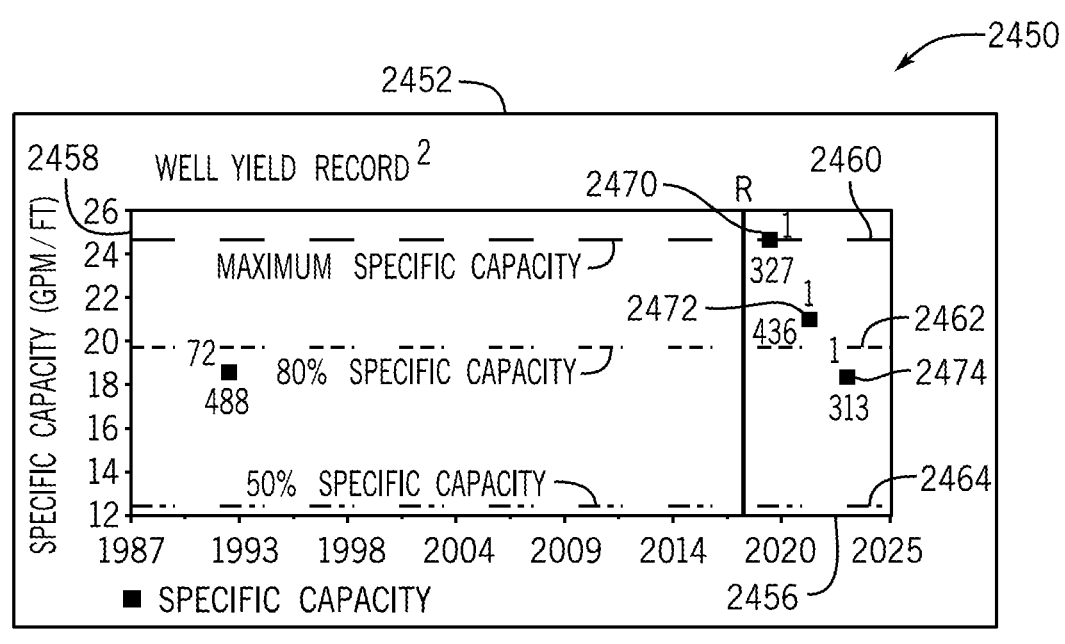

EVALUATE WELL YIELD TO PRODUCE
FINDINGS FOR THE WELL

FIG. 29

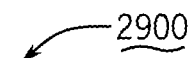

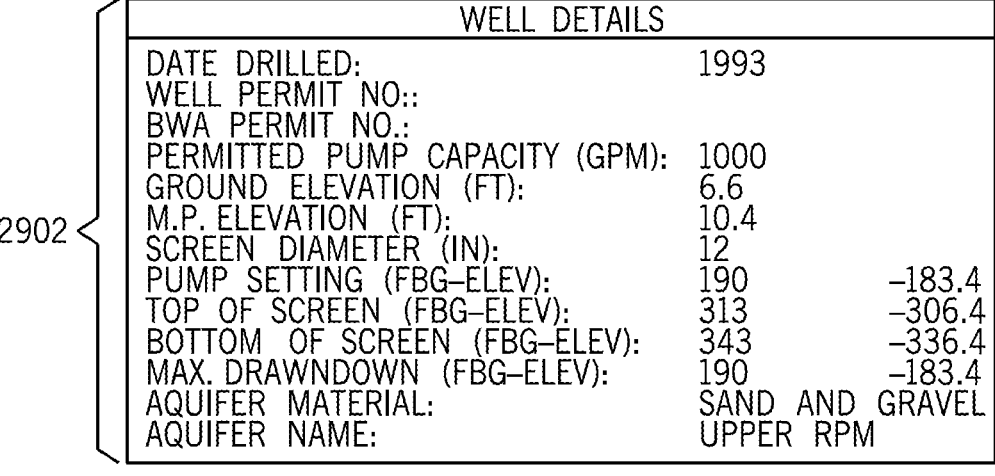

| WELL DETAILS | | |
|---|---|---|
| DATE DRILLED: | 1993 | |
| WELL PERMIT NO:.: | | |
| BWA PERMIT NO.: | | |
| PERMITTED PUMP CAPACITY (GPM): | 1000 | |
| GROUND ELEVATION (FT): | 6.6 | |
| M.P. ELEVATION (FT): | 10.4 | |
| SCREEN DIAMETER (IN): | 12 | |
| PUMP SETTING (FBG-ELEV): | 190 | -183.4 |
| TOP OF SCREEN (FBG-ELEV): | 313 | -306.4 |
| BOTTOM OF SCREEN (FBG-ELEV): | 343 | -336.4 |
| MAX. DRAWDOWN (FBG-ELEV): | 190 | -183.4 |
| AQUIFER MATERIAL: | SAND AND GRAVEL | |
| AQUIFER NAME: | UPPER RPM | |

2902

| 1-HOUR PUMPING CONDITIONS | 12/06/2022 | |
|---|---|---|
| TEST PUMPING RATE (GPM): | 778 | |
| STATIC LEVEL (FMP-ELEV): | 53.1 | -42.7 |
| PUMPING LEVEL (FMP-ELEV): | 159.5 | -149.1 |

2904

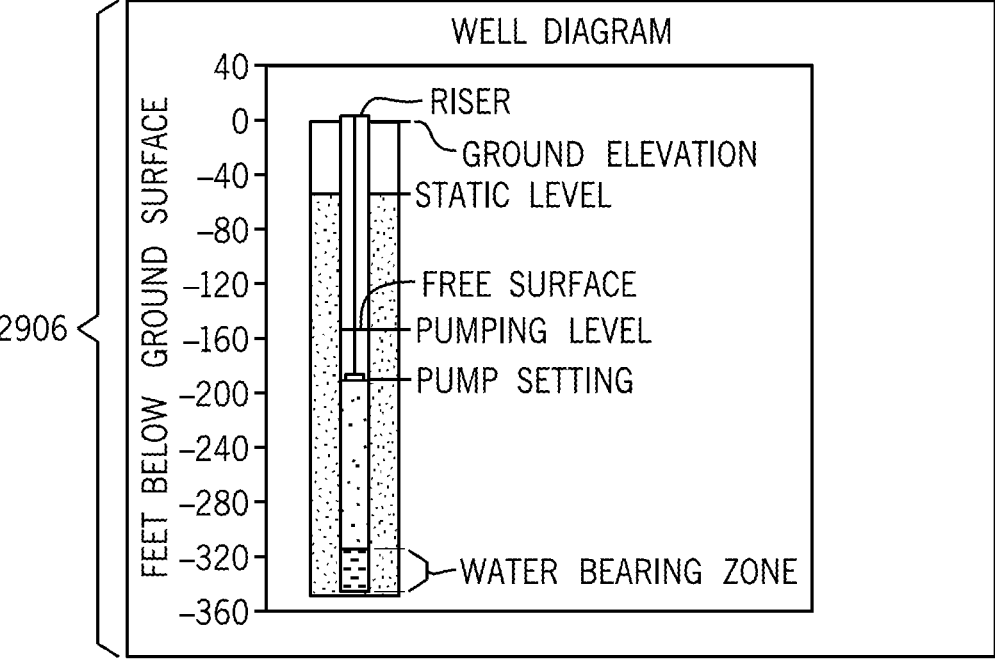

| WELL DIAGRAM |
|---|

2906

| THREE-DAY YIELD EVALUATION6 | |
|---|---|
| PRODUCTION PUMPING (GPM): | 500 |
| PRODUCTION DEFICIENCY (GPM): | -500 |
| EVALUATION PUMPING LEVEL (FBG): | 141.1 |
| SPECIFIC CAPACITY (GPM/FT): | 5.7 |
| SAFETY/INTERFERENCE FACTOR (FT): | 10/0 |
| AVAILABLE DRAWDOWN (FT): | 43 |
| ADDITIONAL YIELD (GPM): | 243 |
| BWA PERMIT RESTRICTIONS: | CRITICAL AREA |

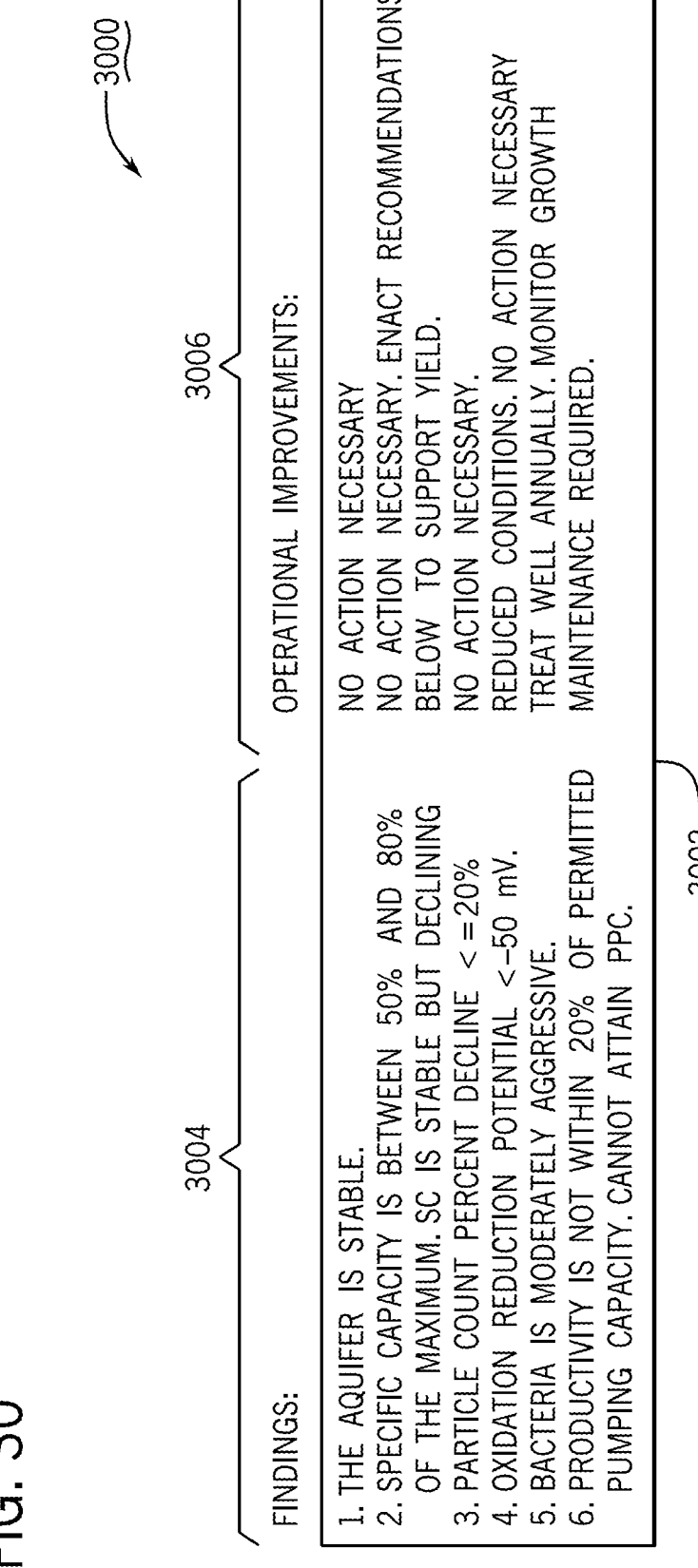

FINDINGS:

1. THE AQUIFER IS STABLE.
2. SPECIFIC CAPACITY IS BETWEEN 50% AND 80% OF THE MAXIMUM. SC IS STABLE BUT DECLINING
3. PARTICLE COUNT PERCENT DECLINE <=20%
4. OXIDATION REDUCTION POTENTIAL <-50 mV.
5. BACTERIA IS MODERATELY AGGRESSIVE.
6. PRODUCTIVITY IS NOT WITHIN 20% OF PERMITTED PUMPING CAPACITY. CANNOT ATTAIN PPC.

OPERATIONAL IMPROVEMENTS:

NO ACTION NECESSARY
NO ACTION NECESSARY. ENACT RECOMMENDATIONS BELOW TO SUPPORT YIELD.
NO ACTION NECESSARY.
REDUCED CONDITIONS. NO ACTION NECESSARY
TREAT WELL ANNUALLY. MONITOR GROWTH
MAINTENANCE REQUIRED.

$$WPM_i = \sum_{j=1}^{N} (CATEGORY_{i,j} * ADJFAC_j) \quad \text{For: } 1 \le i \le M, \, 1 \le j \le N$$

3404

$$NWPM_i = \frac{WPM_i}{WPM_{NORM}}$$

3406

$CATEGORY_{i,j}$ = A VALUE FOR THE $i^{th}$ CATEGORY OF THE $i^{th}$ WELL

3408

$ADJFAC_j$ = ADJUSTMENT FACTOR APPLIED TO THE $j^{th}$ CATEGORY VALUE

3410   $WPM_i$ = WELL PERFORMANCE METRIC OF THE $i^{th}$ WELL

3412   $NWPM_i$ = NORMALIZED $WPM_i$

3414   $WPM_{NORM}$ = MAXIMUM $WPM_i$

3416   $M$ = NUMBER OF WELLS IN GROUP

3418   $N$ = NUMBER OF CATEGORIES IN $WPM_i$

$$WPM_i = \sum_{j=1}^{N} (CATEGORY_{i,j} + OFFSET_j) * ADJFAC_j$$

3504

$OFFSET_j$ = OFFSET ADDED TO THE $j^{th}$ CATEGORY VALUE OR CATEGORY WEIGHT

PRODUCTION DEFICIENCY

WELL NORMALIZED, GROUP DISTRIBUTION WEIGHTED SCORE (ORDERED BY SCORE)

3600

3606

3602

3608

3604

PRODUCTION DEFICIENCY
CLOGGING
REDEVELOPMENT
SC %DECLINE
BIOLOGICAL

WELL 12
WELL 13
WELL 05
WELL 23
WELL 03
WELL 22
WELL 34
WELL 18
WELL 02
WELL 16
WELL 21
WELL 32
WELL 17
WELL 11
WELL 20
WELL 01
WELL 33
WELL 09
WELL 19
WELL 07
WELL 04
WELL 06
WELL 31
WELL 30
WELL 29
WELL 28
WELL 27
WELL 26
WELL 24
WELL 14
WELL 08
WELL 35
WELL 10
WELL 15
WELL 25

WELL NORMALIZED, GROUP DISTRIBUTION WEIGHTED SCORE (ORDERED BY SCORE)

BIOLOGICAL

3900

3902

3904

☒ PRODUCTION DEFICIENCY
☒ CLOGGING
▨ REDEVELOPMENT
☐ SC %DECLINE
■ BIOLOGICAL

—4000

4 CATEGORY ANALYSIS (N=4)

| |
|---|
| WY = PRODUCTION DEFICIENCY |

—4002

| |
|---|
| SC = DECLINE IN SPECIFIC CAPACITY |

—4004

| |
|---|
| CP = CLOGGING POTENTIAL, HAVING COMPONENTS OF: (A) WATER COVER ABOVE WELL SCREEN, (B) AQUIFER STATUS, (C) ORP (D) BACTERIA PRESENCE |

—4006

| |
|---|
| RD = ESTIMATED TIME TO REDEVELOPMENT |

—4008

| |
|---|
| WPM = WY*f1 + SC*f2 + CP*f3 + RD*f4 |

—4010

| |
|---|
| f1, f2, f3, AND f4 |

—4012

Well Normalized, Group Distribution Weighted Score (Ordered by Score)

PRODUCTION DEFICIENCY
CLOGGING
REDEVELOPMENT
SC %DECLINE
BIOLOGICAL

FIG. 42B

4201 — WELL CONSTRUCTION    4250    4242

| WELL NAME | ZONE DIAMETER (IN) | ZONE INTERVAL (FBG) | PERMIT PUMPING CAPACITY (GPM) | ORP (CHEMICAL) | pH (CHEMICAL) | Fe REDUCING (BACTERIAL) | HETEROTROPHIC (BACTERIAL) | SLIME (BACTERIAL) | SULFATE REDUCING (BACTERIAL) | PARTICLE COUNT DECLINE (%)[1] | HEIGHT OF PUMPING LEVEL OVER SCREEN (FT) | CLOGGING SCORE | AQUIFER STABILITY | PRODUCTION RATE (GPM) | PUMPING RATE CHANGE FROM PERMITTED PUMPING CAPACITY | ADDITIONAL YIELD IF ANY (GPM) | SC DECLINE FROM MAX (%)[1,3] | SC RATE OF CHANGE (gpm/yr*ft)[1,2] | NORMALIZED SCORE |
|---|---|---|---|---|---|---|---|---|---|---|---|---|---|---|---|---|---|---|---|
| WELL 31 | 10 | 524 – 642 | 1010 | 49.1 | 7.12 | 7 | 10 | 9 | 11 | | 349.7 | 6 | | 1078 | 68 | 384 | 6.5 | -0.1 | 0 |
| WELL 33 | 8 | 746 – 797 | 700 | -197.5 | 7.7 | 4 | 2 | 9 | 9 | | 615.0 | 1 | | 690 | -10 | 214 | 0 | 0.0 | 1 |
| AQUIFER NAME: KIRKWOOD-COHANSEY | | | | | | | | | | | | | | | | | | | |
| WELL 01 | 12 | 172 – 208 | 750 | 426.9 | 4.97 | 8 | 2 | 2 | 11 | | 108.4 | 157 | STABLE | 688 | -62 | 0 | 34.8 | -0.1 | 35 |
| WELL 07 | 12 | 181 – 232 | 710 | 365.9 | 5.37 | 7 | 9 | 6 | 11 | | 11.9 | 17 | STABLE | 803 | 93 | 0 | 83.2 | -1.9 | 3 |
| WELL 08 | 12 | 92 – 127 | 700 | 576 | 5.17 | 4 | 3 | 4 | 11 | | 65.3 | 12 | STABLE | 740 | 40 | 277 | 7.6 | 0.0 | 1 |
| WELL 10 | 10 | 80 – 99 | 400 | 382.4 | 5.34 | 11 | 5 | 8 | 11 | | 4.6 | 67 | STABLE | 400 | 0 | 0 | 36.5 | 0.0 | 10 |
| WELL 11 | 10 | 335 – 425 | 600 | -43.2 | 5.95 | 3 | 2 | 8 | 11 | | 222.7 | 7 | STABLE | 530 | -70 | 434 | 0 | 0.0 | 12 |
| WELL 14 | 10 | 81 – 121 | 1000 | 393.9 | 5.41 | 10 | 9 | 22 | 9 | | 3.4 | 22 | STABLE | 1005 | 5 | 2120 | 1.4 | 0.0 | 2 |
| WELL 15 | 12 | 220 – 260 | 700 | -174.8 | 7.74 | 3 | 2 | 6 | 11 | | 148.7 | 7 | STABLE | 782 | 82 | 900 | 0 | 0.0 | 1 |
| WELL 17 | 12 | 96 – 146 | 750 | 225.8 | 4.65 | 2 | 3 | 7 | 11 | | 50.8 | 12 | STABLE | 638 | -112 | 900 | 20 | 0.0 | 20 |
| WELL 20 | 12 | 130 – 180 | 750 | 380.1 | 5.18 | 7 | 10 | 4 | 11 | | 9.5 | 12 | STABLE | 681 | -69 | 153 | 14.6 | 0.0 | 13 |
| WELL 21 | 12 | 134 – 185 | 750 | 338.5 | 5.1 | 9 | 10 | 10 | 11 | | 82.8 | 12 | STABLE | 611 | -139 | 497 | 6.9 | 0.0 | 24 |
| WELL 22 | 12 | 130 – 180 | 750 | 361.5 | 5.26 | 8 | 5 | 8 | 11 | | 82.2 | 12 | STABLE | 560 | -190 | 331 | 20.2 | 0.0 | 33 |
| WELL 24 | 16 | 100 – 130 | 1000 | 409.5 | 5.43 | 5 | 3 | 8 | 11 | | 57.5 | 12 | STABLE | 1033 | 33 | 1397 | 17.8 | 0.0 | 1 |
| WELL 26 | 8 | 145 – 205 | 500 | 161.5 | 8.14 | 7 | 10 | 11 | 11 | | 53.3 | 17 | STABLE | 699 | 199 | 802 | 3.2 | 0.0 | 2 |
| WELL 30 | 18 | 78 – 124 | 1000 | 361.1 | 5.38 | 5 | 5 | 7 | 11 | | 4.3 | 22 | STABLE | 1001 | 1 | 0 | 3.6 | 0.0 | 3 |
| WELL 32 | 18 | 189 – 229 | 1400 | 423.6 | 5.56 | 9 | 3 | 6 | 11 | | 114.7 | 57 | STABLE | 1190 | -210 | 322 | 66.5 | -3.3 | 44 |
| WELL 34 | 10 | 132 – 162 | 600 | 371.7 | 5.61 | 6 | 9 | 9 | 11 | | 74.9 | 12 | STABLE | 472 | -128 | 1911 | 16.8 | 0.0 | 22 |
| WELL 35 | 12 | 170 – 200 | 500 | 390.3 | 5.24 | 5 | 7 | 7 | 11 | | 91.9 | 12 | STABLE | 553 | 53 | 570 | 17.7 | 0.0 | 1 |

Column group headers: WELL CONSTRUCTION | CLOGGING ASSESSMENT (CHEMICAL, BACTERIAL) | CURRENT YIELD CONDITIONS NOTES: 1 PARTICLE COUNT AND SPECIFIC CAPACITY DECLINES REQUIRE TWO YIELD EVALUATIONS TO CALCULATE
2 RATE OF CHANGE IS CALCULATED FROM TWO MOST RECENT SPECIFIC CAPACITIES RECORDED.
3 THE MAX SPECIFIC CAPACITY IS FROM ALL HISTORICAL RECORDS.

FIG. 43A

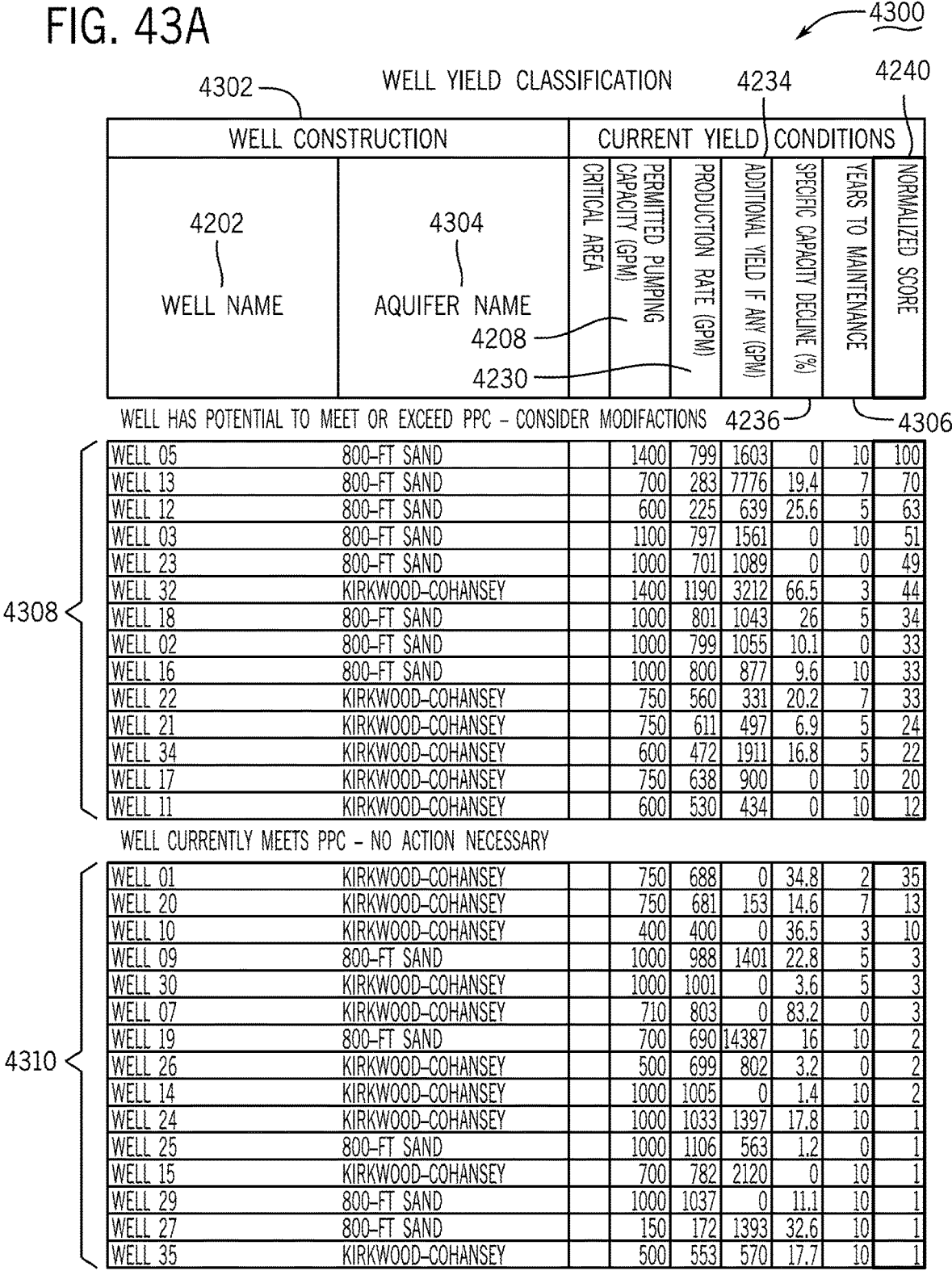

| | WELL CONSTRUCTION | | CURRENT YIELD | | | CONDITIONS | | |
|---|---|---|---|---|---|---|---|---|
| | 4202<br>WELL NAME | 4304<br>AQUIFER NAME | CRITICAL AREA | PERMITTED PUMPING CAPACITY (GPM) | PRODUCTION RATE (GPM) | ADDITIONAL YIELD IF ANY (GPM) | SPECIFIC CAPACITY DECLINE (%) | YEARS TO MAINTENANCE | NORMALIZED SCORE |
| WELL HAS POTENTIAL TO MEET OR EXCEED PPC – CONSIDER MODIFACTIONS | | | | | | | | | |
| | WELL 05 | 800-FT SAND | | 1400 | 799 | 1603 | 0 | 10 | 100 |
| | WELL 13 | 800-FT SAND | | 700 | 283 | 7776 | 19.4 | 7 | 70 |
| | WELL 12 | 800-FT SAND | | 600 | 225 | 639 | 25.6 | 5 | 63 |
| | WELL 03 | 800-FT SAND | | 1100 | 797 | 1561 | 0 | 10 | 51 |
| | WELL 23 | 800-FT SAND | | 1000 | 701 | 1089 | 0 | 0 | 49 |
| | WELL 32 | KIRKWOOD-COHANSEY | | 1400 | 1190 | 3212 | 66.5 | 3 | 44 |
| | WELL 18 | 800-FT SAND | | 1000 | 801 | 1043 | 26 | 5 | 34 |
| | WELL 02 | 800-FT SAND | | 1000 | 799 | 1055 | 10.1 | 0 | 33 |
| | WELL 16 | 800-FT SAND | | 1000 | 800 | 877 | 9.6 | 10 | 33 |
| | WELL 22 | KIRKWOOD-COHANSEY | | 750 | 560 | 331 | 20.2 | 7 | 33 |
| | WELL 21 | KIRKWOOD-COHANSEY | | 750 | 611 | 497 | 6.9 | 5 | 24 |
| | WELL 34 | KIRKWOOD-COHANSEY | | 600 | 472 | 1911 | 16.8 | 5 | 22 |
| | WELL 17 | KIRKWOOD-COHANSEY | | 750 | 638 | 900 | 0 | 10 | 20 |
| | WELL 11 | KIRKWOOD-COHANSEY | | 600 | 530 | 434 | 0 | 10 | 12 |
| WELL CURRENTLY MEETS PPC – NO ACTION NECESSARY | | | | | | | | | |
| | WELL 01 | KIRKWOOD-COHANSEY | | 750 | 688 | 0 | 34.8 | 2 | 35 |
| | WELL 20 | KIRKWOOD-COHANSEY | | 750 | 681 | 153 | 14.6 | 7 | 13 |
| | WELL 10 | KIRKWOOD-COHANSEY | | 400 | 400 | 0 | 36.5 | 3 | 10 |
| | WELL 09 | 800-FT SAND | | 1000 | 988 | 1401 | 22.8 | 5 | 3 |
| | WELL 30 | KIRKWOOD-COHANSEY | | 1000 | 1001 | 0 | 3.6 | 5 | 3 |
| | WELL 07 | KIRKWOOD-COHANSEY | | 710 | 803 | 0 | 83.2 | 0 | 3 |
| | WELL 19 | 800-FT SAND | | 700 | 690 | 14387 | 16 | 10 | 2 |
| | WELL 26 | KIRKWOOD-COHANSEY | | 500 | 699 | 802 | 3.2 | 0 | 2 |
| | WELL 14 | KIRKWOOD-COHANSEY | | 1000 | 1005 | 0 | 1.4 | 10 | 2 |
| | WELL 24 | KIRKWOOD-COHANSEY | | 1000 | 1033 | 1397 | 17.8 | 10 | 1 |
| | WELL 25 | 800-FT SAND | | 1000 | 1106 | 563 | 1.2 | 0 | 1 |
| | WELL 15 | KIRKWOOD-COHANSEY | | 700 | 782 | 2120 | 0 | 10 | 1 |
| | WELL 29 | 800-FT SAND | | 1000 | 1037 | 0 | 11.1 | 10 | 1 |
| | WELL 27 | 800-FT SAND | | 150 | 172 | 1393 | 32.6 | 10 | 1 |
| | WELL 35 | KIRKWOOD-COHANSEY | | 500 | 553 | 570 | 17.7 | 10 | 1 |

4300

4302

WELL YIELD CLASSIFICATION

4234

4240

4208

4230

4236

4306

4308

4310

| WELL CONSTRUCTION | | CURRENT YIELD CONDITIONS | | | | | |
| WELL NAME | AQUIFER NAME | CRITICAL AREA | PUMPING CAPACITY (GPM) | PRODUCTION RATE (GPM) | ADDITIONAL YIELD IF ANY (GPM) | SPECIFIC CAPACITY DECLINE (%) | YEARS TO MAINTENANCE | NORMALIZED SCORE |
|---|---|---|---|---|---|---|---|---|
| WELL 04 | 800-FT SAND | | 700 | 749 | 684 | 20 | 7 | 1 |
| WELL 33 | 800-FT SAND | | 700 | 690 | 214 | 0 | 0 | 1 |
| WELL 08 | KIRKWOOD-COHANSEY | | 700 | 740 | 2477 | 7.6 | 10 | 1 |
| WELL 28 | 800-FT SAND | | 150 | 173 | 892 | 18.7 | 10 | 0 |
| WELL 06 | 800-FT SAND | | 500 | 597 | 5049 | 12.2 | 10 | 0 |
| WELL 31 | 800-FT SAND | | 1010 | 1078 | 384 | 6.5 | 5 | 0 |

FIG. 48

ASSESSING AND REMEDIATING WELL CLOGGING FROM PRECIPITATE, SYSTEMS, APPARATUSES, AND METHODS

RELATED PATENT APPLICATIONS

This patent application claims priority from United States Provisional Patent Application titled: "WELL CLOGGING AND REMEDIATION, ANALYSIS, SYSTEMS, AND METHODS," filed on Mar. 22, 2023, Ser. No. 63/454,031. U.S. Provisional Patent Application Ser. No. 63/454,031 is hereby incorporated by reference. This patent application claims priority from United States Provisional Patent Application titled: "WELL YIELD EVALUATION AND OPTIMIZATION, ANALYSIS, SYSTEMS, AND METHODS," filed on Sep. 9, 2023, Ser. No. 63/537,495. U.S. Provisional Patent Application Ser. No. 63/537,495 is hereby incorporated by reference. This application is related to United States Non-Provisional Application having Ser. No. 18/611,715 filed on Mar. 21, 2024, titled: "SPECIFIC CAPACITY MEASUREMENT AND ESTIMATION IN A WELL, SYSTEMS, APPARATUSES, AND METHODS," which is now U.S. Pat. No. 12,270,962 B1. This application is related to United States Non-Provisional Application having Ser. No. 18/611,712 filed on Mar. 21, 2024, titled: "ASSESSING AND REMEDIATING WELL CLOGGING FROM MOBILE PARTICLES, SYSTEMS, APPARATUSES, AND METHODS," which is now U.S. Pat. No. 12,287,271 B1. This application is related to United States Non-Provisional Application having Ser. No. U.S. 18/611,704 filed on Mar. 21, 2024, titled: "ASSESSING AND REMEDIATING WELL CLOGGING FROM BACTERIA, SYSTEMS, APPARATUSES, AND METHODS," which is now U.S. Pat. No. 12,104,362 B1. This application is related to United States Non-Provisional Application having Ser. No. U.S. 18/612,915 filed on Mar. 21, 2024, titled "WELL YIELD EVALUATION AND OPTIMIZATION, SYSTEMS, APPARATUSES, AND METHODS." This application is related to United States Non-Provisional Application having Ser. No. U.S. 18/612,950 filed on Mar. 21, 2024, titled "WELL PERFORMANCE METRICS, SYSTEMS, APPARATUSES, AND METHODS."

BACKGROUND OF THE INVENTION

1. Field of Invention

The invention relates generally to well yield evaluation and optimization that employs field testing, an analysis paradigm, and redevelopment recommendations to prioritize wells for maintenance with the goal of achieving long-term sustainable yields.

2. Art Background

Wells used for public water production, such as municipal water wells, are prone to reduction of yield over time. As used in this discussion "yield" refers to production of water from a well. Reduction in yield can result from different causes. For example, sometimes reduction in yield results from well screen or borehole clogging. Other times reduction in yield can result from changes in the aquifer or interference from other wells. Sometimes reductions in yield can erroneously be inferred due to inconsistent measurement methods used to measure well yield. For example, specific capacity measurements are one means used to measure well yield. However, during a specific capacity test a well draw-down measurement is made during a transient phenomenon of the aquifer (which is non-linear with respect to time and pumping rate) that occurs while a new semi-stationary depth to water is established in the well under the pumping condition. Current methods used for measuring specific capacity introduce error into the measurement thereby obscuring actual well yield. Knowing which cause is affecting yield in a given well is a technical problem that requires a technical solution.

Clogging occurs over a spectrum of severity and can result from different causes. Well clogging can progress at different rates for each well in a group of wells. Since clogging can result from different causes, knowing which cause(s) are operable in a given well is a technical problem that requires a technical solution.

If left unchecked, a clogged well experiences increase in pump head and ultimately a reduction in yield, meaning the well produces less water than it did when it was originally installed, this can result in diminished water production for the public and public safety (e.g., fire protection) as well as lost revenue. As an example, in one municipality in the United States in 2022, one million gallons of treated public water retails for approximately $4,000. A 1,000 gallon/minute well that is only yielding 800 gallons/minute is losing money for the municipality. A decrease of 200 gallons/minute (a 20% loss in yield) results in a loss of $1,152/day or approximately $420,000/year from one well. Municipalities have hundreds of wells in service and multiple wells experiencing even partial clogging results in losses on the order of millions of dollars/year. Knowing which well or wells to spend resources on in order to achieve the greatest gain in yield is a technical problem that requires a technical solution.

The current state of the art in assessing potential for clogging typically involves use of in well video to inspect a well's screen. Such video inspection can result in unnecessary redevelopment of a well due to inaccuracy in assessing potential for clogging from video inspection. Thus, resources can be wasted when the current state of the art is used to assess potential for clogging. Accurately assessing potential for clogging apart from video inspection is a technical problem that requires a technical solution.

BRIEF DESCRIPTION OF THE DRAWINGS

The invention may best be understood by referring to the following description and accompanying drawings that are used to illustrate embodiments of the invention. The invention is illustrated by way of example in the embodiments and is not limited in the figures of the accompanying drawings, in which like references indicate similar elements.

FIG. 5 illustrates well yield records for two wells over a period time, according to embodiment of the invention.

FIG. 9 illustrates plots of mobile particles as a function of time during a well startup transient for two wells, according to embodiments of the invention.

FIG. 12 illustrates bacteria activity data for two wells, according to embodiments of the invention.

FIG. 23A illustrates a comparison of well yield with and without use of a custom extended pump sleeve (CEPS), according to embodiments of the invention.

FIG. 24 illustrates a reduction in static water level of an aquifer and the effect on well yield, according to embodiments of the invention.

FIG. 29 illustrates additional components of a well yield evaluation worksheet (WYEW), according to embodiments of the invention.

FIG. 30 illustrates an analysis results component of a well yield evaluation worksheet (WYEW), according to embodiments of the invention.

FIG. 34 illustrates first equations used to calculate a Well Performance Metric (WPM), according to embodiments of the invention.

FIG. 35 illustrates second equations used to calculate Well Performance Metric (WPM), according to embodiments of the invention.

FIGS. 42A-42B illustrate a Well Maintenance Tracking Record for the group of 35 wells, according to embodiments of the invention.

FIGS. 43A-43B illustrate a Well Yield Classification Record for the group of 35 wells, according to embodiments of the invention.

FIG. 48 illustrates an automated system in which embodiments of the invention may be used.

DETAILED DESCRIPTION

In the following detailed description of embodiments of the invention, reference is made to the accompanying drawings in which like references indicate similar elements, and in which, is shown by way of illustration, specific embodiments in which the invention may be practiced. These embodiments are described in sufficient detail to enable those of skill in the art to practice the invention. In other instances, well-known circuits, structures, and techniques have not been shown in detail in order not to obscure the understanding of this description. The following detailed description is, therefore, not to be taken in a limiting sense.

Figure 1:
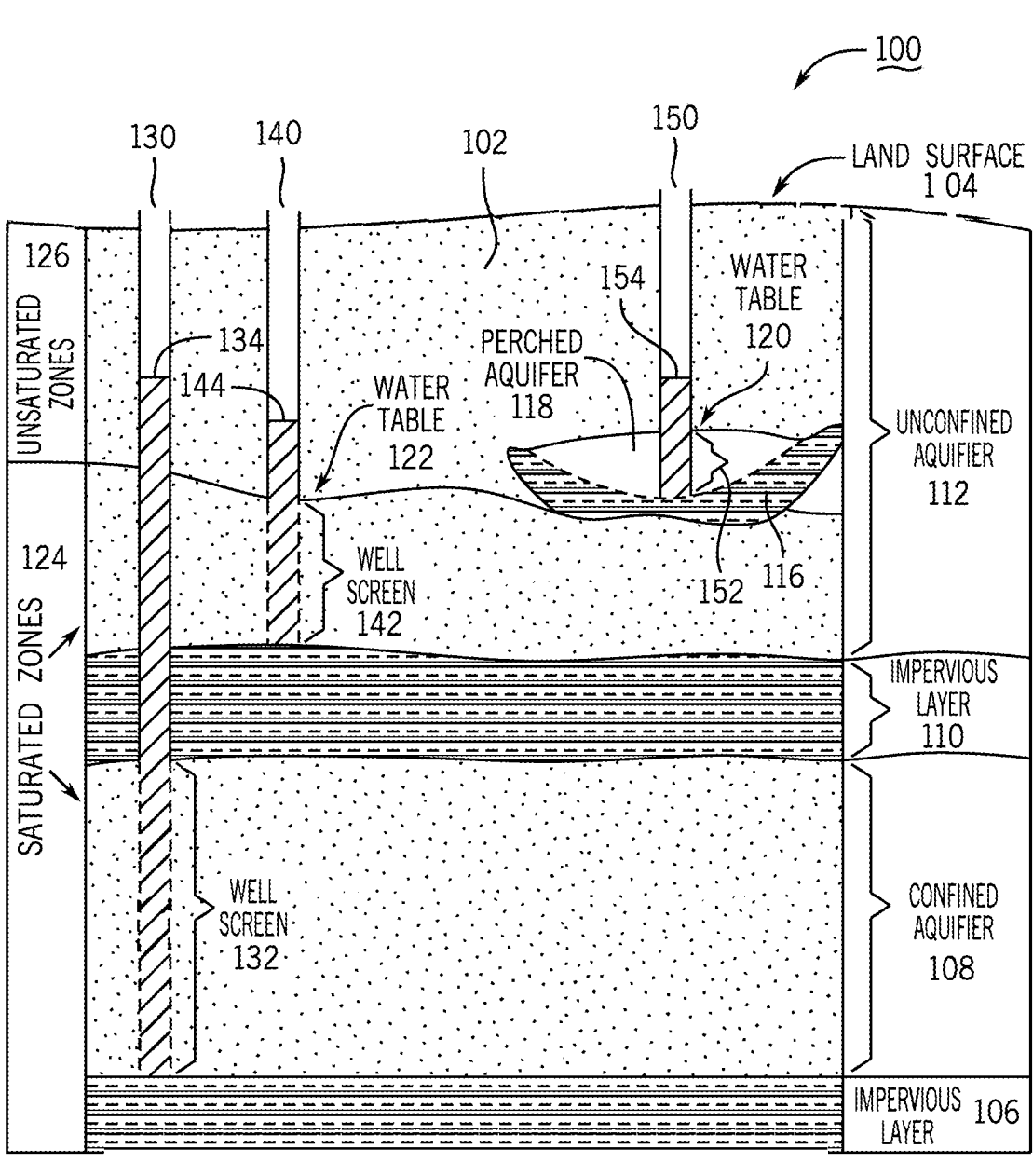
FIG. 1 illustrates different cross-sectional views of wells installed in various types of aquifers in which various embodiments of the invention can be used.

FIG. 1 illustrates different cross-sectional views of wells installed in various types of aquifers in which various embodiments of the invention can be used. Note that embodiments of the invention can be used with any type of aquifer. The aquifers illustrated in FIG. 1 are provided by way of example and do not limit embodiments of the invention.

With reference to FIG. 1, a confined aquifer 108 is bounded from below by an impervious layer 106 and from above by an impervious layer 110. An unconfined aquifer 112 is bounded from below by the impervious layer 110. The unconfined aquifer has a saturated zone 124 and unsaturated zone 126 and is bounded from above by the land surface 104. The unconfined aquifer 112 has a water table indicated at 122. A perched aquifer 118 is bounded from below by an impervious layer 116. The perched aquifer 118 borders the unsaturated zone 126. The perched aquifer 118 has a water table indicated at 120.

A well 130 extends down to the confined aquifer 108, has a well screen 132, and a static water level indicated at 134. A well 140 extends down to the unconfined aquifer 112, has a well screen 142, and a static water level indicated at 144. A well 150 extends down into the perched aquifer 118, has a well screen 152, and a static water level indicated at 154. The wells shown in FIG. 1 are depicted qualitatively with no implication on actual spacing or actual depth or actual dimensions. While the well screens have been illustrated as extending through the saturated zone 124 for the well 130 and the well 140, the well screens could only extend part way through the saturated zones 448 and 124. Thus, the wells are provided merely for illustration of some of the many wells in which embodiments of the invention can be implemented.

The wells shown in FIG. 1 are illustrated without a gravel pack for simplicity in the illustration. However, it will be understood that each well shown in FIG. 1 is constructed with a gravel pack be it natural material or installed material.

Embodiments of the invention can be used to analyze a well constructed with any gravel pack, such as but not limited to, gravel packs made using quartz material, etc. Typically, the material used for a gravel pack is provided using round gravel with the goal of retaining the formation and not plugging a well screen. There are also natural gravel pack wells to which embodiments of the invention can be applied.

Embodiments of the invention are applicable to well screens of any construction, such as but not limited to, wire-wrap screens, louvered screens, vertically milled slots, horizontally milled slots, torch cut perforations, mills knife perforations, etc.

Measuring and Estimating Well Yield-Specific Capacity (SC)

When a well is drilled into a saturated zone, such as 124 in FIG. 1, a static depth to water occurs in the well. Various static depths to water exist in wells depending on details of the aquifer that the wells are drilled into, such as depth of the water bearing layer, static pressure existing in the water bearing layer, confinement or lack of confinement of the aquifer, etc. When a pump connected to a well is turned to an ON state, water is extracted from the well. Pumping water from a well can create a pressure gradient that exists along a radial direction out from the well extending across a portion of a saturated zone of an aquifer that the well is drawing from thereby forming a cone of depression within the saturated zone around a well. Saturated zones, such as 124 in FIG. 1, present a porous medium through which water migrates as water travels to the well pipe. Observations of water migration through the porous medium of an aquifer show that once a well pump is turned to the ON state, a depth to water changes as a function of time. Thus, measurements of depth to water following transition from the quiescent state occur in the presence of a non-linear transient transport phenomena where a new stationary level is approaching but it takes time to reach the new stationary level. This change from a static depth to water in the OFF state to a new stationary depth to water in the pumping ON state can occur slowly and at different rates in different wells because of the different physical properties of a given aquifer and different pumping rates used in the different wells.

The parameter of specific capacity (SC) is often used to quantify well yield as a volume extracted per unit time per foot of draw down. In various embodiments, a methodology is taught herein that removes measurement error that has occurred historically with measurements of SC. Once the historical measurement error of SC is removed, SC measurements can be made on a given well over time, thereby providing useful information on changes in well yield over time for the given well. In addition, measurements of SC (occurring at a comparable time) can be compared across a group of wells located in the same or in different aquifers, thereby facilitating analysis of well yield that is free of historical measurement error for the group.

Figure 2:
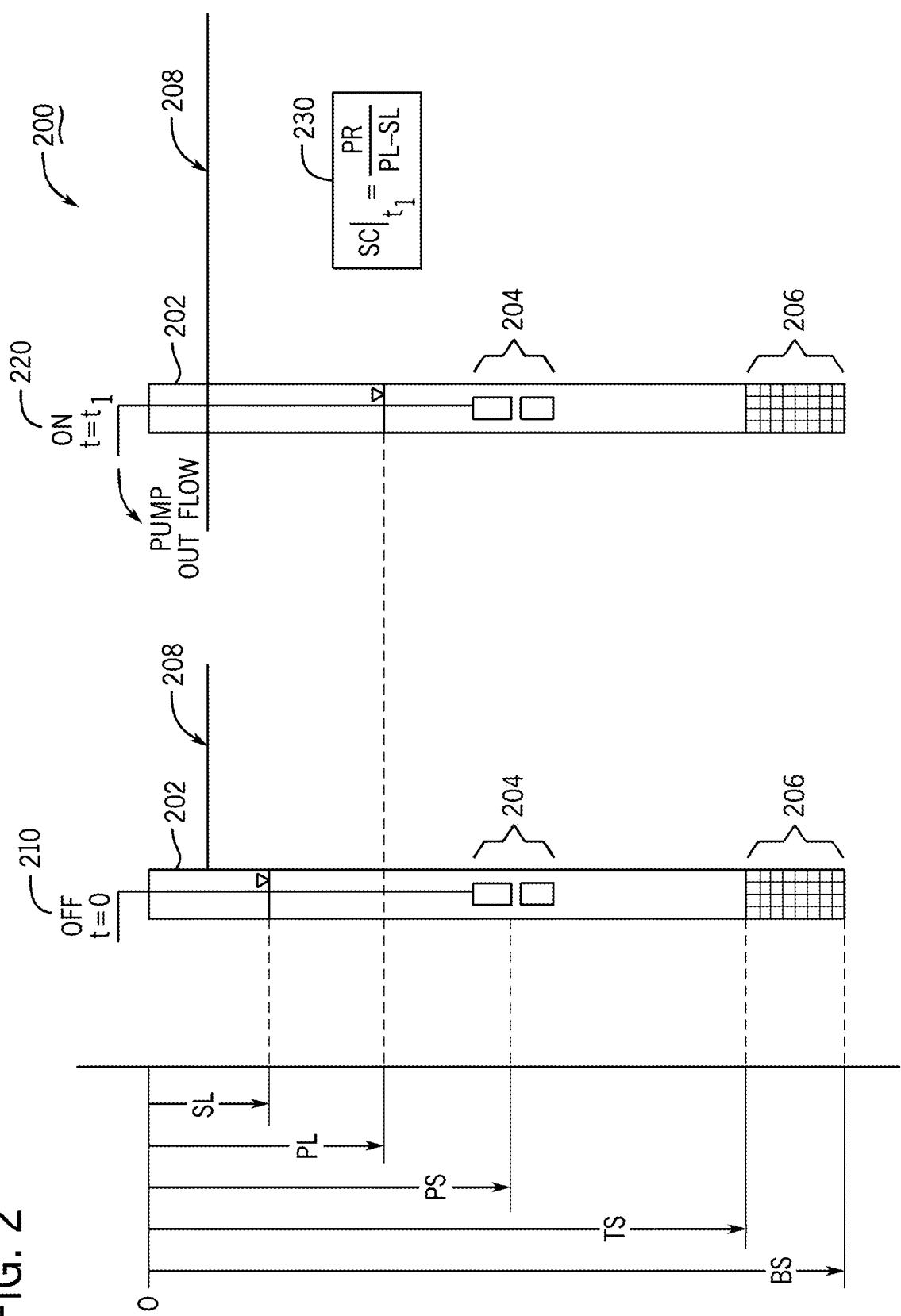
FIG. 2 illustrates a well at two points in time during a specific capacity measurement, according to embodiments of the invention.

FIG. 2 illustrates, generally at 200, a well at two points in time during a specific capacity (SC) measurement, according to embodiments of the invention. With reference to FIG. 2, a first point in time for the well is illustrated at 210 with the well in the quiescent or OFF state meaning that no water is pumped from the well and a depth to water in the well is at static level indicated at SL. SL is indicative of the water level in the well developed by the water pressure within an aquifer. The well is illustrated with a well casing 202 extending down into the aquifer. The water bearing layer of the aquifer is screened at 206 and a well pump/motor unit is illustrated at 204. The well pump 204 is set at a depth PS (pump setting). A top of the well screen is indicated at TS and a bottom of the well screen is indicated at BS.

A second point in time for the well is illustrated at 220. At 220, the well is illustrated in the ON state where the pump 204 has been operating at a given constant pumping rate PR after passage of time $t_1$. Thus, at 220 the depth to water in the well has increased from SL to PL under pumping rate PR. Meaning that the free surface of water in the well has been lowered with respect to the surface of the ground 208. The well has experienced a drawdown D which is the difference between the pumping level PL and the static level SL given by the following equation: D=PL–SL. Specific Capacity SC at time $t_1$ is calculated using equation 230 in FIG. 2. In the British system of units, Specific Capacity will have units of gallons/min/foot of drawdown.

In various embodiments, it is a goal of the SC estimation process to obtain a pumping level that does not change over time, which would be an equilibrium level or equivalently stated a stationary level for a given pumping rate. Because of the non-linear transient nature of drawdown during pumping, the pumping level will continue to move deeper into the well further away from the surface 208 as time progresses beyond $t_1$. This phenomenon is also referred to as a startup transient of the well from a quiescent state. It could take multiple days or weeks, even months of pump testing to pass through the startup transient in order to reach the equilibrium level for drawdown at the given pumping rate, which is the point where the pumping level stops changing.

A specific capacity test to attain stability in pumping level requires the well to pump continuously for an extended period, which is not prudent or practical. Therefore, it is desirable to perform a SC test in a short period of time. Thus, in various embodiments, a methodology is taught where the depth to water data, for example SL and PL, are collected above at time zero and $t_1$, respectively (FIG. 2), and then are extrapolated to a future time to obtain the equilibrium (nonchanging or approximately nonchanging) depth to water for the given pumping rate. Such extrapolation to a future time permits a SC test to occur over a short time such as a number of minutes rather than a number of days. Water level cover must exist above a well pump in order to keep the pump submerged. Embodiments of the invention are used to ensure that adequate water cover above the well pump is maintained. Measurement of depth to water in a well can be made with any of the various apparatuses as are known to those of ordinary skill in the art. An apparatus used to measure depth to water in a well does not limit embodiments of the invention.

Figure 3A:
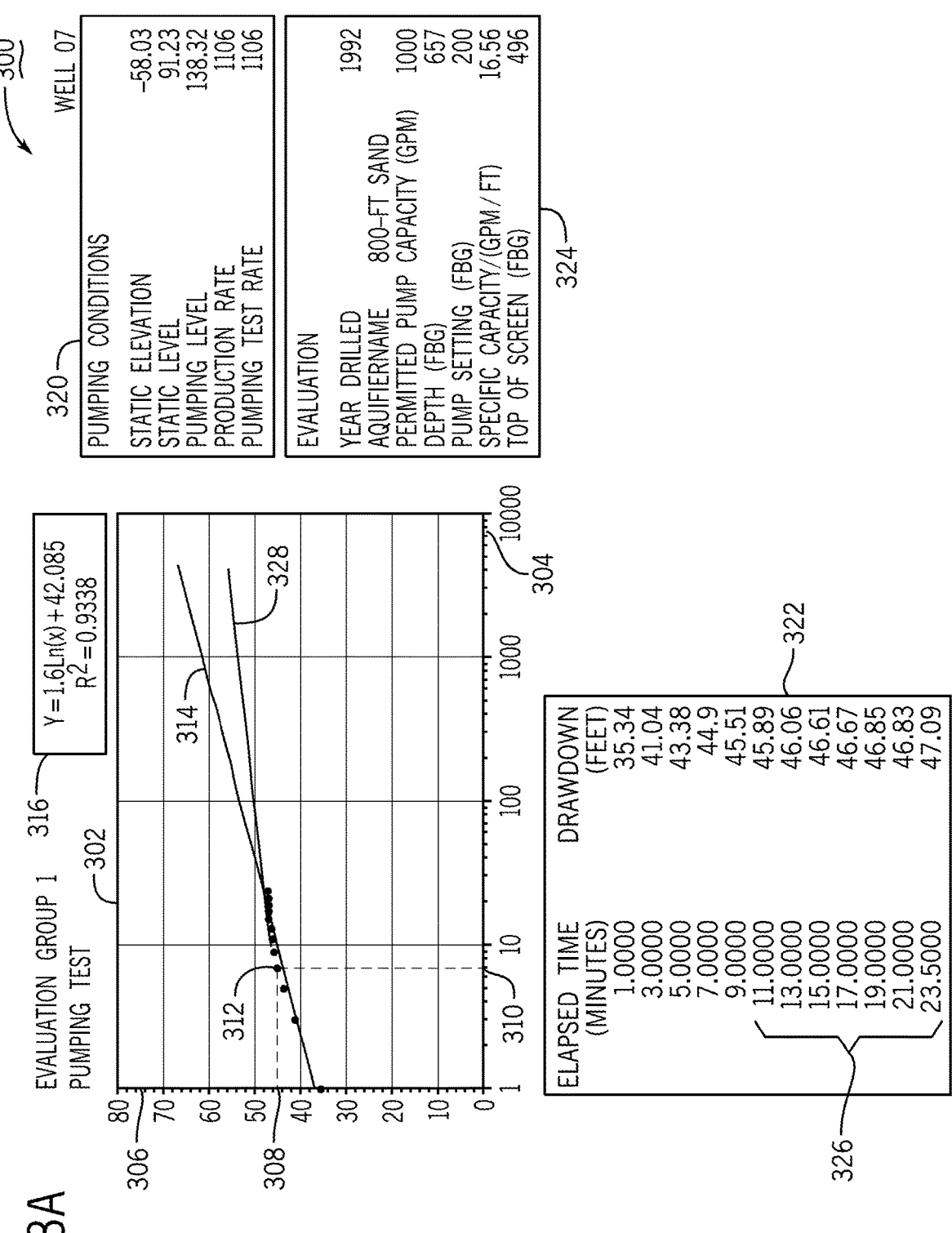
FIG. 3A illustrates a mathematical simulation extrapolating well drawdown to a future time, for use with embodiments of the invention.

FIG. 3A illustrates, generally at 300, a mathematical simulation extrapolating well drawdown to a future time, for use with embodiments of the invention. With reference to FIG. 3A, plotted data represents depth to water measurements taken during a specific capacity (SC) test lasting for approximately 30 minutes. In other embodiments, a pumping test can last for less than 30 minutes or longer that 30 minutes. Graph 302 is in semi-log format having a horizontal axis 304 incremented using a logarithmic scale for time (minutes) and a linear vertical axis 306 for drawdown (feet). During the specific capacity pumping test, depth to water is recorded along with corresponding values for time, the data are shown at 322. The data from 322 are plotted on the graph 302 using circles. One such data point 312 has a drawdown indicated at 308 (44.9 ft) and occurs at a time indicated at 310 (7 minutes). Line 328 represents a result of a curve fit using a mathematical model having constant slope to a segment of the data 322 collected during the SC pumping test. The segment starts at time t=11 minutes and ends at t=23.5 minutes, indicated at 326. A general linear equation for the curve fit is y=m*Ln(x)+b. Where y equals the drawdown, m equals the slope, x equals pumping time, Ln(x) represents natural logarithm to base e of time x, and b is the y intercept. After the curve fit process, the equation for the line of constant slope for WELL 07 is given at 316 as y=1.6*Ln(x)+42.085, and a coefficient of determination for the fit to the data is given as $R^2$=0.9338. Plotting the SC data shown in 302, on a semi-logarithmic plot, linearizes the drawdown phenomena to a straight-line having slope m=1.6, which results in a relationship between drawdown y and x as shown in equation 316.

The well, illustrated in FIG. 3A, is known in the art as a leaky well that reaches an equilibrium depth to water after a sufficient pumping time. Because of the leaky nature of the well, the time-drawdown data flattens (from the predicted straight line model) after ten minutes, and as such, the semi-logarithmic model will over predict depth to water at large extrapolation times. For example, when the entire data set shown in 322 (1 to 23.5 minutes) is used, the model obtained is: y=3.5851Ln(x)+36.763, and at time t=3 days the extrapolated depth to water is 66.8 feet which is the end point of the extrapolation indicated at 314. Using the segment described above (11 to 23.5 minutes), indicated at 326, produces an extrapolated depth to water of approximately 56.5 feet which is the end point of the extrapolation indicated at 328. The segmented pumping test, described above, is an example of how a segment is used from a pumping test on a leaky well to improve extrapolated depth to water estimates.

Note that the slope m of line 314 or line 328 can be obtained from only two points which are spaced apart in time and represent drawdown of a well under constant pumping rate. In practice, more than two points can be collected during a SC test as described above in 322. In various embodiments, and to facilitate other aspects of well yield analysis taught herein, approximately 30 minutes is used for a set pumping time. However, those of ordinary skill in the art will recognize that less than 30 minutes can be used or more than 30 minutes can be used and that 30 minutes is provided merely for illustration with no limitation implied thereby.

Extrapolation of a depth to water which will exist after drawdown from continuous pumping at a known pumping rate is obtained with the mathematical model given by 316 and the empirically obtained data 322. The equation 316 is evaluated for x at future times $t_{f1}$ and $t_{f2}$. In various embodiments, described below $t_{f1}$ is chosen to be 1 hour and $t_{f2}$ is chosen to be 3 days. Three days is used because it is a reasonable approximation to a steady state depth to water that will occur in the presence of the fixed pumping rate. Further discussion of the one 1-Hour and 3-Day SC predictions is given below in conjunction with the discussion of Well Yield Evaluation Worksheets (WYEW). Note that times other than 1 hour and 3 days can be used with equation 316. One-hour and 3-Day extrapolation time values are given for illustration and do not limit embodiments of the invention.

Pumping conditions for the specific capacity test are given at 320. The 3-Day evaluation of specific capacity is given at 324. Line 314 represents a simulation of pumping beyond the 30-minute test. When 316 is evaluated at the extrapolated 3-Day time of 4,320 minutes, a drawdown of 60.38 feet is obtained from 302. A specific capacity estimate extrapolated to the 3-Day pumping time is 16.56 gpm/ft=1000 gpm/60.38 ft. Using the segment of pumping data indicated at 326 results in a specific capacity estimate extrapolated to the 3-Day pumping time of 17.70 gpm/ft=1000 gpm/56.5 ft. Use of the segment improves accuracy in the estimation of specific capacity at extrapolated pumping times.

Note that different mathematical models for drawdown as a function of time can be used in place of the linear model given by equation 316. For example, a higher order polynomial model, an exponential model, a concatenation of models, or a user defined model can be used in place of equation 316. The linear model described herein utilizing equation 316 is given by way of example only and does not limit embodiments of the invention.

Figure 3B:
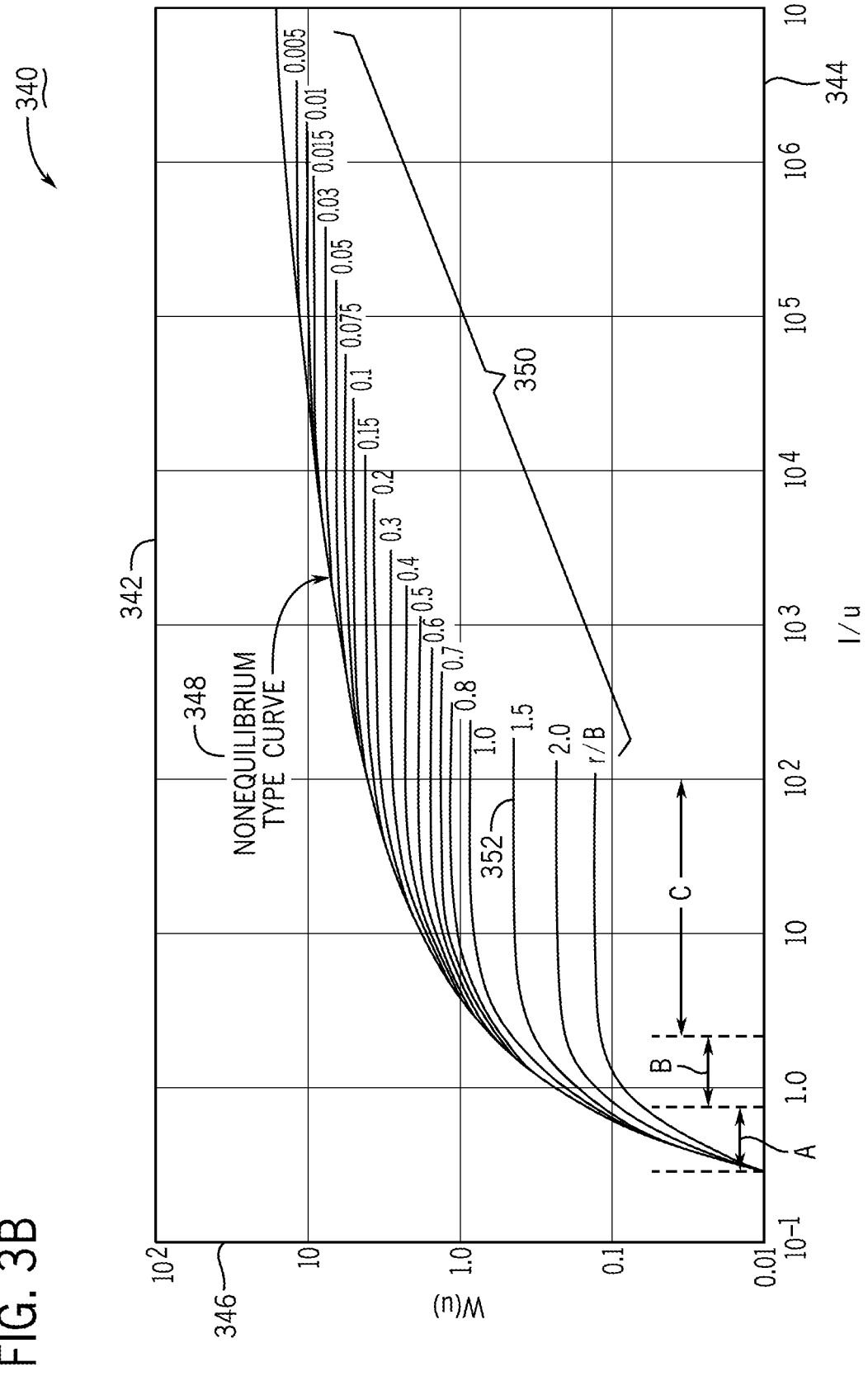
FIG. 3B illustrates a family of type curves to which embodiments of the invention can be applied.

As described above, embodiments of the invention are applicable to wells installed in different aquifers. A data collection time interval for the SC measurement can be dependent on the type of aquifer that a given well is installed in. The following example illustrates considerations for selecting a data collection time interval in a leaky confined aquifer and is given for illustration only and does not limit embodiments of the invention. FIG. 3B illustrates, generally at 340, a family of type curves for a leaky confined aquifer. The type curves in FIG. 3B are reproduced from W. C. Walton, Illinois State Water Survey Bulletin 49, 1962. With reference to FIG. 3B, the family of type curves 350 is plotted in 342 with non-dimensional time (1/u) along a horizontal axis 344 and non-dimensional drawdown W(u) plotted at 346. A nonequilibrium type curve is plotted at 348 and the family of type curves 350 are plotted with the coefficient r/B varying between 0.005 and 2.5. The non-equilibrium type curve 348 represents a well in a non-leaky confined aquifer. A well in this type of aquifer reaches a constant depth to water under pumping conditions over some pumping time, as such, does not continue to "theoretically" drawdown indefinitely as exhibited in uppermost curve 348 which is referred to in the art as a "Theis curve" and is labeled "Nonequilibrium Type Curve 348" in FIG. 3B. With respect to FIG. 3B, u=r²S/Tt, where r is equal to a radial distance to a point of observation. The point of observation is the point where depth to water measurements are made. Thus, r can be a distance within the wellbore or outside of the wellbore. S is equal to a coefficient of storage fraction. T is equal to a coefficient of transmissivity. t is equal to elapsed pumping time. W (u, r/B) is equal to the well function derived from table 3.5 of "Groundwater and Wells," by Walton p 146, 1970. B=√(T/P'/m'), where P' equals the coefficient of permeability of the aquitard layer and m' equals the aquitard thickness.

Each of the equilibrium type curves 350 can be characterized by three regions, a first initial quick drawdown, a second region which represents a transition in drawdown, and a third region which represents a plateau region in drawdown culminating in a new stationary depth to water which will occur under a fixed pumping rate. An example of these three regions, indicated by A, B, and C, is illustrated with respect to type curve 352. The first initial quick drawdown region is nominally indicated at A. The second region is nominally indicated at B. And the third region is nominally indicated at C. It has been discovered that it is beneficial to collect data during a SC measurement over a time interval that includes at least a portion of region A and at least a portion of region B, and if possible, a portion of region C. Data collection over the interval so defined is used with a model(s) as described above, and in some cases a segment of the data, to create a simulation of drawdown at an extrapolated future time(s).

Figure 3C:
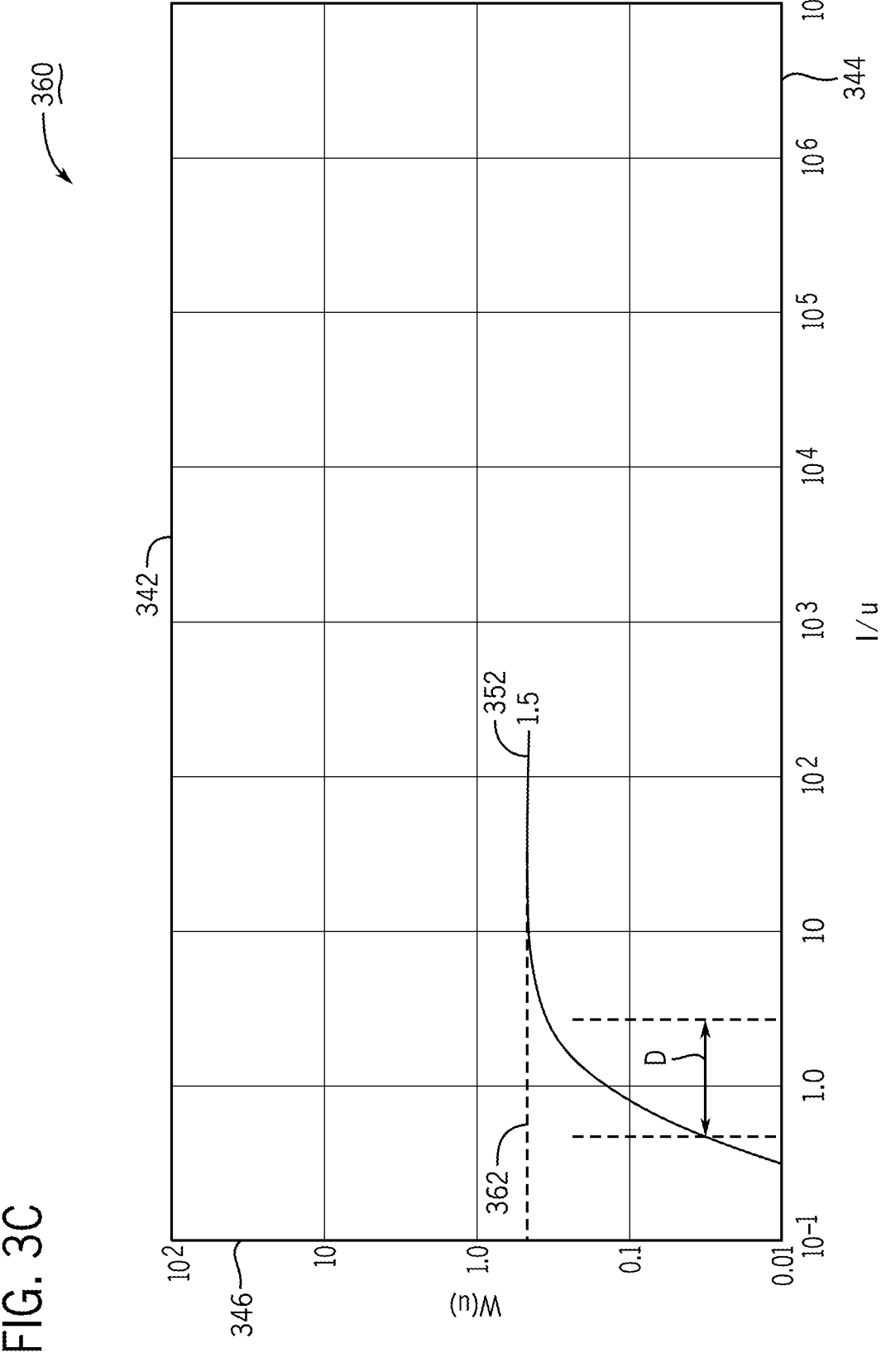
FIG. 3C illustrates a data collection interval according to embodiments of the invention.

FIG. 3C illustrates, generally at 360, a data collection interval according to embodiments of the invention. With reference to FIG. 3C, type curve 352 is illustrated by itself to provide clarity in the illustration. A data collection interval is indicated at D for the type curve 352. Note that interval D includes a portion of region A and region B, both of which are illustrated in FIG. 3B. The width in time illustrated for the interval D is provided for example only and does not limit embodiments of the invention. More or less of region A could have been included in the interval D and likewise more or less of region B could have been included in the interval D. A portion of region C could have been included in the interval D. The interval D is used for data collection during a SC measurement together with a model for drawdown as a function of time in order to extrapolate a depth to water to a future extrapolated time(s). The same principles applied to curve 352 can be applied to the other curves within the family of curves 350. The same principles described above in conjunction with FIG. 3B and FIG. 3C are applicable to type curves of other aquifers. In such cases, with other aquifers, as described above, a variety of different models can be used for drawdown as a function of time to provide the required extrapolated depth to water. Note that the aquifer represented by type curve 352 is a leaky aquifer which achieves an equilibrium drawdown indicated at 362. In various embodiments, use of a segment as described above to data collected during a specific capacity test is applicable to any type curve from any aquifer.

Figure 3D:
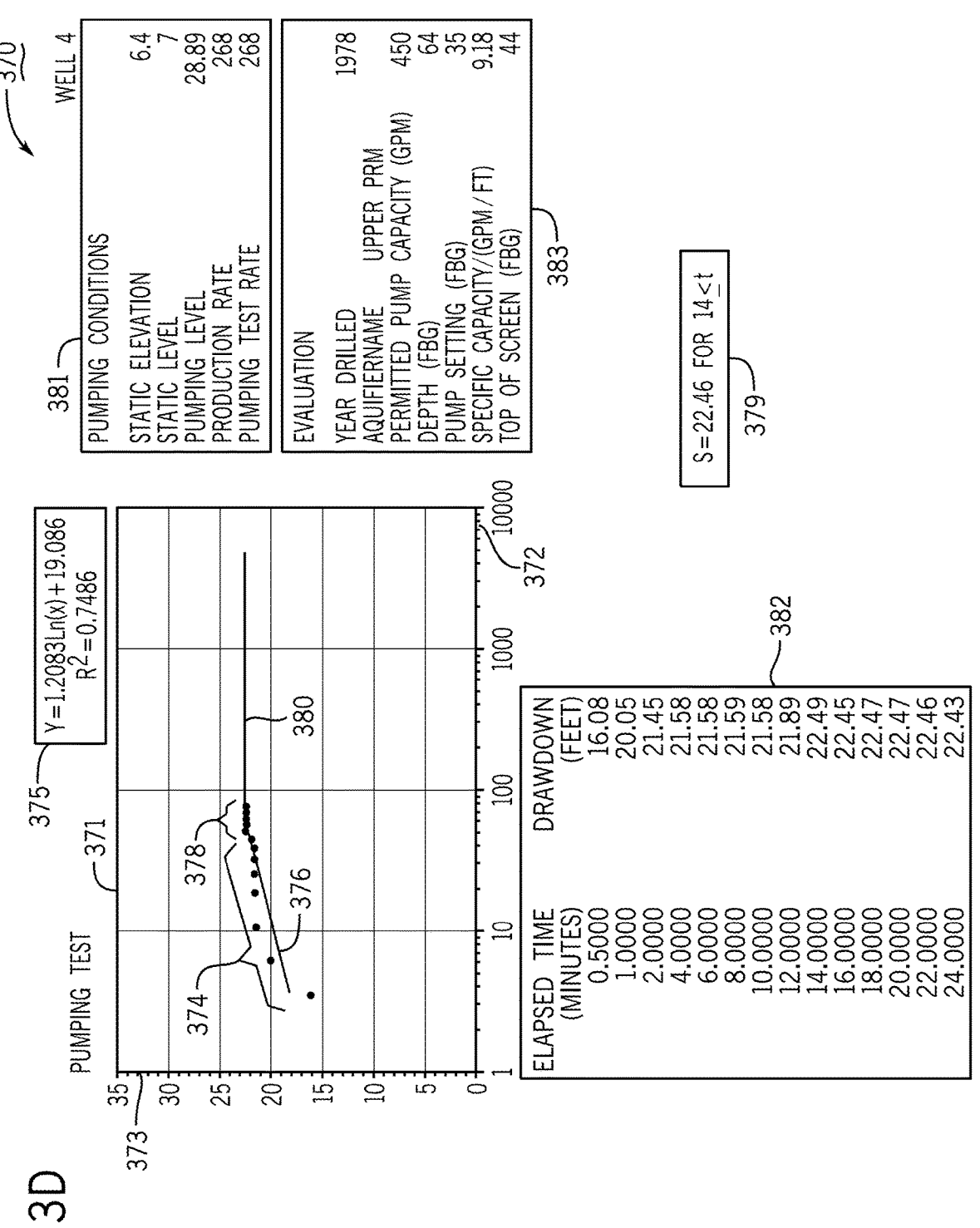
FIG. 3D illustrates a mathematical simulation extrapolating well drawdown using a concatenation of models, according to embodiments of the invention.

FIG. 3D illustrates, generally at 370, a mathematical simulation extrapolating well drawdown using a concatenation of models, according to embodiments of the invention. With reference to FIG. 3D, plotted data represents depth to water measurements taken during a specific capacity (SC) test lasting for approximately 24 minutes. In other embodiments, a pumping test can last for less than 24 minutes or longer than 24 minutes. WELL 4 is a shallow well next to a lake. WELL 4 experiences leakage early in the pumping test and then stops drawing down when it connects to the lake. Thus, a nominal 30-minute pumping text passes through regions A, B, and enters region C (FIG. 3B).

Graph 371 is in semi-log format having a horizontal axis 372 incremented using a logarithmic scale for time (minutes) and a linear vertical axis 373 for drawdown (feet). During the specific capacity pumping test, depth to water is recorded along with corresponding values for time, the data are shown at 382. The data from 382 are plotted on the graph 371 using circles. Line 376 represents a result of a curve fit using a model having constant slope to a segment of the data 382 collected during the SC pumping test. A first segment starts at time t=0.5 minutes and ends at t=12 minutes, indicated at 374. A general linear equation for the curve fit is y=m*Ln(x)+b, where y equals the drawdown, m equals the slope, x equals pumping time, Ln(x) represents natural logarithm to base e of time x, and b is the y intercept. After the curve fit process, the equation for the line of constant slope for WELL 4 is given at 375 as y=1.2083*Ln(x)+ 19.086, and a coefficient of determination for the fit to the data is given as R²=0.7486. Plotting the SC data shown in 371 for the first segment linearizes the drawdown phenomena to a straight-line with equation given at 375, having slope m=1.2083, which results in a relationship between drawdown y and x as shown in equation 375 for time t=0.5 to t=12 minutes.

The data is partitioned into a second segment from t=14 minutes to t=24 minutes, indicated at 378. A model for the second segment 378 is given by the equation at 379, where s=22.46 feet for times greater than or equal to 14 minutes. The model that results for the data collection interval is the concatenation of the first model 375 and the second model 379. Note that if the model shown at 375 had been used exclusively to estimate drawdown at the 3-Day extrapolation time significant overprediction would have resulted and specific capacity would have been underpredicted. At the 3-Day extrapolation time, the model at 375 produces an estimate of 9.18 gpm/ft and the model at 379 produces an estimate of 11.95 gpm/ft. Using the multisegmented procedure enables a more precise calculation of specific capacity for WELL 4.

Figure 3E:
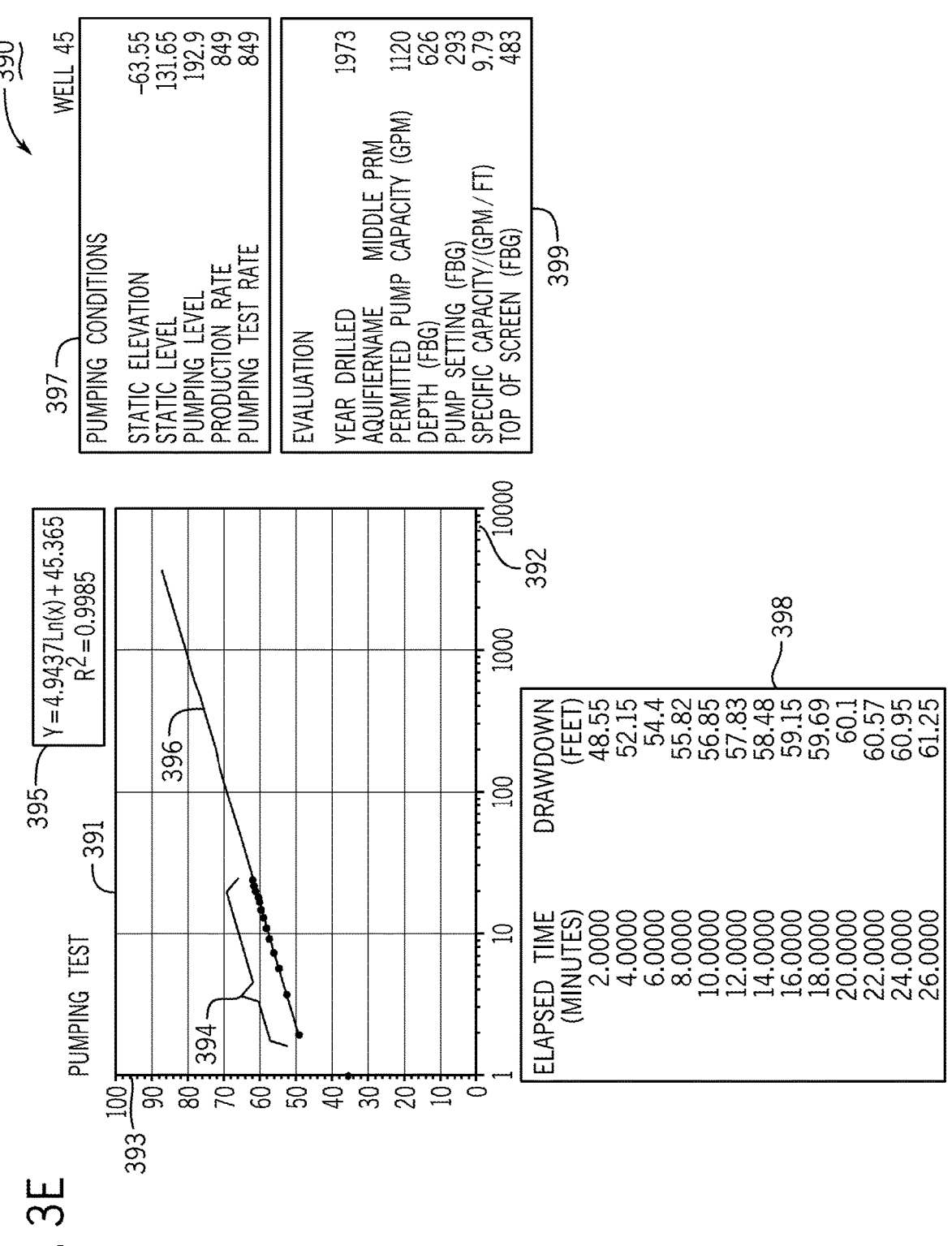
FIG. 3E illustrates a mathematical simulation extrapolating well drawdown to a future time on a well with minimal leakage for use with embodiments of the invention.

FIG. 3E illustrates, generally at 390, a mathematical simulation extrapolating well drawdown to a future time on a well with minimal leakage for use with embodiments of the invention. With reference to FIG. 3E, WELL 45, illustrated therein, follows a Theis behavior and is substantially a non-equilibrium well that keeps drawing down under constant pumping conditions. Data plotted on graph 391 represents depth to water measurements taken during a specific capacity (SC) test lasting for approximately 30 minutes. In other embodiments, a pumping test can last for less than 30 minutes or longer than 30 minutes. Graph 391 is in semi-log format having a horizontal axis 392 incremented using a logarithmic scale for time (minutes) and a linear vertical axis 393 for drawdown (feet). During the specific capacity pumping test, depth to water is recorded along with corresponding values for time, the data are shown at 398. The data from 398 are plotted on graph 391 using circles. Line 396 represents a result of a curve fit using a mathematical model of constant slope to the data 398 collected during the SC pumping test. A general linear equation for the curve fit is $y=m*Ln(x)+b$, where y equals the drawdown, m equals the slope, x equals pumping time, $Ln(x)$ represents natural logarithm to base e of time x, and b is the y intercept. After the curve fit process, the equation for the line of constant slope for WELL 45 is given at 395 as $y=4.9437*Ln(x)+45.365$, and a coefficient of determination for the fit to the data is given as $R^2=0.9985$. Plotting the SC data shown in 398 linearizes the drawdown phenomena to a straight-line 396 with equation given at 395, having slope m=4.9437, which results in a relationship between drawdown y and x as shown in equation 395. Equation 395 is used to estimate drawdown at extrapolated times such as the 3-Day extrapolated pumping time resulting in a specific capacity estimate for WELL 45 of 9.79 gpm/ft as shown in 399.

Figure 4:
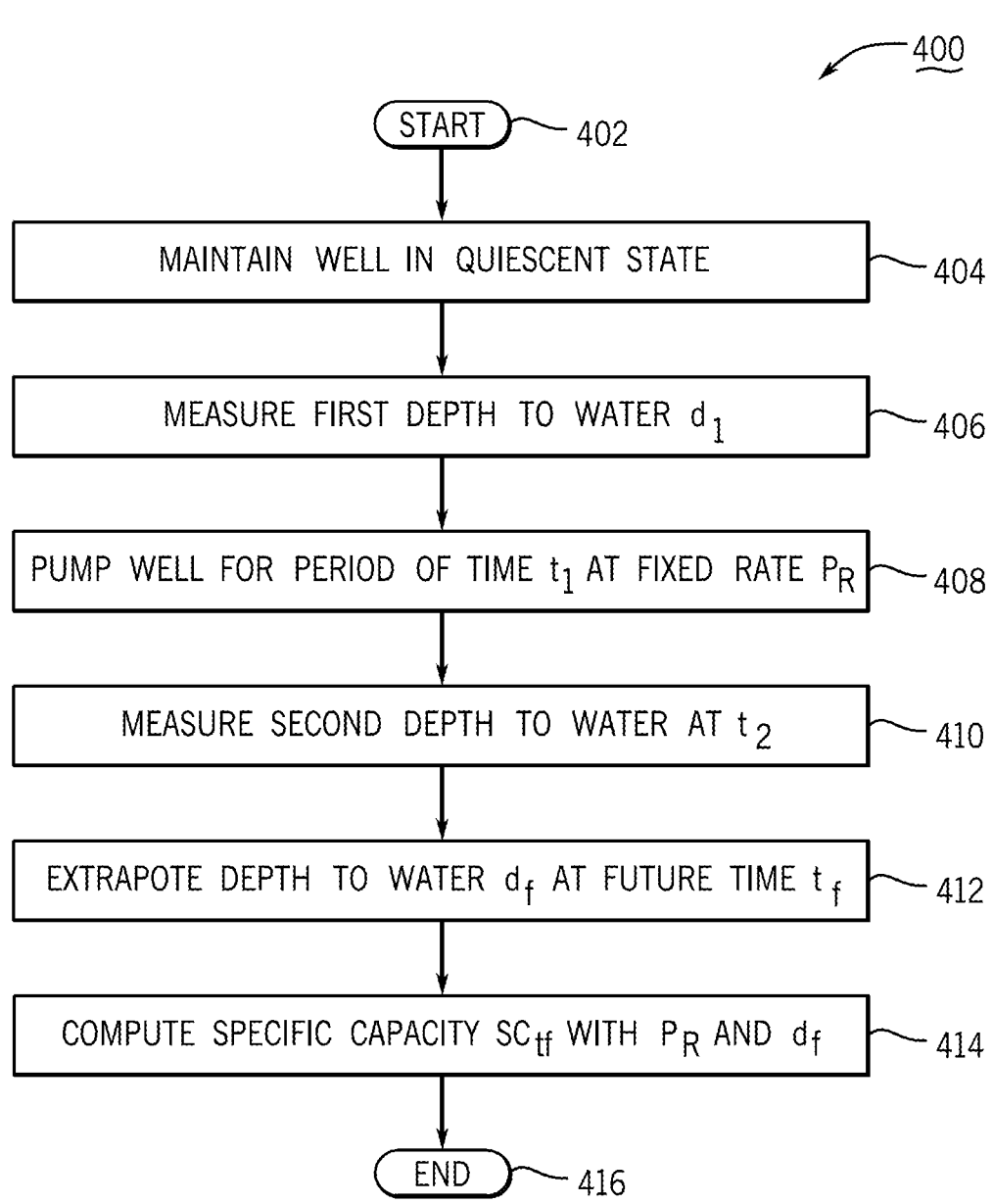
FIG. 4 illustrates a method for obtaining uniform specific capacity measurements, according to embodiments of the invention.

FIG. 4 illustrates, generally at 400, a method for obtaining uniform specific capacity measurements, according to embodiments of the invention. With reference to FIG. 4, a process commences at a block 402. At a block 404 a well is maintained in a quiescent state for a first period of time. The first period of time is sufficient to place the well in a quiescent state so that the depth to water stabilizes. In various embodiments, the first period of time can be over night. In other embodiment, the first period of time can be approximately 8 to twelve 12 hours. The first period of time can vary from well to well, what is important is that the depth to water stabilizes to the static level during the first period of time. Such a quiescent state is as shown above in FIG. 2 at 210. At a block 406 a first depth to water is measured. The first depth to water is for example, in one or more embodiments, SL indicated in FIG. 2. At a block 408 the well is turned to an ON state for a first pumping time at a fixed pumping rate. In various embodiments, an example of a first pumping time and fixed pumping rate is illustrated in FIG. 2 as pumping rate (PR) and time $t_1$ at 220. At a block 410 a second depth to water is measured after the first pumping time. In various embodiments, an example of a second depth to water, obtained after a first pumping time $t_1$ at fixed pumping rate PR, is PL as shown in FIG. 2. At a block 412 a depth to water $d_f$ is extrapolated to a future time $t_f$. In various embodiments, the extrapolated depth to water at future time $t_f$ is obtained as described above in conjunction with FIG. 3A, FIG. 3B, FIG. 3C, FIG. 3D, and FIG. 3E. At a block 414 a specific capacity ($SC_{tf}$) for the well is computed using the extrapolated depth to water $d_f$, the fixed pumping rate, at future time $t_f$. The following equation gives the resulting specific capacity at future time $t_f$ as: $SC_{tf}$=Pumping rate/$d_f$. Noting that $d_f$ occurs at the extrapolated future time $t_f$ which is beyond the actual pumping time utilized during the SC test. In various embodiments, the methods taught herein recognize the transient non-linear nature of the well drawdown phenomena and are directed at overcoming the measurement error that exists in specific capacity measurements made within the current state of the art while limiting well down time for the SC test. SC measurements made utilizing the methods described above permit accurate comparison of SC measurements from a given well or from well to well within or across well fields.

FIG. 5 illustrates well yield records for two wells, generally at 500 and 550, over a period time, according to embodiment of the invention. With reference to FIG. 5, a first well at 500 illustrates well yield for a properly functioning well and a second well at 550 illustrates well yield for a well suffering from continuous reduction in yield.

The well yield record 500 plots time along a horizontal axis at 504 and specific capacity along a vertical axis at 502. A horizontal reference line 514 indicates a maximum specific capacity for the well that existed when the well was constructed or redeveloped. A reference line 516 indicates a level of specific capacity that is 80% of the maximum. A reference line 518 illustrates a level of specific capacity that is 50% of the maximum. Four measurements of specific capacity are plotted at 506, 508, 510 and 512. A number of months separate each of the four specific capacity measurements. As used in this description of embodiments, a number of months can span one or more years including any integer number of years and fractional portion of a year or fractional portion of a year. Thus, the term "number of months" is to be afforded a general meaning in a non-limiting way of any time interval. Note that the measurements 506 through 512 are not uniformly spaced. No limitation is implied by the spacing and it will be appreciated that different spacings between measurements of specific capacity are within the teachings presented herein. A line indicated at 520 represents an average of the four specific capacity measurements 506 through 512. The slope of line 520 is approximately zero indicating that the specific capacity of the well is remaining constant over time. Thus, the yield depicted in 500 is that of a healthy well that is not experiencing loss of yield. A very different situation exists for the well shown at 550.

The well yield record 550 plots time along a horizontal axis at 554 and specific capacity along a vertical axis at 552. A horizontal reference line 564 indicates a maximum specific capacity for the well that existed when the well was constructed or redeveloped to its maximum value plotted at 580. A reference line 566 indicates a level of specific capacity that is 80% of the maximum 564. A reference line 568 illustrates a level of specific capacity that is 50% of the maximum 564. Four measurements of specific capacity are plotted at 556, 558, 560 and 562. A number of months separate each of the four measurements of specific capacity 556, 558, 560 and 562. A line 570 is fit to the specific capacity data points 556 through 562. Specific capacity measurement 556 is just above the 80% line 566. A slope of the line 570 is negative which illustrates a continuous reduction in well yield over time falling from a maximum at

580 to a minimum value at 562. The rate of decline in specific capacity is a metric that is representative of well health. A rate of decline in specific capacity is used in well maintenance ranking as described below in sections that follow. Decline in specific capacity is a result of well clogging. Decline in specific capacity is a metric that can be used to estimate a time to failure of a well. Estimated time to failure of a well can be defined as the estimated time for a well's specific capacity to fall to a threshold value.

Clogging Overview—3 Modalities of Causation

As described above with reference to FIG. 1, each well illustrated therein can have its own unique set of operating parameters, e.g., pumping level depth to water, pumping rate, exposure to local minerals and metals from the water flowing in the aquifer, etc. various types of bacteria present in the aquifer, all of which are based on the local geological composition of the aquifer a well is drilled into and how the well is constructed and operated. Due to differences in the depth of the wells, differences in geology local to a given well, well clogging can vary from well to well and have different or similar causes in each well. Various embodiments of the invention are applied to a single well or to a group of wells to monitor well health and to establish causes for clogging. Well monitoring and clogging diagnostics, as described herein, can be used to identify and remediate causes of clogging before well yield is adversely affected. In yet other embodiments, where a well has not undergone a monitoring program and has suffered losses due to clogging to the point of adversely effecting yield, the causes of clogging can be diagnosed and in many instances can be "unclogged" (sometimes requiring redevelopment) thereby restoring yield. In light of the causes of clogging discovered for a given well, changes in the operation of the well can be applied to future operation of the well in order to slow the rate of yield decline.

Figure 6:
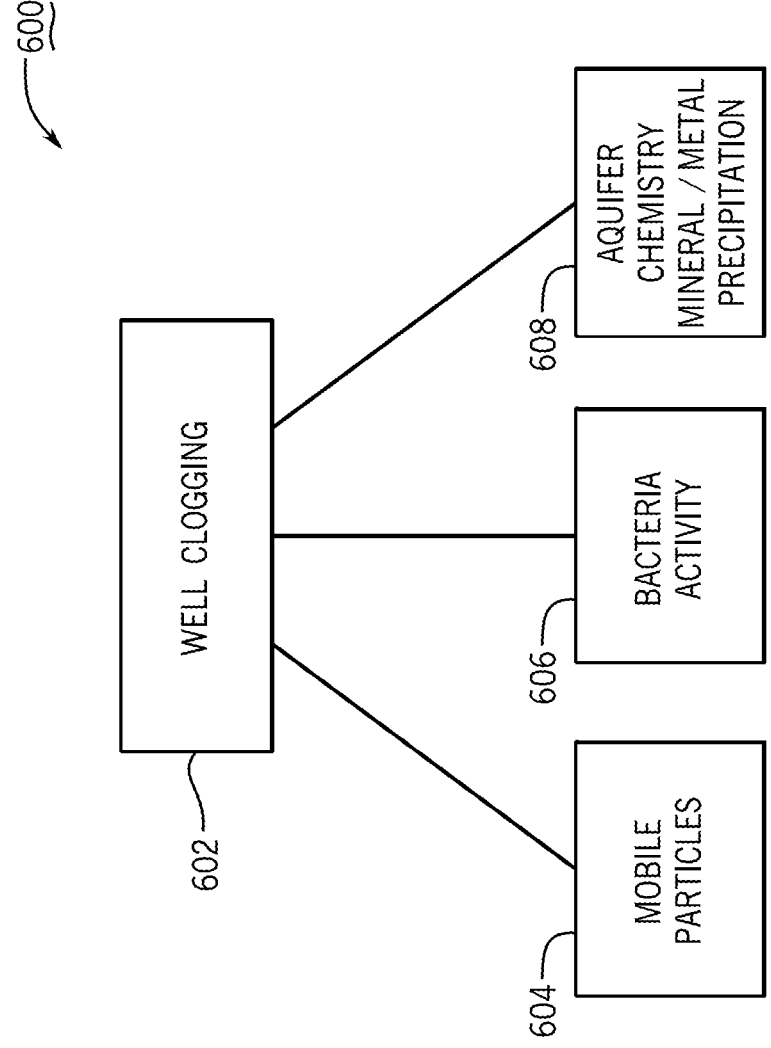
FIG. 6 illustrates multiple causes of well clogging, according to embodiments of the invention.

FIG. 6 illustrates, generally at 600, multiple causes of well clogging, according to embodiments of the invention. It has been discovered that the clogging phenomena occurring in a well has three causes which often progress slowly over time. With reference to FIG. 6, well clogging 602 can have one or more of the following three causes, i.e., mobile particles 604, bacteria activity 606, and mineral/metal precipitation 608. The three causes either individually can impact well yield. Understanding a cause or causes of the clogging processes that are operable in a particular well permits informed treatment or redevelopment of the well. Such informed treatment or redevelopment focuses on the cause(s) of the clogging through the use of various embodiments of the systems and methods described herein.

Capturing Clogging Specific Information

It has been discovered that valuable information on the causes of well clogging is contained in the groundwater that flows initially through the formation (aquifer) and then the gravel/pack while enroute to a well pump, referred to herein as "formation/gravel pack" during a start-up transient of a well. For example, as water flows past the colloids and silts in the formation/gravel pack, bacteria are dislodged therefrom and are pumped out of the well in the form of mobile particles. These bacteria and other mobile particles (colloids, silts, and fine sand) are examples of specific clogging information (SCI) that pertains to a particular well.

It has also been discovered that mobile particles peak during a start-up transient of a well. When mobile particles peak SCI also peaks. Thus, SCI, such as the bacteria residing in the formation/gravel pack and the quantity of mobile particles, detected in the water pumped from the well also peaks. This is because the SCI travels with and is contained in or with the mobile particles.

Water Sampling & Data Collection Time Intervals

Figure 7A:
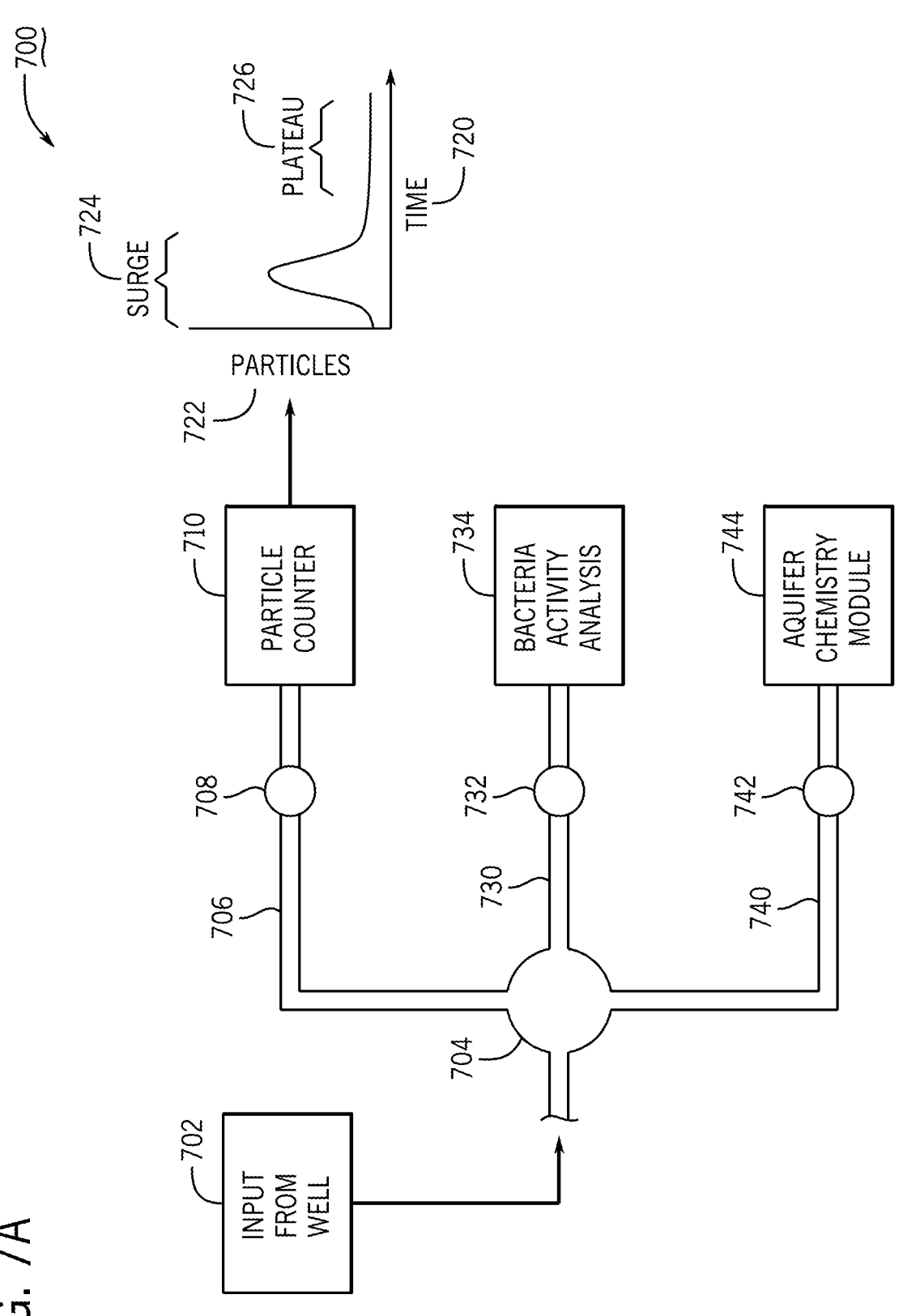
FIG. 7A illustrates water sampling in support of clogging analysis, according to embodiments of the invention.

FIG. 7A illustrates, generally 700, water sampling in support of clogging analysis, according to embodiments of the invention. With reference to FIG. 7A, a well water sampling system is illustrated. The well water sampling system receives an input of water from a well at 702. The input of water flows into a distribution manifold 704. A first branch 706 provides a first stream of water to a particle counter 710. A device such as a valve 708 is used to regulate the flow of water into the particle counter 710. A second branch 730 provides a second stream of water to a bacteria activity analysis block 734. A device such as a valve 732 is used to regulate the flow of water into the bacteria activity analysis block 734. A third branch 740 provides a third stream of water to an aquifer chemistry module 744. A device such as a valve 742 regulates water into the aquifer chemistry module 744. The water sampling system is constructed with pipes, valves, and various hardware used to direct a flow of water as is known to those of ordinary skill in the art. The water sampling system can be installed in an infrastructure that supports a well(s) installation or it can be configured as a mobile device that is brought to a well(s) and hooked up for test purposes and then removed. Thus, the deployment of the well water sampling system is flexible.

Prior to the start of a test, a well is in an OFF state for a period of time, for example, overnight for approximately 8-12 hours, so that the aquifer can remain in a mostly quiescent state for this period of time. It is important for the well to have remained in the OFF state for the suitable time as described herein because if the well were to be in continuous use, or not in the OFF state for a sufficient period of time prior to the test, upon testing, the well water would appear to be "clean" because such a test would be using water taken subsequent in time from the occurrence of a peak (surge) in mobile particles described above, thereby missing the SCI contained in the surge of mobile particles.

It has been discovered that the number of mobile particles that flow during a well start-up transient changes with increased time that the well remains in the off state. Therefore, to facilitate comparison of mobile particle measurements over a number of months, such as annual measurements, it is desirable to keep the well in the OFF state for the same fixed period of time right before the well is transitioned to the ON state for water sample collection during each test. Doing so increases the consistency of the mobile particle data measured from test to test.

Consistency of the data collection time interval is important because, as described above, SCI is contained in and with the mobile particles and in the concentration of mobile particles transported by the water pumped from a well and varies as a function of time. Thus, the peak of mobile particles, for example 724, is a relatively short-lived phenomenon lasting typically several minutes, but can be approximately 30 minutes or longer. Typically, the surge in mobile particles, for example 724, lasts less than 5 minutes. One of the goals of the well analyses, described herein, is to acquire a record of data relevant to well clogging in a particular well. The record is compiled from multiple measurements performed over an extended period of time, for example, performing measurements over a period of weeks, months, or years. To this end, during each well test, it is important to: (1) capture the peak of mobile particles, (2) measure the absolute number of mobile particles at the peak, and (3) collect a well water sample for bacterial analysis during the peak. Thus, a pump ON time of 30 minutes has been selected (based on numerical analysis of a multitude of pumping test data) as the time interval for use in tests performed on a given well. Alternatively, 1 hour could have been selected, or a different time, e.g., 1.5 hrs., etc. Thirty minutes is long enough to collect the SCI while minimizing down time for a well. Thus, production down time and lost revenue are minimized.

Note that a 30-minute data collection time interval for the specific clogging information is also adequate for the depth to water data collection required for the specific capacity measurement described in conjunction with the figures above. It is desirable for the specific capacity measurement, to keep the well in the quiescent state for a period of time sufficient to substantially stabilize the depth to water level in the well. The specific capacity measurement can be combined together with the water sample collection procedure for collection of clogging specific information (SCI) (FIG. 7A) by keeping the well in the OFF state long enough to satisfy the requirements of the specific capacity test and the clogging modality tests described below.

The aquifer chemistry module 744 is used to measure oxidation reduction potential (ORP) and potential of hydrogen (pH) of a sample of water taken from the well. ORP measurements are more stable following the surge of mobile particles. Therefore, it is preferable to collect a water sample for the ORP and pH measurements from the third stream 740 after the surge when mobile particles have plateaued.

In various embodiments, a particle counter 710 is used to gate water sample collection by quantifying a concentration of mobile particles 722 as a function of time 720 in order to establish when a peak in mobile particles and mobilized bacteria is occurring at 724 as well as when a plateau of mobile particles is occurring at 726. Thus, the particle counter 710 provides valuable information needed during water sample collection. Water samples are drawn from the well and analyzed as described below in the figures that follow.

Figure 7B:
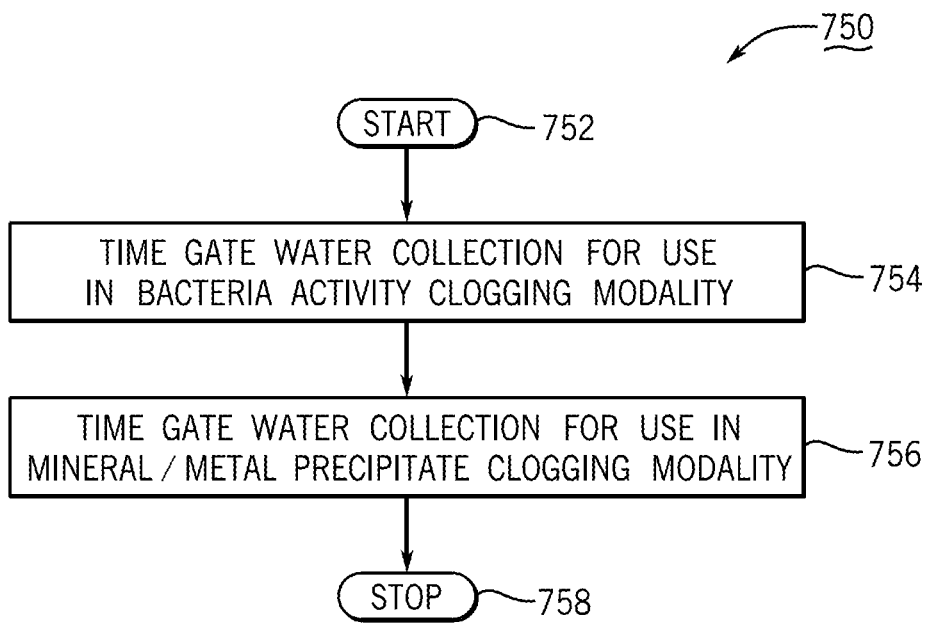
FIG. 7B illustrates a process for time gating water sample collection, according to embodiments of the invention.

FIG. 7B illustrates a process for time gating water sample collection, according to embodiments of the invention. With reference to FIG. 7B, a process commences at a block 752. At a block 754 water sample collection is gated in time utilizing mobile particle data to collect a water sample for bacteria analysis during a peak of mobile particles. At a block 756 water sample collection is gated in time utilizing mobile particle data to collect a water sample for analysis of the mineral and/or metal clogging modality. Mobile particle data are used to gate the collection such that the water sample is taken during a plateau in mobile particle concentration that occurs after the peak in mobile particles. It has been discovered that the ORP and pH measurements are more stable during the plateau in mobile particles. A process stops at a block 758.

Figure 8:
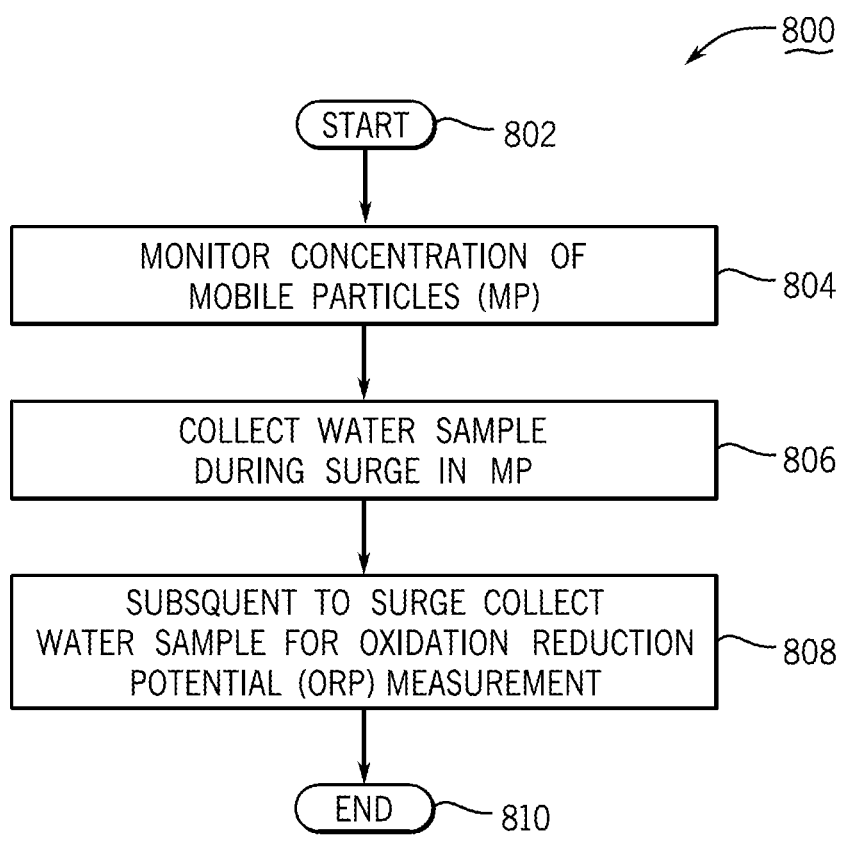
FIG. 8 illustrates a method for obtaining water samples in support of clogging analysis, according to embodiments of the invention.

FIG. 8 illustrates, generally at 800, a method for obtaining water samples in support of clogging analysis, according to embodiments of the invention. With reference to FIG. 8, a process starts at a block 802. At a block 804 mobile particles (MP) flowing in water collected from a well are monitored. At a block 806 a water sample is collected during a surge in mobile particles. Surges in mobile particles are described in FIG. 7A above and below in conjunction with FIG. 9. At a block 808, when a plateau in mobile particles forms, subsequent to a surge, a water sample is collected and is used for ORP and pH measurements. The plateau is used to collect the water sample for the ORP and pH measurement because it has been discovered that the ORP measurement is more stable in the region of the plateau. With respect to ORP and pH measurements there is no clogging specific information lost by collecting a water sample in the region of the plateau. The process stops at a block 810.

Three Well Clogging Modalities

As a well ages, it is generally observed that yield often starts to decrease, this is because one or more of the clogging processes (mobile particles, bacteria growth, and mineral/metal precipitation) eventually become significant enough to impede the flow of water through the local formation/gravel pack and well screen. If pumping rates are left at original design values, the drawdown will increase, thereby lowering a free surface of water in the well moving the free surface closer to the well screen installed in the well. A descending free surface of the water moves oxygenated water closer to the well screen. Oxygenated water can accelerate the second and third clogging modalities as described below, that is, bacteria growth and mineral/metal precipitation out of solution.

(1) Mobile Particle Clogging Modality

With respect to analyzing clogging, in addition to the use of gating water sample collection in time as described above in conjunction with FIG. 7A, FIG. 7B, and FIG. 8, mobile particles provide SCI, such as information on the degree to which a well is purging itself of fine particles in the well gravel pack or nearby aquifer formation when flow from the well resumes from a quiescent state. As described above, a particle counter is used to obtain information on mobile particles. The particle counter provides, as an output, a signal which is representative of data on mobile particles detected, such as a concentration of mobile particles detected. In various embodiments, the particle counter makes sequential measurements in time permitting a plot of mobile particles as a function of time to be assembled from the mobile particle data.

FIG. 9 illustrates plots of mobile particles as a function of time during a well startup transient for two different wells, according to embodiments of the invention. A first well, illustrated at 900, passes mobile particles in an acceptable fashion while a second well illustrated at 950 is experiencing an unacceptable reduction in passage of mobile particles.

A plot of mobile particles is illustrated for the first well at 900. The first well is placed in a quiescent state for a first period of time. Water is not pumped from the first well when the first well is in the quiescent state. A pump attached to the first well is then turned to an ON state thereby pumping a stream of water from the first well. The stream of water flows to a particle counter (such as 710 FIG. 7A) using an apparatus, which is in various embodiments, like the one described above in conjunction with FIG. 7A. The particle counter outputs a signal representative of mobile particles detected, such as a concentration or number of mobile particles measured as a function of time, Such mobile particle data is plotted in 900 with time represented on a horizontal axis 902 and particle count represented on a vertical axis 904. Two separate measurements are recorded at 900, a present measurement indicated at 906 as "count" and an historical measurement indicated at 910 as "previous count." The data displayed in 900 is illustrative of two regions, a first region referred to as a "surge" indicated at 914 and a second region referred to as a "plateau" indicated at 920. The plateau 920 occurs subsequent in time to the surge 914.

For the particular well represented in 900, the surge 914 lasts for less than 8 minutes. A surge peak indicated at 908 for count data 906 and a surge peak at 912 for previous count data 910 are short lived phenomena. Based on the surge peaks, the count has declined approximately 20% relative to the previous count. A 20% decline is a relatively small decline which would not necessarily require any change in the operation of the well at 900.

A plot of mobile particles is illustrated for the second well at 950. Similar to the test performed on the first well, the second well is placed in a quiescent state for a first period of time. Water is not pumped from the second well when the second well is in the quiescent state. A pump attached to the second well is then turned to an ON state thereby pumping a stream of water from the second well. The stream of water flows to a particle counter (such as 710 FIG. 7A) using an apparatus, which is in various embodiments, like the one described above in conjunction with FIG. 7A. The particle counter outputs a signal representative of mobile particles detected, such as a concentration or number of mobile particles measured as a function of time. Such mobile particle data is plotted in 950 with time represented on a horizontal axis 952 and particle count represented on a vertical axis 954. Two separate measurements are recorded at 950, a present measurement indicated at 956 as "count" and an historical measurement indicated at 960 as "previous count." The data displayed in 950 is illustrative of two regions, a first region referred to as a "surge" indicated at 964 and a second region referred to as a "plateau" indicated at 970. The plateau 970 occurs subsequent in time to the surge 964.

For the particular well represented in 950, the surge 964 lasts for less than 8 minutes. A surge peak indicated at 958 (numeric value of approximately 580) for count data 956 and a surge peak at 962 (numeric value of approximately 1400) for previous count 960 are short lived phenomena. Based on the surge peaks, the count 956 has declined approximately 57% relative to the previous count 960. A 57% decline is a significant decline which would result in instructions to modify operation of the well at 950 in order to prevent clogging and to maintain yield.

Note that the peaks of mobile particles illustrated in FIG. 9 last for approximately 8 minutes. The duration of the peak will vary and in some tests the duration of the peak will be less than 8 minutes and in some tests the duration will be greater than 8 minutes. The plots are given by way of illustration only and do not limit embodiments of the invention.

Various particle counters can be used for this analysis leg. A non-limiting example of a particle counter, given only for illustration and with no limitation implied thereby is a Chemtrac PC3400. Comparing particle count plots on the same well, taken at the same pumping rate, and at the same sampling rate (e.g., 100 cubic centimeters/minute) over the same monitored interval post startup from a quiescent state (static condition), but over different timeframes (e.g. months or years), provides a measure of the degree of particle clogging ongoing over the monitored interval. In the example of FIG. 9, "count" represents the current test and "previous Count" represents a test made one year earlier. Note that other sampling rates can be used, the example of 100 cubic centimeters/minute is given by way of example and does not limit embodiments of the invention.

With respect to a given well, measurements of mobile particles are made periodically and are compared against the historical record for the given well. The surge peaks of mobile particles are compared between subsequent measurements to see if a magnitude of a current surge peak in mobile particles is remaining steady with time or is decreasing with time. If the magnitude of mobile particles is decreasing with time, e.g., 14,000 particles year one, 7,000 particles the next year, etc. a mitigation action will be instituted for the particular well. For example, when mobile particles are decreasing year after year, one mitigation action is to start and stop the well pump more frequently than is occurring with the current operation of the well. This action provides a gentile "cleansing" of the formation/gravel pack upon the pump surge and helps to maintain well yield. In other cases, starting and stopping the pump will not be adequate. For example, the local geology around the formation/gravel pack might be high in clay, which can cause clogging of the well screen. Another clogging remediation method is to use a surfactant which is pumped into the well, left to sit for a period of time and is then pumped off. Yet another remediation method is to use a high-pressure jet to clean the well screen and gravel pack of foreign particles. Following each clogging remediation cycle, the particle counter provides useful information on the mobile particles that are dislodged following each cycle. Sometimes many remediation cycles, on the order of dozens, might be needed to bring well yield up to target levels.

Alternatively, if mobile particles are remaining constant over time it can be desirable to stop and start the well less frequently to avoid interruption of service. Thus, mobile particle data is used to inform well operation in order to maximize yield from a well or wells. In some cases, loss of yield due to increased pump stop/start cycling can be offset by a small increase in pumping rate if the particular well has additional pumping rate available relative to its permitted pumping capacity (PPC).

Sometimes, these techniques, e.g., particle counter, surfactants, jet cleaning, etc. can be useful for wells that are installed in problematic geology or poorly constructed wells. Installation of a new well in problematic geology can mimic clogging in an old well.

Well clogging analysis utilizing a "peak" in the surge of mobile particles in the start-up transient from a quiescent state is one metric to use for the mobile particle modality. Alternatively, a quantity of mobile particles can be integrated over a time interval, such as the time interval indicated at 914 in 900 or the time interval indicated at 964 in 950. Mobile particle analysis would proceed through comparison of the number of mobile particles obtained by the integrations over the time interval. Recommendations on changes to operation of a well would be made accordingly. The example of integration of mobile particles over the time interval 914 or 964 is given merely for example. Alternatively, a portion of the interval 914 or 964 can be used for the integration window in time. No limitation is intended by the examples provided herein.

Figure 10:
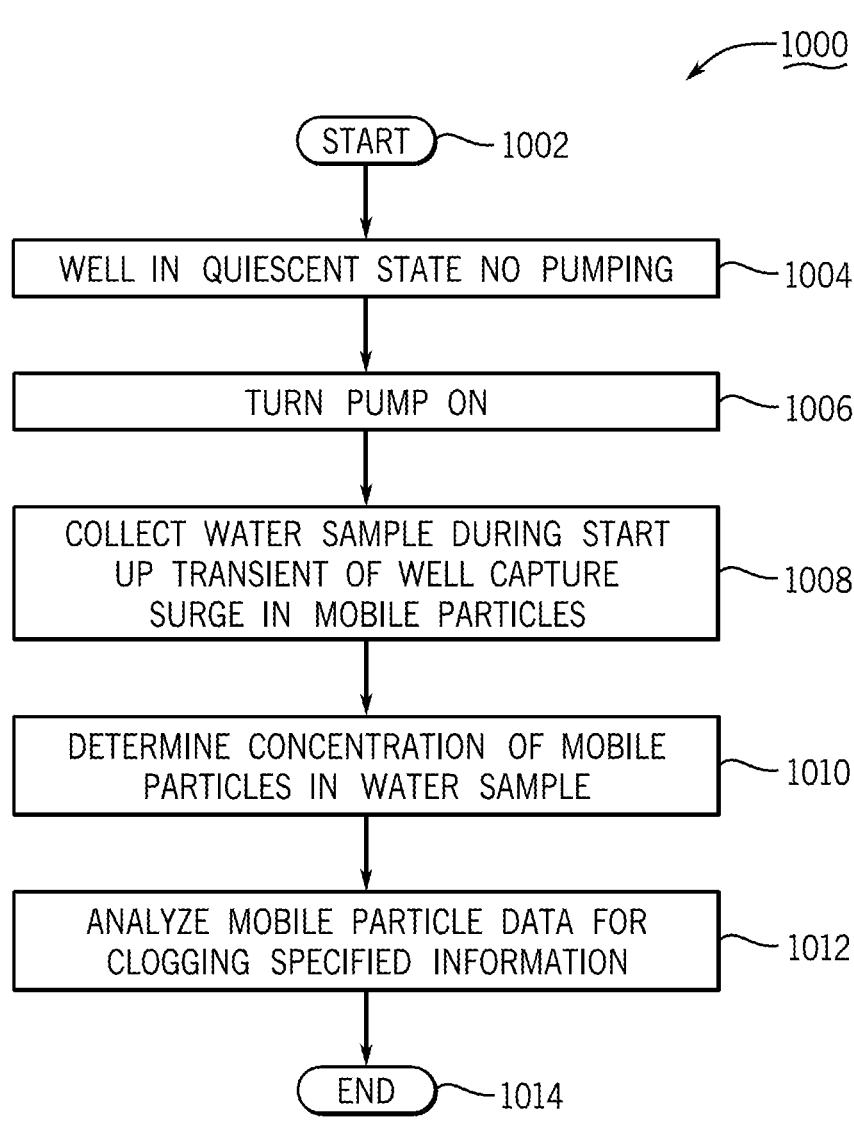
FIG. 10 illustrates a process for obtaining clogging specific information from water samples, according to embodiments of the invention.

FIG. 10 illustrates, generally at 1000, a method for obtaining clogging specific information from water samples, according to embodiments of the invention. With reference to FIG. 10, a process commences at a block 1002. At a block 1004 a well is placed in a quiescent state and maintained in the quiescent state for a first period of time. In the quiescent state water is not pumped from the well. At a block 1006 a pump attached to the well is transitioned to the ON state thereby causing water to transport mobile particles as the water flows through the formation/gravel pack to the particle counter. At a block 1008 a water sample is taken from the well. The water sample is taken during the start-up transient of the well so that the water sample contains clogging specific information such as a surge in mobile particles. In various embodiments, an apparatus such as the one described in conjunction with FIG. 7A is used to support the process described in conjunction with FIG. 10. At a block 1010 a concentration of mobile particles existing in the water sample is determined. In various embodiments a particle counter is used to determine concentrations of mobile particles in the water sample in order to produce mobile particle data in a format such as the mobile particle data illustrated in FIG. 9. In various embodiments, the mobile particle data illustrated in FIG. 9 is input to a data processing system as described below in conjunction with the figures that follow to support creation of a Well Yield Evaluation Worksheet (WYEW), a Well Maintenance Ranking Number (WMRN), and outputs that provide operational instruction for a well.

(2) Bacteria Activity Clogging Modality

Figure 11:
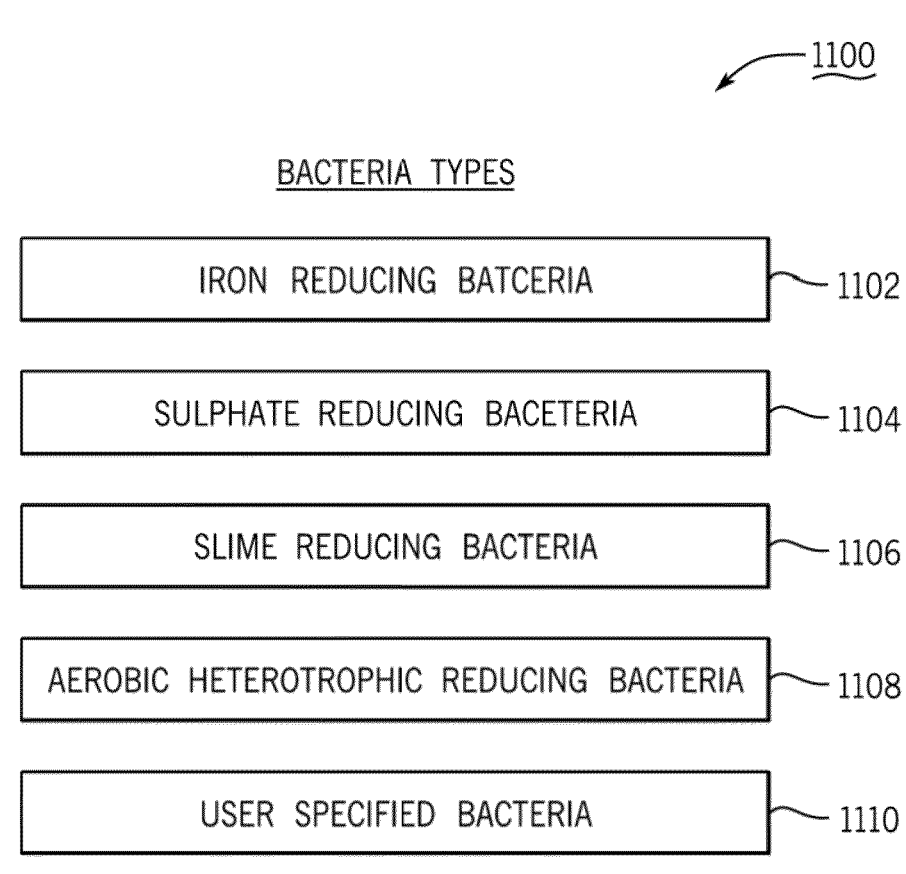
FIG. 11 illustrates major types of bacteria that pose a risk of clogging in a well, according to embodiments of the invention.

As described in FIG. 7A above, a second stream of water is fed into a second analysis process, which is in various embodiments can be accomplished with a bacteria analysis module which is part of the well analysis system. Water is collected for the bacteria analysis module during the peak of mobile particles and is analyzed to determine activity level for different types of bacteria. FIG. 11 illustrates, generally at 1100, major types of bacteria that pose a risk of clogging in a well, according to embodiments of the invention. The major types of bacteria that are of concern include; (1) iron reducing bacteria 1102, (2) sulphate reducing bacteria 1104, (3) slime bacteria 1106, (4) aerobic heterotrophic reducing bacteria (an oxygen consuming bacteria) 1108, and a user specified bacteria at 1110. In various embodiments, Biological Activity Reaction Test (BART) test kits are used for the bacteria activity module. BART kits are used to culture different bacteria types that might be present in the water sample taken from a well. For example, a different BART kit can be used to culture each of the types of bacteria listed on FIG. 11. Each type of bacteria is cultured in its respective BART bottles, thereby permitting the colony to grow so that activity can be assessed in each BART bottle. In one or more embodiments, changes are recorded on a time interval, usually daily, and after approximately 10 days of readings, bacteria activity levels are available for use in the well clogging analysis. In some embodiments, less than 10 days of readings are taken and in other embodiments more than 10 days of readings are taken. 10 days is given by way of example and does not limit embodiments of the invention. Changes in bacteria growth are determined through observation of the colony. Such changes are characterized in different ways. One method of characterization, given merely for illustration but with no limitation implied, is a three-level scale quantized as: (1) non-aggressive, (2) moderate, and (3) aggressive, according to embodiments of the invention. Alternatively, a scale with more than three levels can be used or a scale with less than three levels can be used. In yet other embodiments, bacteria activity can be determined with a light source and light receiver. For example, as a bacteria colony grows in bottle, such as a BART bottle, the colony will obstruct transmission of light through the bottle reducing the amount of light received at the light receiver. A quantization of light reduction can be associated with bacteria activity similar to the observational method described above. Bacteria activity analysis can be setup for a user defined number of levels of quantization.

As described above, the water samples used for the bacteria analysis are collected at the peak of mobile particles that occurs during the well startup transient in order to maximize the specific clogging information (SCI) present in the mobile particles that flow from the formation/gravel pack. Water samples are taken during the surge in mobile particles and are used for bacteria cultures to amplify the populations of bacteria present in the samples. Based on the information obtained from the bacteria cultures that grow in the BART canisters, various remedial actions are taken. Assessing the type(s) of bacteria growing in a well and whether or not the well should be treated for those bacteria are part of the bacteria status modality.

FIG. 12 illustrates, generally at 1200 and 1250, bacteria activity data for two wells, according to embodiments of the invention. With reference to FIG. 12, clogging specific information on a bacteria modality for a first well is illustrated at 1200. Results for a clogging analysis performed on the first well are illustrated at 1202. Within 1202 are the components of chemistry at 1204 and bacteria activity at 1206. A well diagram for the first well is illustrated at 1220. The clogging analysis reveals that bacteria activity levels for all four types of bacteria are very low. After 10 days of culturing in BART bottles there is no discernable activity level for slime bacteria or sulfate reducing bacteria. After 8 days of culturing, aerobic heterotrophic bacteria appears and is quantized as non-aggressive. After 9 days of culturing, iron reducing bacteria appears and is quantized as non-aggressive. The oxidation reduction potential (ORP) measurement is over 300 millivolts (mV) which is reflective of very oxygenated water. However, in this well with low levels of bacteria activity the bacteria clogging modality is not negatively affecting yield.

The well diagram provides an illustration of the static depth to water in the well, pumping level depth to water, the pump setting, and the depths to the well screen or open-borehole interval. For the first well the static depth to water is 9.6 feet; the pumping level depth to water is 77.6 feet, the pump setting is at 78 feet, and the top of the well screen is at a depth of 81 feet. The pumping level depth to water of 77.6 feet is an extrapolated depth to water following the methodology described above using a short 30-minute pumping test. The first well is operating with a flow rate of 1000 gallons/minute which is its permitted pumping capacity. Note that the water cover over the pump is only 1.4 feet and 4.4 feet above the top of the well screen. Such a small distance places the air/water interface for the first well very close to the well screen. It is generally thought that at least 30 feet of water cover is required to prevent the highly oxygenated water from causing well clogging from the bacteria modality. However, these data indicate that bacteria activity is very low and that bacteria modality is not contributing to clogging of the first well. Measurements of well yield for the first well over a period of 6 years indicate that specific capacity has remained high at approximately the maximum level. The first well has remined at its permitted pumping capacity (PPC) over this period of time. The first well is WELL 14 and the second well is WELL A, both of which are discussed further below.

Clogging specific information on a bacteria modality for a second well is illustrated at 1250. Results for a clogging analysis performed on the second well are illustrated at 1252. Within 1252 are the components of chemistry at 1254 and bacteria activity at 1256. A well diagram for the second well is illustrated at 1270. The clogging analysis reveals that bacteria activity levels for the iron reducing type of bacteria and the sulphate reducing type of bacteria are very low. The activity level of the slime type of bacteria is not registering after days of culturing and is therefore very low. However, the aerobic heterotrophic bacteria appears significant during the first day of culturing in a BART bottle. The oxidation reduction potential (ORP) measurement is over 130 millivolts (mV) which reflects an oxygenated state, but less so than the oxygenated state indicated at 1204. Values above 50 mV indicate increased oxygenation of the water which can facilitate bacteria activity.

A well diagram 1250 provides an illustration of the static depth to water in the second well, pumping level depth to water, the pump setting, and the depths to the well screen. For the second well the static depth to water is 64.1 feet; the pumping level depth to water is 89.1 feet, the pump setting is at 108 feet, and the top of the well screen is at a depth of 108 feet. The pumping level depth to water of 89.1 feet is an extrapolated depth to water following the methodology described above using a 30-minute pumping test. The second well has a permitted pumping capacity of 415 gallons/minute, however the specific capacity for the second well was reduced significantly by the bacteria clogging modality necessitating shut down and redevelopment of the second well. Note that the water cover over the pump is 18.9 feet (18.9=108−89.1) which is the same as the water cover above the top of the well screen. Embodiments of the invention directed to a custom extended pump sleeve (CEPS) were applied to the second well during redevelopment in order to restore well yield. The CEPS is described more fully below in conjunction with FIG. 22A and FIG. 23A. Installation of a CEPS has enabled the second well to maintain well yield with the original pump setting depth of 108 feet and the original pumping level depth to water of 89.1 feet even though the pumping level depth to water is 18.9 feet which is less than the industry recommended distance of 30 feet. Through application of the methodology described herein to mitigate the bacteria clogging modality, it is often possible to maintain well yield even in the presence of aggressive bacteria and highly oxygenated water. In instances where the bacterial growth in a well cannot be controlled (has gone unchecked too long) a well replacement is recommended.

Figure 13:
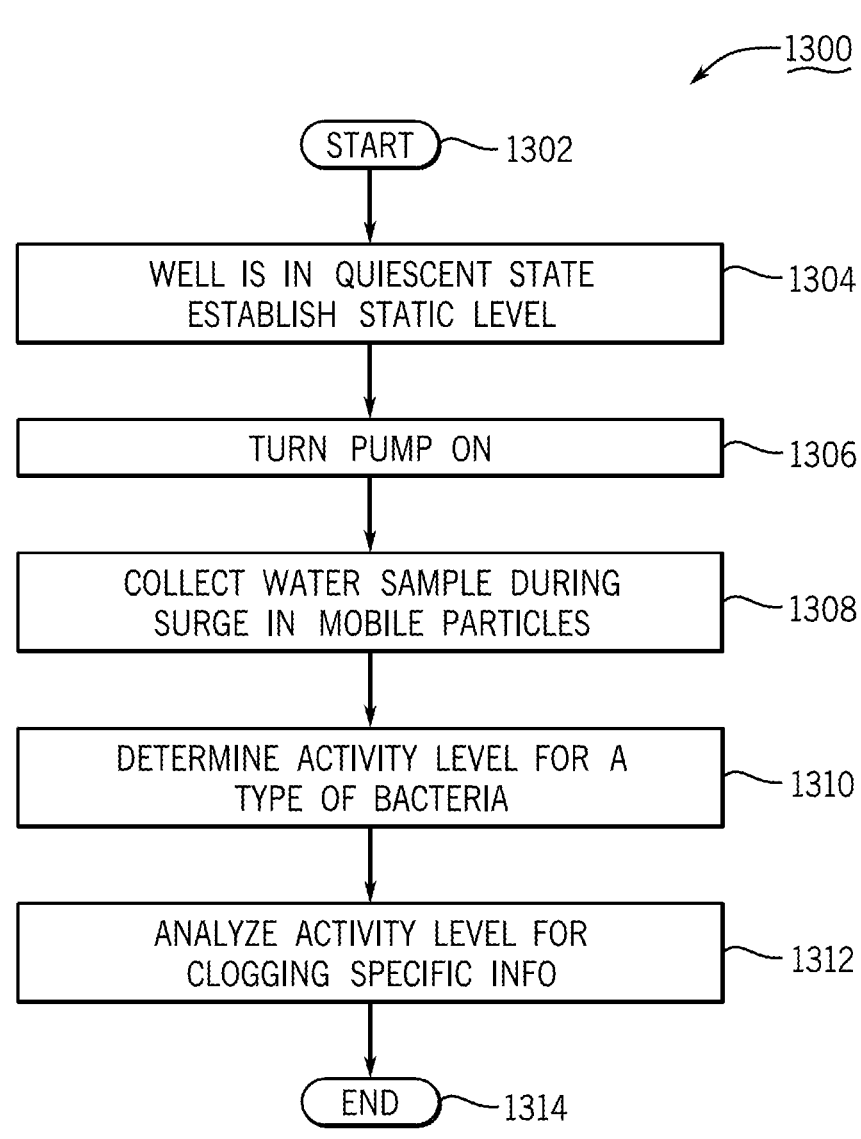
FIG. 13 illustrates a process for obtaining clogging specific information on bacteria activity, according to embodiments of the invention.

FIG. 13 illustrates, generally at 1300, a process for obtaining clogging specific information on bacteria activity, according to embodiments of the invention. With reference to FIG. 13, a process commences at a block 1302. At a block 1304 a well is placed in a quiescent state and maintained in the quiescent state for a first period of time. In the quiescent state water is not pumped from the well. At a block 1306 a pump attached to the well is transitioned to the ON state thereby causing water to transport mobile particles as the water flows through the formation/gravel pack to the particle counter. At a block 1308 a water sample is taken from the well. The water sample is taken during the start-up transient of the well so that the water sample contains clogging specific information which travels in and with the surge in mobile particles. Clogging specific information includes strains of bacteria that break off from the constituent parts of the gravel pack/formation and or well screen and then travel with the surge in mobile particles. In various embodiments, an apparatus such as the one described in conjunction with FIG. 7A is used to support the process described in conjunction with FIG. 13 for the bacteria clogging modality. At a block 1310 an activity level for a type of bacteria found in the water sample is determined. In various embodiments, a bacteria analysis module such as the BART analysis system is used to determine activity levels for types of bacteria that exist in the water sample, thereby facilitating the clogging analysis illustrated in FIG. 13. At a block 1312 the activity level is analyzed with other relevant clogging specific information. The process stops at a block 1314. In various embodiments, the bacteria activity level data and other clogging specific information are input to a data processing system as described below in conjunction with the figures that follow to support creation of a Well Yield Evaluation Worksheet (WYEW), a Well Maintenance Ranking Number (WMRN), and outputs that provide operational instruction for a well.

In various embodiments, a biocide is used to reduce populations of bacteria that have been identified in a given well. Some of these biocides are, but are not limited to, those listed in the following discussion. In a worst case, a remedial action in response to bacteria growth is a redevelopment of the well if bacteria activity levels and other clogging specific information are above a threshold. The second well described above in conjunction with FIG. 12 is an example of well requiring redevelopment. A less severe remedial action is a periodic treatment using a solution (biocide) directed at killing a particular bacteria found during the BART cultures. For example, sodium hypochlorite (SHC) is used for some bacteria. Depending on how high the concentration of bacteria is in a given well, the well is treated either once a year for a well with a lower bacteria activity or twice a year for a well with higher bacteria activity. A treatment cycle consists of adding SHC to the well when the well is in an OFF state. The SHC is left in the well for a period of time, typically overnight and is then pumped off. The treatment with SHC is used to kill bacteria populations, which results in unclogging the well. Start and stopping the well pump can be used in conjunction with the solution to remove mobile particles thereby unclogging or reducing the clogging of the well. Such treatment is undertaken with the purpose of keeping the specific capacity at the design point for the given well.

Alternatively, a solution containing a biocide or acid is used to kill certain types of bacteria when found. Thus, in various embodiments, an appropriate select solution is added to the well, keeping in mind the pH needed to effectively reduce a given type of bacteria. For example, slime bacteria is difficult to kill, therefore, it is important to measure the pH of the water in the well as a first step in order to make sure it is at 2.0 or less before commencing treatment. This is necessary for the added select solution to penetrate the slime "shield" that protects the slime bacteria.

Figure 14A:
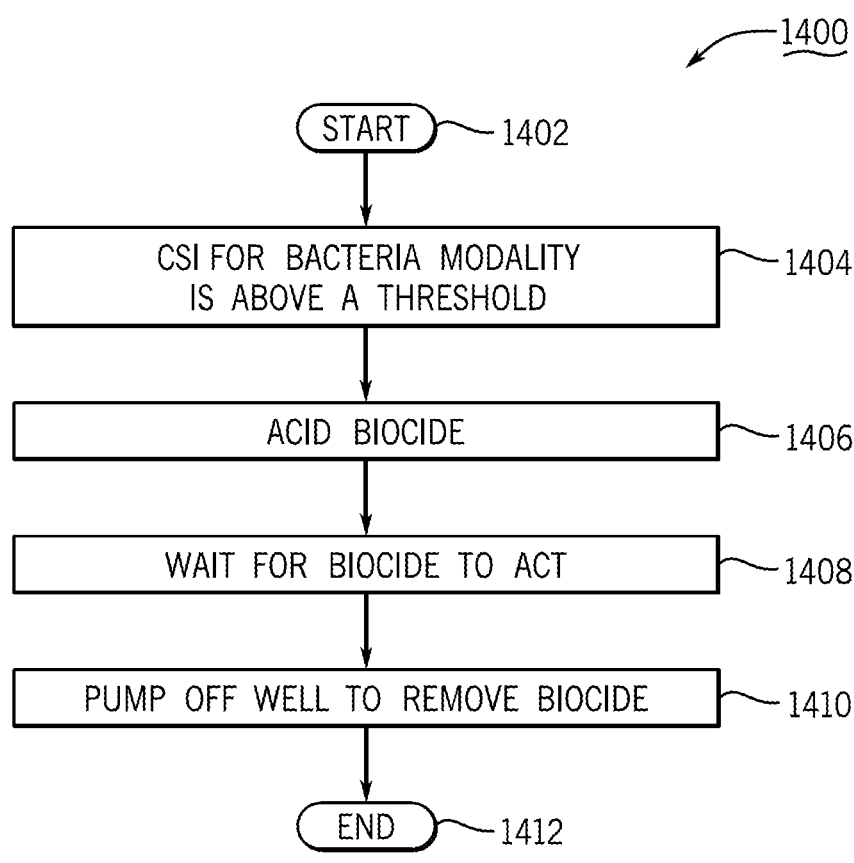
FIG. 14A illustrates a first process for mitigating clogging from bacteria, according to embodiments of the invention.

Sodium hypochlorite, calcium hypochlorite, hydroxyacetic (glycolic) are some of the biocides used in treating bacteria. The basic approach to treating a well for clogging arising from the bacteria modality follows a three-step process once bacteria has been determined to be an operative clogging modality in a given well utilizing the embodiments of the invention described above. FIG. 14A illustrates, generally at 1400, a first process for mitigating clogging from bacteria, according to embodiments of the invention. With respect to FIG. 14A, a process commences at block 1402. At block 1404 clogging specific information (CSI) for the bacteria clogging modality is above a threshold which necessitates treatment. Block 1404 includes analyzing a water sample taken from the well utilizing the process described above including placing the well in a quiescent state for a period of time and then collecting a water sample for bacteria analysis during a surge in mobile particles utilizing a particle counter for time gating the water sample collection. At block 1406 a biocide is added to the well while the well is in an OFF state. In various embodiments a chlorine solution is added to the well as a biocide. Several of the most common forms are Sodium Hypochlorite in a liquid form, Calcium Hypochlorite in a solid, and Hydroxyacetic (glycolic). As the pH rises in the well water the effectiveness of chlorine is reduced. Chlorine enhancers are often used to buffer the pH of the treatment solution and increase the effectiveness of the disinfection. At a block 1408 the treatment solution is left in the well for a period of time sufficient for the biocide to reduce the activity level of the bacteria to an acceptable level. At a block 1410 the well is pumped off to remove the biocide and the bacteria debris which results from bacteria die off. It is often advantageous to subject the well pump to one or more start and stop cycles to facilitate dislodging and removal of debris resulting from the bacteria die off. It can also be advantageous to subject the well screen to high pressure jetting during treatment for bacteria. High pressure jetting can be performed with pressures ranging from approximately 300 psi to approximately 3,000 psi depending on the jetting nozzle used. In some embodiments a solution of sodium hypochlorite in water is applied during the jetting process. Solution concentration of sodium hypochlorite in water can vary, however, a concentration of 100 part per million (PPM) of sodium hypochlorite is used in some applications of jetting. Alternatively, or in addition to jetting, a well screen can be cleaned of bacteria residue through the process of surging the well using surge blocks. The well is surged for a period of time to dislodge bacteria. The process ends at a block 1412.

Following the treatment process to reduce bacteria activity described above, in conjunction with FIG. 14A, a specific capacity measurement is performed on the well utilizing the specific capacity measurement processes described above according to embodiments of the invention. If the specific capacity measurement for the well has returned to an acceptable level then the well is placed back into production. If the specific capacity measurement has not returned to the acceptable level, then the process of FIG. 14A is applied to the well again. The specific capacity measurement process, described above, is applied to the well once again to retest specific capacity until the acceptable level is achieved. In some instances, multiple cycles of biocide application are required to bring the specific capacity up to the acceptable level. In some embodiments a period of time used in block 1408 is approximately a number of hours or overnight. In other embodiments, the period of time used in block 1408 is approximately one or more days. The period of time can be adjusted to provide the biocide a longer time to interact with and to kill the bacteria.

Figure 14B:
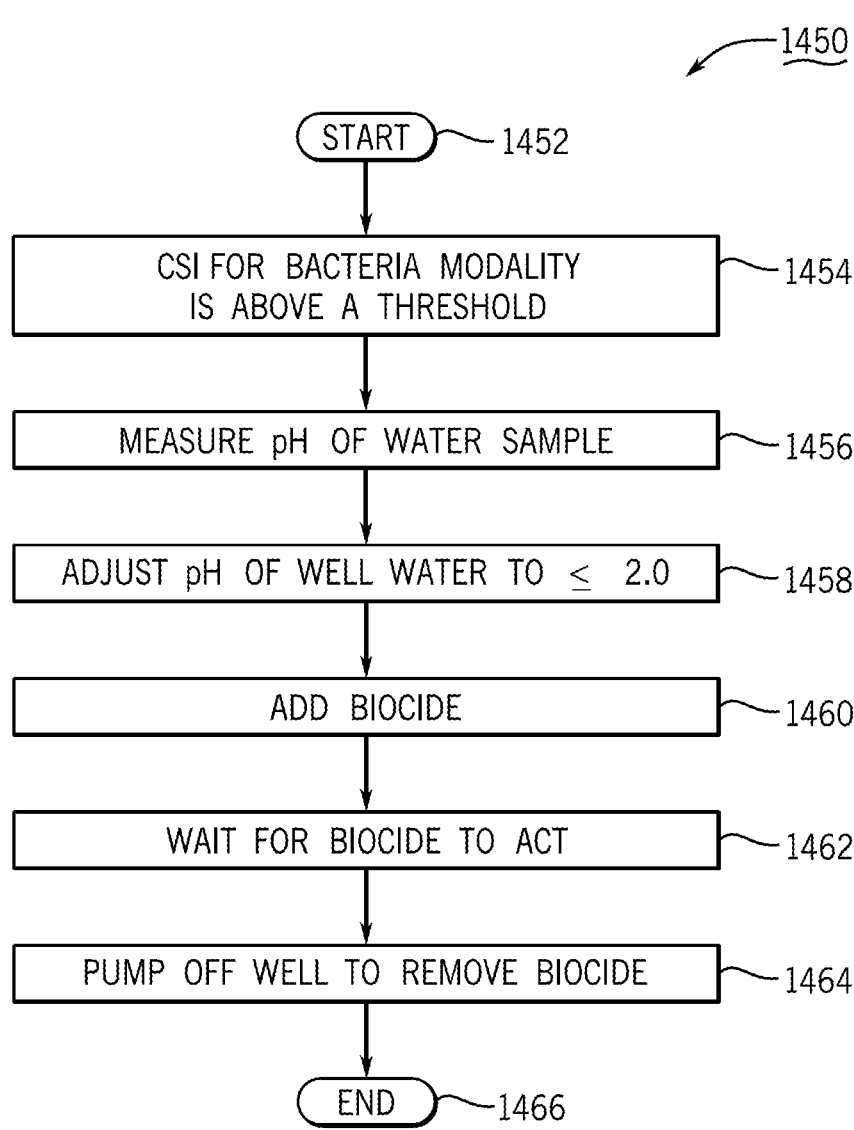
FIG. 14B illustrates a second process for mitigating clogging from bacteria, according to embodiments of the invention.

FIG. 14B illustrates, generally at 1450, a second process for mitigating clogging from bacteria, according to embodiments of the invention. With respect to FIG. 14B, a process starts at a block 1452. At a block 1454 the bacteria modality clogging specific information (CSI) is found to above a threshold which necessitates treatment. Block 1454 includes analyzing a water sample taken from the well utilizing the process described above including placing the well in a quiescent state for a period of time and then collecting a water sample for bacteria analysis during a surge in mobile particles utilizing a particle counter for time gating the water sample collection. At a block 1456 a pH of a water sample taken from the well is measured. At a block 1458 the pH of water in the well is adjusted to a level of approximately 2.0 or less. At block 1460 a biocide is added to the well while the well is in an off state. In various embodiments a chlorine solution is added to the well as a biocide. Several of the most common forms are Sodium Hypochlorite in a liquid form, Calcium Hypochlorite in a solid, and Hydroxyacetic (glycolic). As the pH rises in the well water the effectiveness of chlorine is reduced. Chlorine enhancers are often used to buffer the pH of the treatment solution and increase the effectiveness of the disinfection. At a block 1462 the treatment solution is left in the well for a period of time sufficient for the biocide to reduce the activity level of the bacteria to an acceptable level. At a block 1464 the well is pumped off to remove the biocide and the bacteria debris which results from bacteria die off. It is often advantageous to subject the well pump to one or more stop and start cycles to facilitate dislodging and removal of debris from the bacteria die off. The process ends at a block 1466.

Following the treatment process to reduce bacteria activity described above, in conjunction with FIG. 14B, a specific capacity measurement is performed on the well utilizing the specific capacity measurement processes described above according to embodiments of the invention. If the specific capacity measurement for the well has returned to an acceptable level then the well is placed back into production. If the specific capacity measurement has not returned to the acceptable level, then the process of FIG. 14B is applied to the well again. The specific capacity measurement process, described above, is applied to the well once again and retesting specific capacity until the acceptable level is achieved. In some instances, multiple cycles of biocide application are required to bring the specific capacity up to the acceptable level. In some embodiments a period of time used in block 1462 is approximately a number of hours or overnight. In other embodiments, the period of time used in block 1462 is approximately one or more days. The period of time can be adjusted to permit the biocide a longer time to interact with and to kill the bacteria.

(3) Mineral/Metal Precipitation Modality-Aquifer Chemistry Analysis

Figure 16:
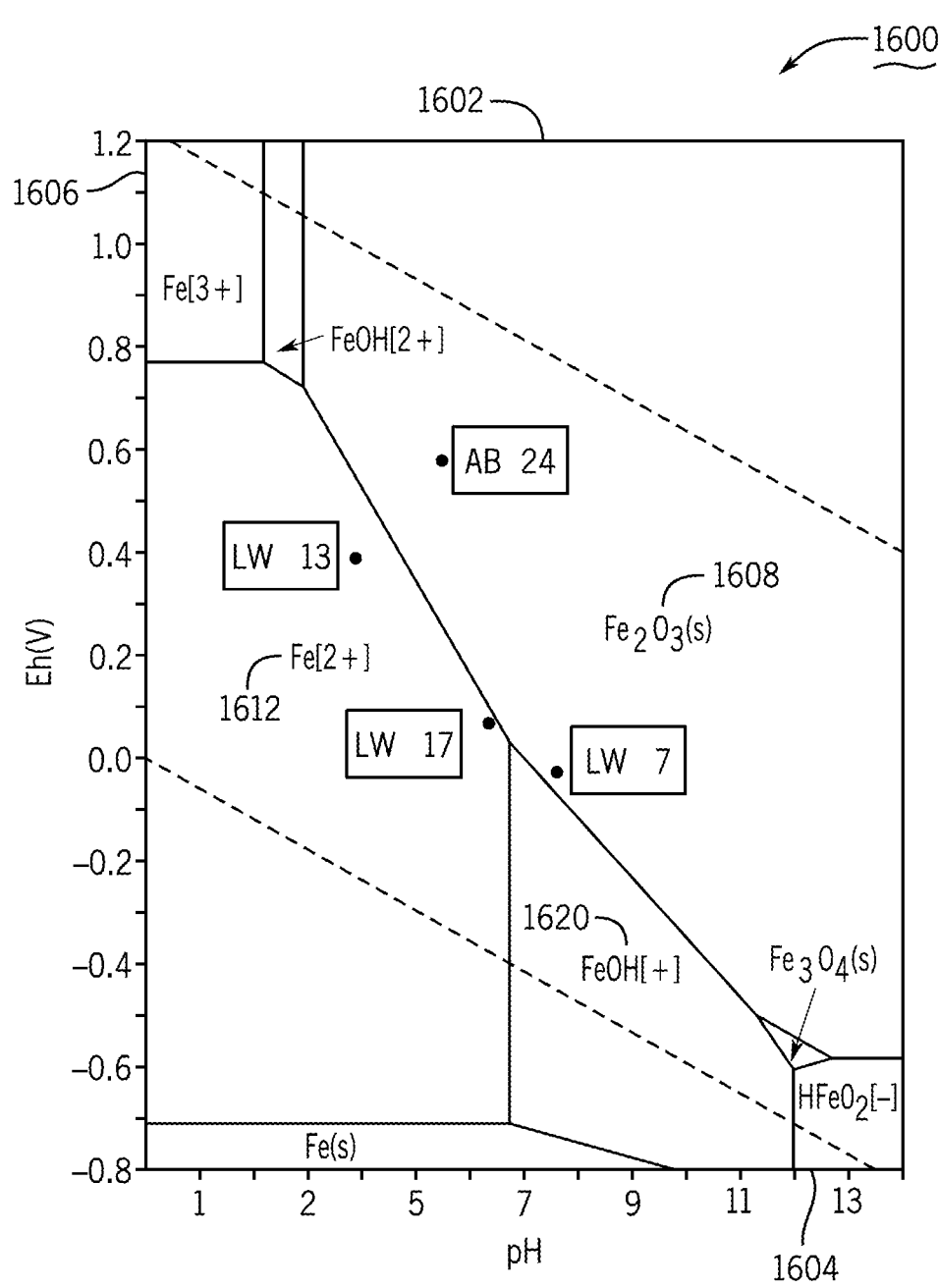
FIG. 16 illustrates an Eh-pH phase diagram for Iron and associated clogging specific information (SCI) for several wells, according to embodiments of the invention.
Figure 17:
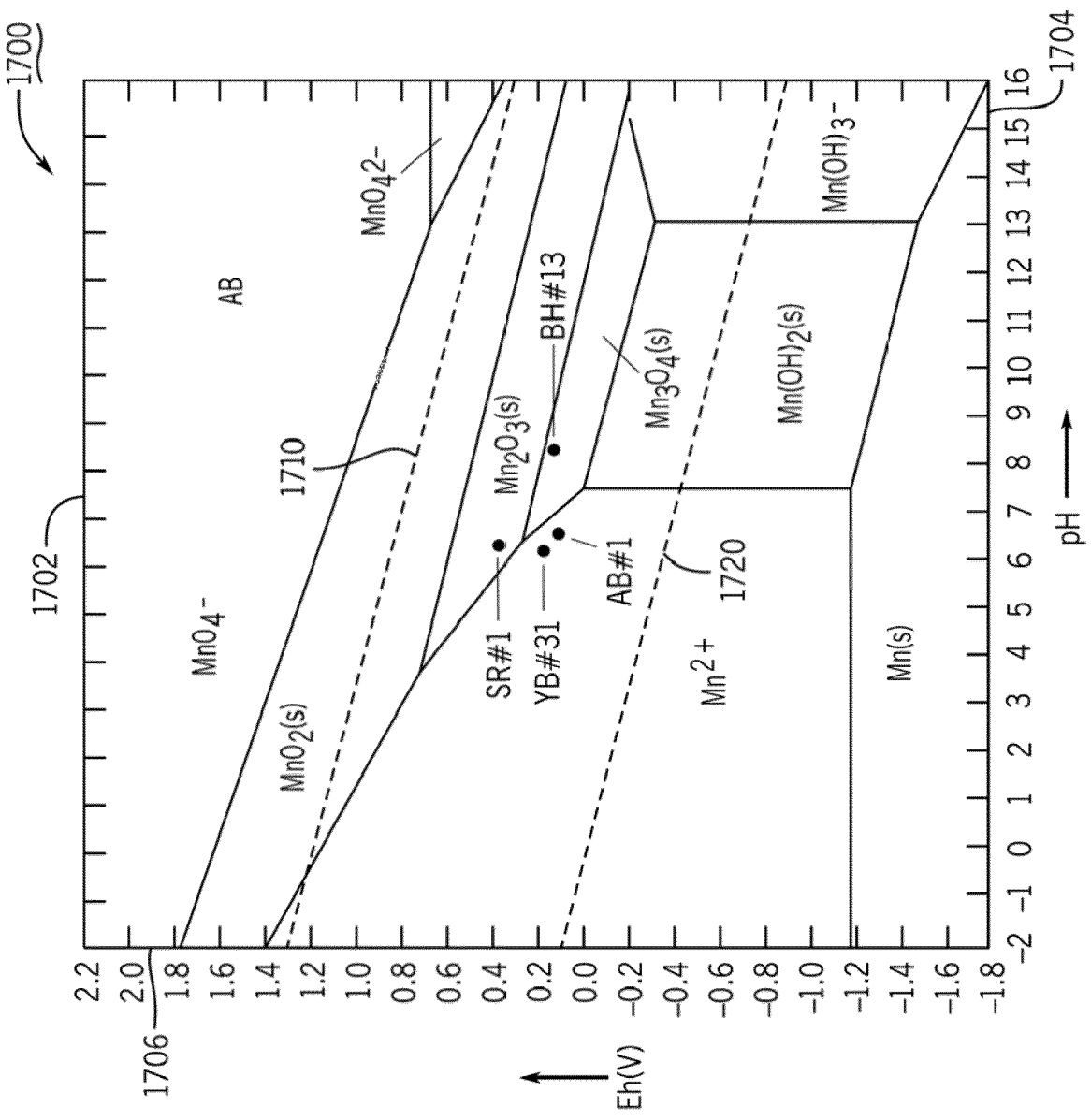
FIG. 17 illustrates an Eh-pH phase diagram for Manganese and associated clogging specific information (SCI) for several wells, according to embodiments of the invention.

As described in FIG. 7A above, a third stream of water is input to a third analysis. The third analysis process is an aquifer chemistry module (ACM), such as 744 (FIG. 7A). The ACM analyzes physical parameters of the water including temperature, conductivity, dissolved oxygen, oxidation-reduction potential or equivalently redox (ORP), and potential of hydrogen (pH). Analysis provided by the ACM conveys information on how likely it is for minerals to precipitate from the aquifer water and thereby contribute to the clogging processes. Eh-pH diagrams are used to quantify the probability of minerals proceeding to precipitate given the aquifer chemistry. A non-limiting example of an aquifer chemistry module, given only for illustration and with no limitation implied thereby, is a model 5913 unit from YSI, Inc. The discussion presented directly below, supporting FIG. 16 and FIG. 17, is directed to diagram(s) of physical properties of particular mineral(s) in the Eh-pH plane or equivalently the ORP-pH plane. These diagrams will be referred to herein as phase diagrams for a particular mineral, such as an Eh-pH phase diagram for Iron. Or equivalently as an ORP-pH phase diagram for Iron. Note that Eh and ORP differ by a constant using the equation (1): $Eh=ORP+K$, where K is a constant applicable to a particular temperature. By definition in art, Eh is a voltage reading made on water using the Standard Hydrogen Electrode (SHE). ORP is a voltage reading using an electrode such as Ag/AgCl or calomel reference electrodes, etc. Often it is not easy to use the SHE in laboratory or field measurements. Instead, an Ag/AgCl electrode is used for ORP measurements and then a conversion factor is applied if it is desirable to convert to Eh. Note that a phase diagram for a mineral in water can also be referred to alternatively as a stability diagram for the mineral in water. No limitation is implied by the use of the term "phase diagram."

Figure 15:
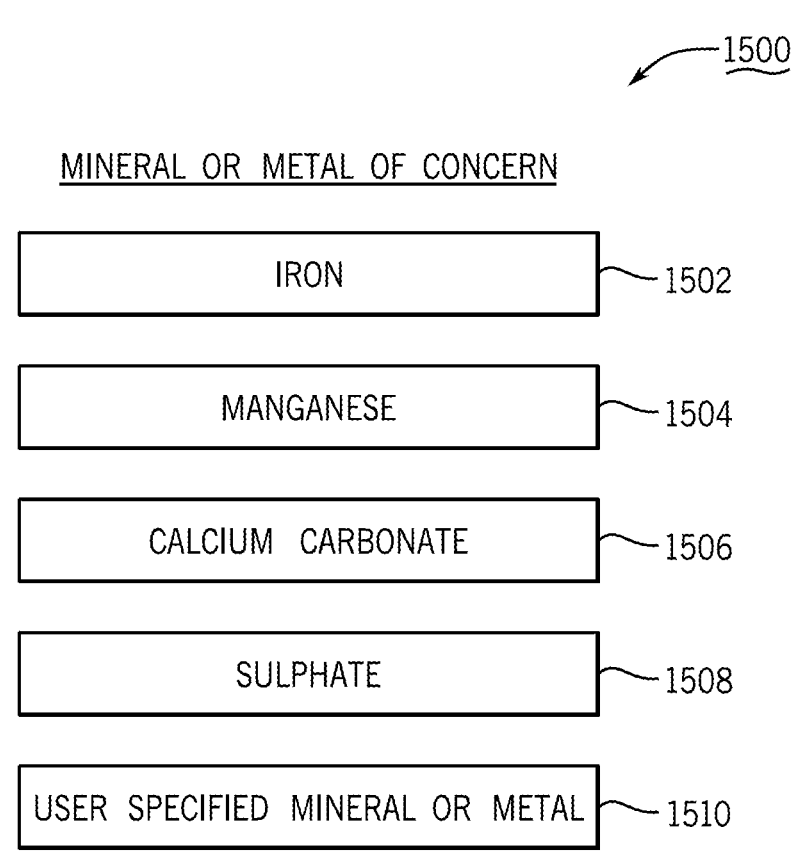
FIG. 15 illustrates a list of minerals whose clogging effects on a well can be mitigated through use of embodiments of the invention.

FIG. 15 illustrates, generally at 1500, a list of minerals whose clogging effects on a well can be mitigated through use of embodiments of the invention. With reference to FIG. 15, relevant minerals include, but are not limited to, iron 1502, manganese 1504, calcium carbonate 1506, sulphate 1508, and a user specified mineral 1510.

Presence of minerals in a given well can be determined in a variety of ways. One way is to analyze a sample of well water for mineral content. Another way is observation of trace amounts of minerals in and around the plumbing associated with a well. Presence of minerals informs the mineral precipitation modality through which a likelihood of precipitation of a particular mineral is estimated.

FIG. 16 illustrates, generally at 1600, an Eh-pH phase diagram for Iron and associated clogging specific information (SCI) for several wells, according to embodiments of the invention. With respect to FIG. 16, a phase diagram for Iron is illustrated at 1602. The phase diagram 1602 is constructed with pH along a horizontal axis 1604 and Eh potential along a vertical axis 1606. Precipitation zones are indicated at 1608 ($Fe_2O_3$(s)) and 1620 (FeOH[+]). Zones 1608 and 1620 are Ferric iron zones. A zone 1612 (Fe[2+]) is more closely aligned with reduced water which tends not to precipitate Iron out of solution. Zone 1612 is a Ferrous Iron zone. Specific clogging information (SCI) consisting of pH and redox measurements are plotted in 1602 for several wells. It has been discovered that when the SCI falls either in the zones 1608 or 1620 or along a border between zone 1612 and 1608 or a border between 1612 and 1620 Iron will precipitate out of solution and deposit on the well screen and/or the formation/gravel pack. When this happens, clogging due to the mineral modality of Iron precipitation is in progress and can reduce well yield. A well plotted as LW 13 and a well plotted as LW 17 are examples of wells that will not precipitate Iron. A well plotted as AB 24 and a well plotted as LW 7 are two examples of SCI that will precipitate Iron. The specific examples of LW 13, LW 17, AB 24, and LW 7 are given by way of example only and do not limit embodiments of the invention. Note that the phase diagram illustrated in FIG. 16 utilizes a scale for Eh on the vertical axis. Alternatively, ORP could have been used for the vertical scale. As described above, when SCI data is plotted on an Eh axis the appropriate conversion factor is applied to an ORP measurement to convert to Eh.

FIG. 17 illustrates, generally at 1700, an Eh-pH phase diagram for Manganese and associated clogging specific information (SCI) for several wells, according to embodiments of the invention. With reference to FIG. 17, the phase diagram 1702 is constructed with pH along a horizontal axis 1704 and Eh potential (Volts) along a vertical axis 1706. A region above a line 1710 indicates oxidized water. A region below a line 1720 is associated with reduced water in which Manganese does not precipitate out of solution. Specific clogging information (SCI) consisting of Eh and pH measurements are plotted for 4 wells at SR #1, BH #13, YB #31, and AB #1.

It has been discovered that when the SCI falls in the zones Mn2+ and $Mn(OH)_2$(s), Manganese does not precipitate out of solution. When SCI falls in the zones indicated by $MnO_2$(s), $Mn_2O_3$(s), and $Mn_3O_4$(s), Manganese will precipitate out of solution and deposit on the well screen and/or the formation/gravel pack. When this happens clogging due to the mineral modality of Manganese precipitation is in progress and can reduce well yield. The SCI plotted in 1702 for wells YB #31 and AB #1 indicate that the wells are not likely to precipitate Manganese. The SCI plotted in 1702 for the wells SR #1 and BH #13 indicate that these wells are likely to precipitate Manganese out of solution. Note that the phase diagram illustrated in FIG. 17 utilizes a scale for Eh on the vertical axis. Alternatively, ORP could have been used for the vertical scale. As described above, when SCI data is plotted on an Eh axis the appropriate conversion factor is applied to an ORP measurement to convert to Eh.

For the other minerals of concern in a well, the corresponding phase diagrams are used in a similar process, as described above for Iron and Manganese, to analyze the CSI from the well to determine whether other minerals are likely to precipitate out of solution thereby contributing to the mineral/metal clogging modality.

Figure 18:
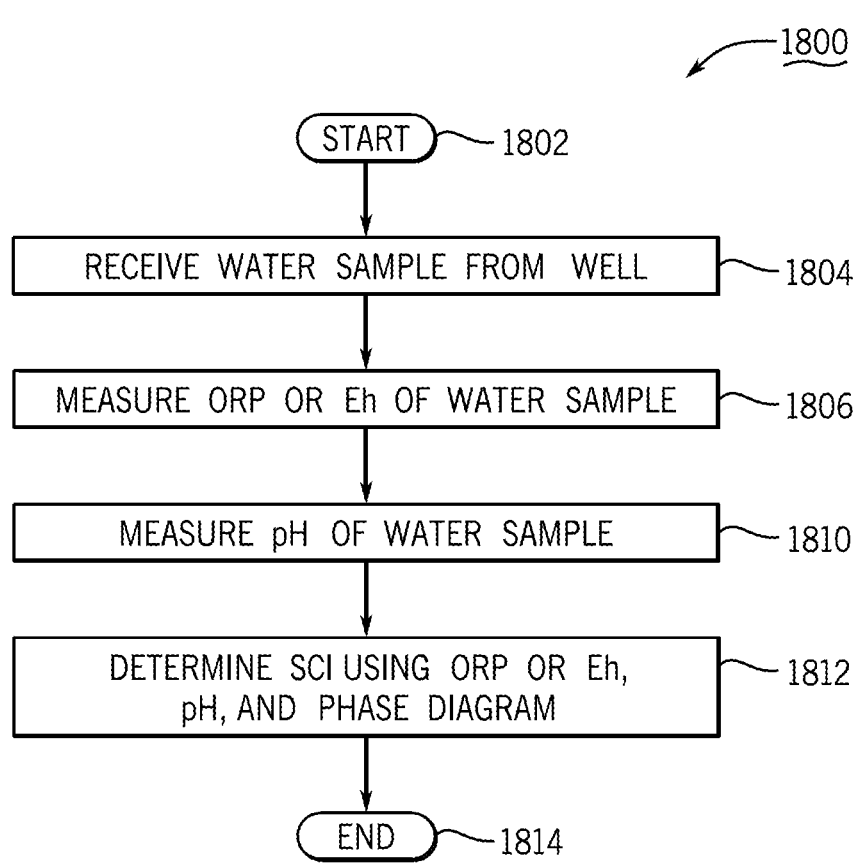
FIG. 18 illustrates a process for assessing clogging potential from a mineral/metal, according to embodiments of the invention.

FIG. 18 illustrates, generally at 1800, a process for assessing clogging potential from a mineral/metal, according to embodiments of the invention. With reference to FIG. 18, a process commences at a block 1802. At a block 1804 a water sample is taken from a well while a pump attached to the well is in an ON state. At a block 1806 an oxidation reduction potential (ORP) measurement is made on the water sample. The ORP measurement process has been observed to produce a more stable reading when the ORP measurements are made during a plateau in mobile particles as described above in conjunction with FIG. 7A and FIG. 9. At a block 1810 a pH measurement is made on the water sample. At a block 1812, clogging specific information (SCI) is determined for the well using the ORP measurement, the pH measurement, and a phase diagram for a mineral or metal. One or more different minerals or metals might be present in a given well. Multiple phase diagrams can be used at the block 1812 to determine likelihoods for the different minerals or metals to precipitate out of solution. The process ends at a block 1814.

As described above, based on outputs from an Aquifer Chemistry Module (ACM), a likelihood of minerals or metals, such as but not limited to, Iron precipitating out of solution can be obtained. Similarly, a likelihood of Manganese precipitating out of solution can be obtained. Calcium carbonates can also precipitate in limestone and dolomitic formations. Under proper conditions, the precipitate forms on the well screen and can close off the openings in the well screen, resulting in clogging of the well and reduction in well yield.

Mineral or metal precipitation onto the well screen is mitigated with the introduction of acid which is used to dissolve the minerals or metals from the well screen thereby restoring well yield. In instances of mineral or metal clogging, acids are used to dissolve the precipitate and thereby restore yield to the well. Dissolving mineral or metal precipitates takes time and has to be sustained under a pH of less than 2, typically for a minimum of an overnight period—but a period of several days is most effective. Typical acids used to reduce mineral precipitation clogging include hydrochloric, sulfuric, sulfamic and malonic. In various embodiment, a treatment using acid for a well includes the following actions on day 1 and day 2.

Day 1—(1) Mix Acid Solution in Tank (pH of 2.0 or less). (2) Tremie the mixture into the well. (3) Collect a water sample and measure pH. (4) Aggressively surge the mixture into the well screen/formation. (5) Periodically monitor pH level. (6) Let stand overnight.

Day 2—(1) Check pH. (2) Surge the well for 4-6 hours. (3) Pump to neutralization tank (do not neutralize in the well). (4) Purge the well until pH and conductivity are normal and discharge is clear.

It can also be advantageous to subject the well screen to high pressure jetting during treatment directed at removing mineral/metal precipitate from a well screen. High pressure jetting can be performed with pressures ranging from approximately 300 psi to approximately 7,000 psi depending on the jetting nozzle used.

Figure 19:
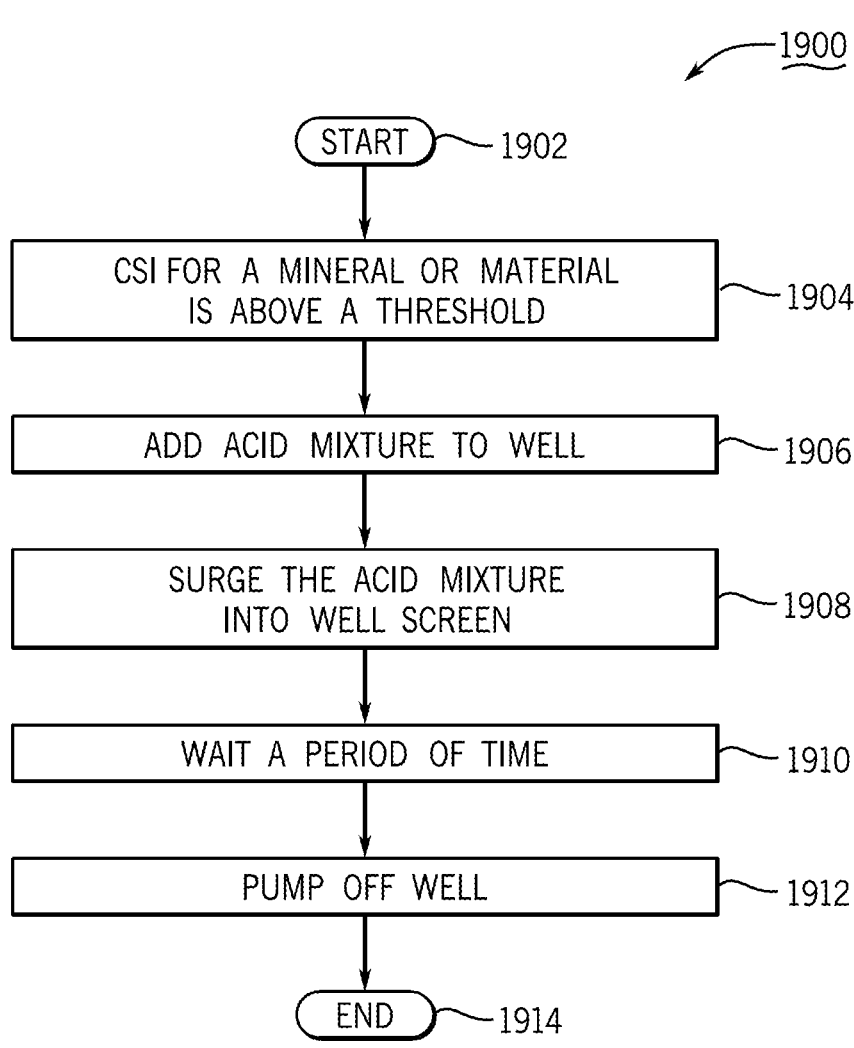
FIG. 19 a first process for mitigating clogging from a mineral/metal, according to embodiments of the invention.

FIG. 19 illustrates a first process, generally at 1900, for mitigating clogging from a mineral or metal, according to embodiments of the invention. With reference to FIG. 19, a process commences at block 1902. At block 1904 the clogging specific information (CSI) for the mineral/metal precipitation modality is above a threshold, as described above, which necessitates treatment. At block 1906 an acid mixture is added to the well while the well is in an OFF state. Several different acids, such as but not limited to, hydrochloric acid, sulfuric acid, sulfamic acid, malonic acid, and a user specified acid can be used in the acid mixture. At a block 1908 the acid mixture is surged into the well screen. In various embodiments the surging can last for a time specified by a user. In some embodiments the surging continues for 4 to 6 hours. At a block 1910 the treatment solution is left in the well for a period of time sufficient for the acid solution to dissolve/loosen the mineral/metal precipitate from the well screen. In various embodiments the first time can be approximately 12 hours. At a block 1912 the well is pumped off to waste to remove the acid mixture. It can also be advantageous to subject the well screen to high pressure jetting during treatment following the block 1910. High pressure jetting can be performed with pressures ranging from approximately 300 psi to 7,000 psi depending on the jetting nozzle used. At a block 1914 the process ends.

Figure 20:
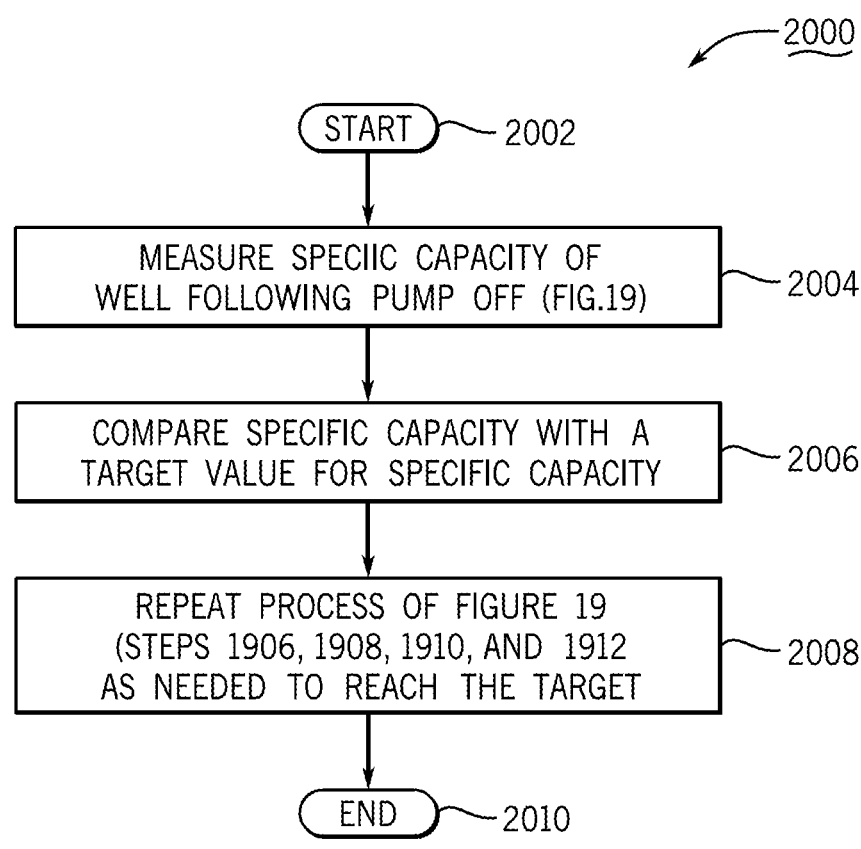
FIG. 20 illustrates a second process for mitigating clogging from a mineral/metal, according to embodiments of the invention.

FIG. 20 illustrates, generally at 2000, a second process for mitigating clogging from a mineral/metal, according to embodiments of the invention. With reference to FIG. 20, a process commences at a block 2002. Following the treatment process to reduce mineral/metal precipitate described above, in conjunction with FIG. 19, at a block 2004 a specific capacity measurement is performed on the well utilizing the specific capacity measurement processes described above according to embodiments of the invention. At a block 2006 the measured specific capacity measurement from the block 2004 is compared with a target specific capacity for the well. If the measured specific capacity for the well has returned to an acceptable level (target level) then the well is placed back into production. If the measured specific capacity has not returned to the acceptable level, then at a block 2008 the process of FIG. 19 is applied to the well again. The Specific Capacity measurement process, described above, is applied to the well once again to retest specific capacity until the target level is achieved. In some instances, multiple cycles of acid mixture application are required to bring the specific capacity of the well up to the acceptable level.

Figure 21:
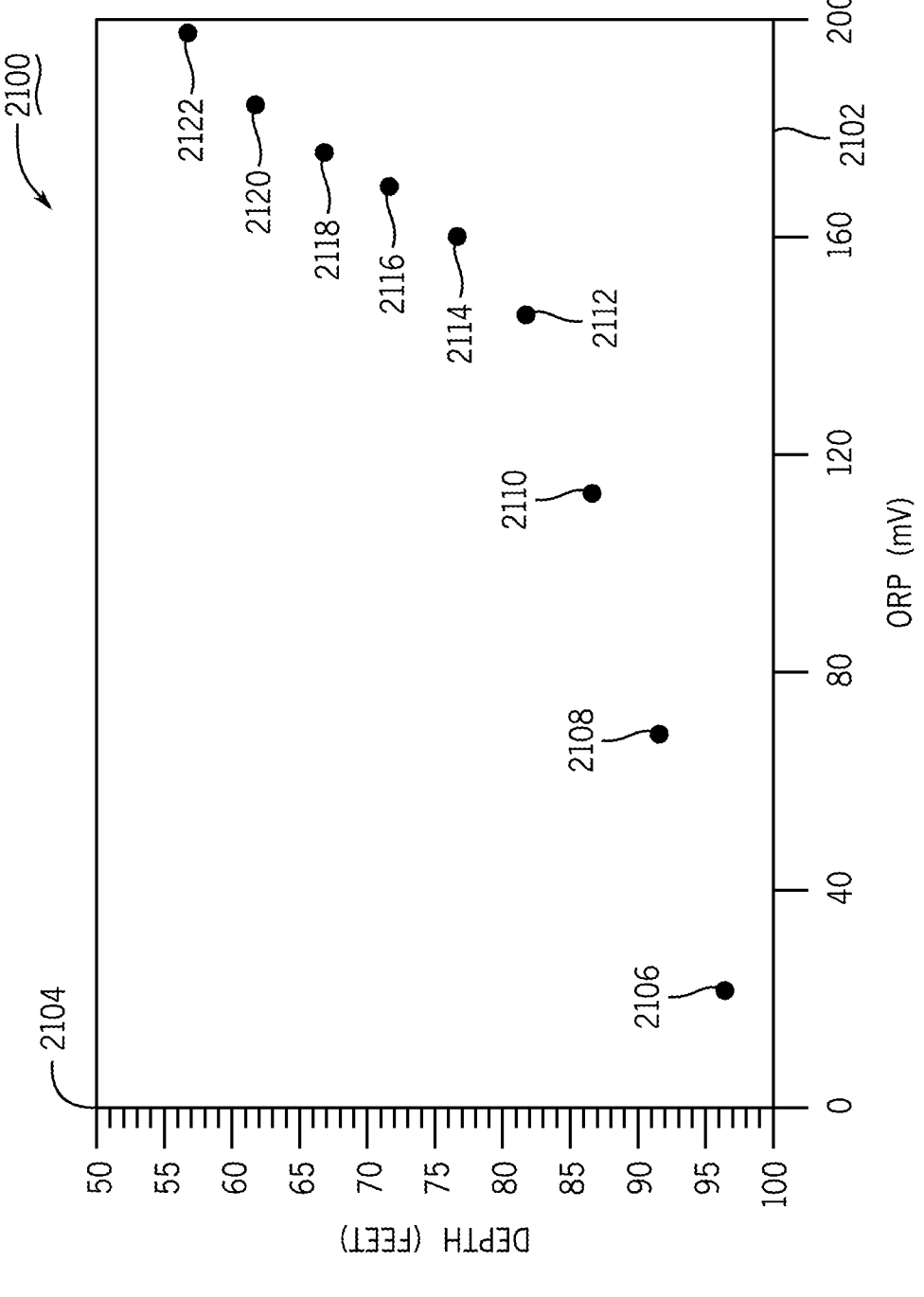
FIG. 21 illustrates an oxidation-reduction potential (ORP) profile as a function of depth into a well, according to embodiments of the invention.

Precipitation of minerals or metals is also accelerated when there is too much dissolved oxygen in the water proximate to the well screen. FIG. 21 illustrates, generally at 2100, an oxidation-reduction potential (ORP) profile as a function of depth into a well, according to embodiments of the invention. With reference to FIG. 21, ORP data is plotted on a graph with a horizontal axis representing ORP (mV) and a vertical axis representing depth into a well. The ORP data (2106, 2108, 2110, 2112, 2114, 2116, 2118, 2120, and 2122) increase from a minimum value at 2106, occurring at a maximum depth, to a maximum value at 2122, occurring at a minimum depth.

Air is in contact with the free surface of the water in the well casing. Thus, at the free surface of the water, the water in the well is exposed to atmospheric oxygen which creates an oxygen gradient that penetrates into the water column in the well casing and extends at lower concentrations down through the water to the location of the well screen at the entrance to the aquifer. It has been discovered that excessive drawdown of the free surface increases the concentration of dissolved oxygen in the water, even at the depth of the well screen, which can promote both mineral or metal precipitation as well as bacteria growth on the well screen and in the formation/gravel pack adjacent to the well screen, all of which can contribute to clogging the well. Therefore, as a practice, it is desirable to avoid drawing the free surface of water in the well down to the immediate vicinity of the top of the well screen, because the goal is to avoid increasing the concentration of oxygen in the water at the depth of the well screen. As described above, various bacteria can grow in response to the presence of the oxygen. Historical practice, to minimize bacteria growth, has been to keep a water level at least 30 feet above the well screen in order to keep the concentration of dissolved oxygen sufficiently low in the vicinity of the top of the well screen. However, even if this 30-foot criteria is maintained, oxygen introduced from the air/water surface can still present a cause of clogging by facilitating bacteria growth. In other instances, water demand from a given well might require a pumping rate that causes a free surface to be drawn down to approximately the top of a well pump with the well pump set just above the top of a well screen. Such a situation presents a high level of oxygen to the air/water interface making clogging likely. Embodiments of the invention can be used to mitigate this problem.

Mitigation of Clogging Related to Oxygen Installation and Use of a Custom Extended Pump Sleeve (CEPS)

High levels of dissolved oxygen present in the water at a depth of aquifer extraction i.e., generally an upper region of a well screen can be mitigated through the use of a custom extended pump sleeve (CEPS) according to embodiment of the invention. It has been discovered that methods of mitigating the clogging modalities of bacteria growth and mineral/metals precipitation is to use a CEPS to effectively lower a location of a pump's water collection port down into the region of the well screen, e.g., even to within approximately several feet of the bottom of the well screen.

Figure 22A:
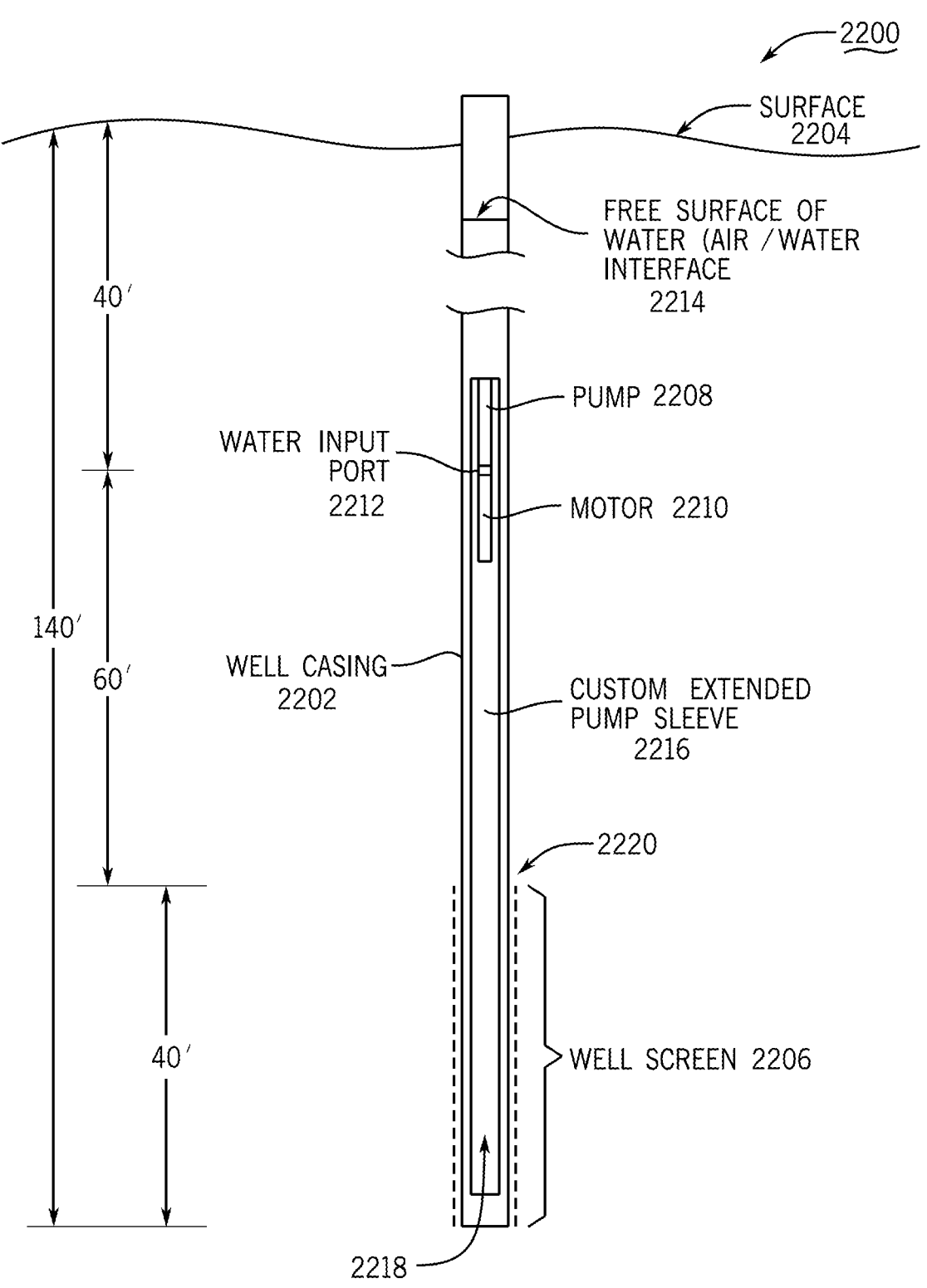
FIG. 22A illustrates a custom extended pump sleeve (CEPS) to draw water principally from a lower portion of a well screen, according to embodiments of the invention.
Figure 22B:
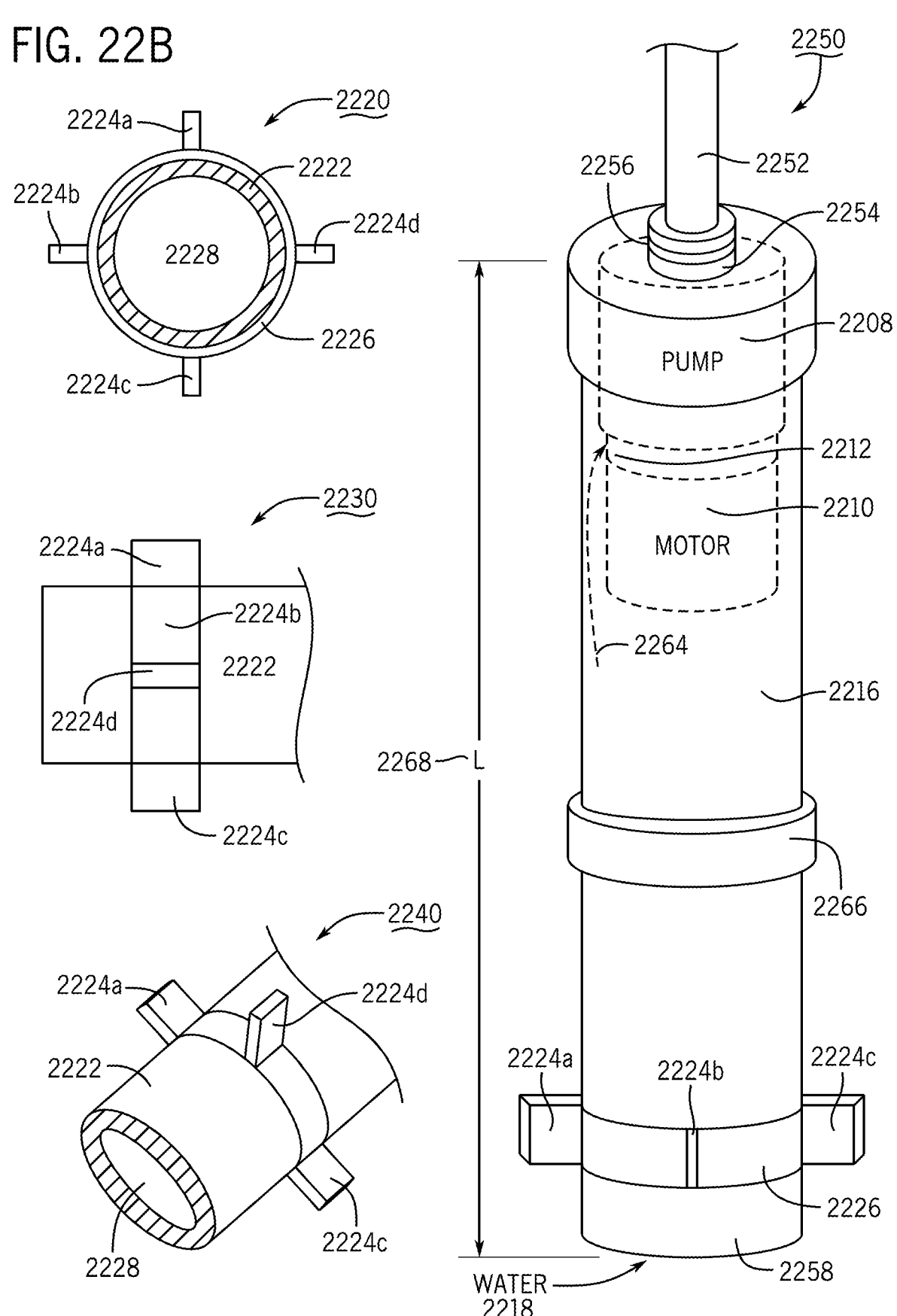
FIG. 22B illustrates a centralizer used in conjunction with a Custom Extended Pump Sleeve (CEPS), according to embodiments of the invention.

FIG. 22A illustrates, generally at 2200, a custom extended pump sleeve (CEPS) to draw water principally from a lower portion of a well screen, according to embodiments of the invention. FIG. 22B illustrates a centralizer used in conjunction with a Custom Extended Pump Sleeve (CEPS), according to embodiments of the invention. Referring to FIG. 22A and to FIG. 22B collectively, a cross-sectional view of a well installed with a CEPS is illustrated. A well has been installed below a surface of the ground 2204 as shown. The well is defined by a well casing 2202 and a well screen 2206. As is typical for (sand and gravel constructed) water wells, a well pump 2208 is located above and fastened to a pump motor 2210 to form a pump/motor assembly. A closeup view of the CEPS is illustrated at 2250.

Assembly of a CEPS proceeds when the pump/motor assembly is out of the well. A CEPS 2216 is tightly fitted to the pump/motor assembly at a point above the water inlet 2212. In various embodiments, the CEPS has a collar 2254 that attaches to a pump riser pipe 2252 with a device such as a rubber sleeve and fastening band 2256. One example of fastening the collar 2254 to the pump riser pipe 2252 is with use of a Fernco coupling. In various embodiments, the CEPS is an elongate tube-like structure that fits within a well casing. Pipe is an example of an elongate tube-like structure. When the CEPS is made with pipe, the manufactured collar 2254 is designed to accept a pipe section. One or more pipe sections are joined together using one or more unions, one of which is illustrated at 2266, to provide a length 2268 sufficient to place a bottom end 2258 of the CEPS close to a bottom of the well screen 2206. When plastic pipe, such as for example, polyvinyl chloride (PVC) pipe is used to construct a CEPS, sections of PVC pipe can be either threaded or glued together using one or more couplings or unions 2266. In vertical turbine pump applications, the CEPS would only fit over the pump portion of the pumping assembly in the well.

In some embodiments, the toe (or bottom) 2258 of the CEPS 2216 is centered in the well screen area (near the base of the well screen) by means of a device referred to as a centralizer. A centralizer can be made from a material such as stainless-steel or plastic. The centralizer is a fabricated device intended to locate the toe of the CEPS in the proximate center (with respect to the cylindrical cross section of the well screen), ultimately preventing the sleeve from laying against the well screen and thereby blocking water flow into the well. In particularly crooked wells or CEPS having a length of over 50 feet, a centralizer just above the screen section 2206 may be necessary. Thus, more than one centralizer can be installed on a CEPS.

A bottom view of a centralizer installed on a CEPS is illustrated at 2220. In various embodiments, a centralizer has a band 2226 with legs 2224*a*, 2224*b*, 2224*c*, and 2224*d*. An end of the CEPS is indicated at 2222. The band 2226 is configured to attach to the CEPS 2222, with mechanical fasteners. Alternatively, legs can be made of PVC plastic attached to a CEPS with glue. An interior of the CEPS is indicated at 2228. Water flows into interior 2228 as indicated at 2218. A side view of the centralizer is illustrated at 2230 and an isometric view is illustrated at 2240. Legs 2224*a*, 2224*b*, 2224*c*, and 2224*d* can be made with a variety of shapes. For example, square, rectangular, circular, etc. While four legs have been depicted in the figure, in various embodiments less than four legs can be used. In some embodiments three legs are used. Legs can be solid or legs can be made in the form of a compliant structure such as bands of material formed into a shape such as circular, oval, etc. The compliance of the bands softens interaction with an inside of a well casing or well screen.

The distance that a CEPS extends down into a well screen area is determined based on a given well's individual characteristics, such as but not limited to pumping rate, screen diameter, screen length, screen slot size, and clogging specific information. In some embodiments, the CEPS 2216 extends down to the bottom the well screen 2206 causing water to enter the bottom of the CEPS 2216 as shown at 2218. Water is drawn up through the CEPS via the pump/motor assembly causing water to enter the pump inlet 2212 as illustrated by a flow of water at 2264. In various embodiments, the CEPS is constructed with a material such as plastic (PVC for example) and is designed with an inside diameter large enough to fit over the pump/motor assembly. The inside diameter of the CEPS should provide a sufficiently large annular space between the outer diameter of the pump/motor assembly such that the required well yield volume flow can pass without creating turbulent flow in the annular space.

Note that without the CEPS 2216, water is drawn by the well pump 2208 from a point between a bottom of the pump 2208 and the top of the motor 2210 indicated as water input port 2212, causing a majority of water to be drawn from a top 2220 of the well screen 2206. Hydraulic loss calculations of the well screen are such that when the pump 2208 is traditionally set at or above the top 2220 of the well screen 2206 without the use of a CEPS, the input port of the pump 2212 (midway between the pump and motor in submersible pumps) produced a hydraulic loss across the well screen such that and there is approximately 3 times as much water flowing out of the formation/gravel pack over the upper most foot of well screen than flows from the lowest foot.

As an example, a typical municipal production well can be 140 feet deep with 40 feet of well screen at the bottom. A pump/motor unit at a depth of 40 feet is 60 feet above the top of the well screen. The pump's water input port is located midway between the motor and the pump. Thus, water is drawn from the aquifer principally from the 100 foot depth (top of the well screen).

In order to draw water from, effectively the "bottom" of the well, a 95-foot-long CEPS is installed over the pump which moves the effective water input port to within 5 feet of the well bottom. When fitted with a CEPS as described in conjunction with FIG. 22A, a reversal occurs. In this scenario, hydraulic loss calculations indicate that there is approximately three times more water flowing out of the lowest foot of aquifer formation at the 140-foot depth than flows from the aquifer at the 100-foot depth. In essence, the CEPS is used to draw water from deeper in the well which means that the water flowing out of the formation/gravel pack is further away from the free surface in the well. The free surface of water in the well casing is the location of the air/water interface from which atmospheric oxygen enters the water column. Thus, with a CEPS installed; water is principally drawn from the aquifer at a depth of approximately the bottom of the well screen even though the pump remains at its original setting of forty (40) feet down from the surface.

The CEPS serves two purposes: 1) to increase separation between the air/water interface and the location along the pump screen where a majority of the water leaves the aquifer, and 2) it can capture water of lower ORP values (see FIG. 21). Thus, water is drawn from the aquifer in an area where the oxygen concentration in the water is lower because of the increased separation distance obtained with the use of the CEPS. The lower oxidation-reduction potential of the deeper groundwater keeps minerals or metals in solution so that they do not precipitate onto the well screen and or system piping-hence reducing clogging processes.

As illustrated in FIG. 21, the increase in oxygen from the bottom to the top of the aquifer is evident in the graph illustrated in 2100. Water at the base of the aquifer (at a depth of approximately 96 feet) has an ORP value of around 20 millivolts (mV), whereas water at the top of the well screen (at a depth of approximately 56 feet) has an ORP value of around 200 mV. The CEPS allows the well to take more reduced water (lower dissolved oxygen content) from the base of the aquifer, than from the top, as currently occurs with a standard pump set at the top of a well screen. Drawing more reduced water from deeper down in the aquifer has the following benefits: (1) The naturally occurring metal oxides (typically Iron and Manganese) in the ground water are more likely to stay in solution rather than precipitate out, which helps reduce the potential for clogging the well screen and gravel pack; and (2) There is less bacterial growth in the well screen, thus reducing the potential for clogging.

Figure 23A:
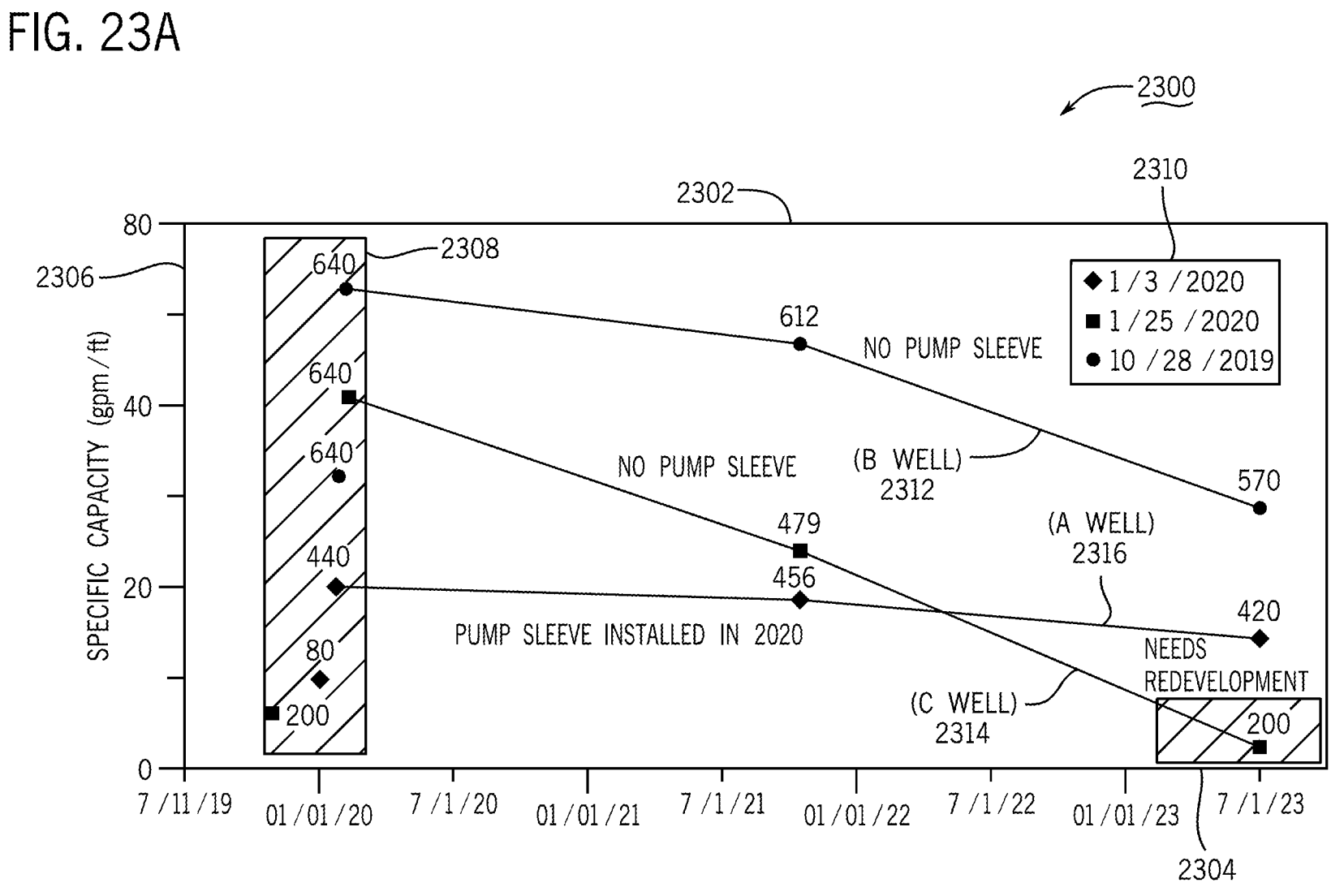

Use of a CEPS has effectively "reversed" the water column by allowing the pump to draw a majority of water from the bottom rather than the top of the water column. The CEPS is designed such that it does not reduce well specific capacity During pumping, water is principally flowing out of the formation or formation/gravel pack from nearer the "bottom" of the well, i.e., the lowest region of the well screen instead of the top of the well (which is where water flows from when a CEPS is not used). In other words, a CEPS is used to capture groundwater with oxidation-reduction potential (ORP) lowered significantly enough to mitigate precipitation of minerals or metals onto the well screen/gravel pack and associated system piping. Thus, well yield is maintained for a longer time than would be expected for a shallow well not fitted with a CEPS as described above. Those of ordinary skill in the art will realize that short pump sleeves (several feet long) are sometimes used to facilitate cooling the pump motor. Such short pump sleeves increase water flow velocity across the surface of the motor housing by drawing water from the bottom of the motor housing thereby increasing cooling of the motor. This historical use of short pump sleeves for cooling is very different from the use described herein with CEPS. Short pump sleeves that provide motor cooling do not cause reversal of the water column as described above. In other words, a short pump sleeve does not accomplish what the CEPS accomplishes because of the short pump sleeve's short length. An example of the effectiveness of the CEPS over time is illustrated in FIG. 23A for three wells, Well A, Well B, and Well C. FIG. 23A illustrates, generally at 2300, a comparison of well yield with and without use of a CEPS, according to embodiments of the invention. With reference to FIG. 23A, specific capacity is plotted for 3 shallow wells in similar geologic setting within the same wellfield. All three wells have similar well details. The plot 2302 is constructed with time along a horizontal axis 2304 and specific capacity along a vertical axis 2306 and data key at 2310. Specific capacity is estimated for these wells using the procedure of extrapolation to a pumping level at 3 days as described above in a previous section according to embodiments of the invention. All 3 wells were redeveloped in late 2019 or early 2020. The improvement in specific capacity directly following the three redevelopment efforts can be seen in the striped vertical box in the figure at 2308. These data illustrate that the wells had relatively effective hydraulic efficiencies at the start of the pump sleeve trial period.

Well A, whose specific capacity data is illustrated at 2316 suffered substantial loss of yield necessitating redevelopment. The bacteria modality of clogging for this well, illustrated and described above at 1250 in FIG. 12, was aggressive aerobic heterotrophic bacteria activity. At the time of redevelopment, the well was experiencing clogging from the bacteria clogging modality and the mineral/metal precipitation clogging modality. Well A is a shallow well with the bottom of the well screen at 128 feet, the top of the well screen at 108 feet, the pump setting at 108 feet, and the pumping level at 89.1 feet, all of which are illustrated at 1250 in FIG. 12. Note that Well A would have had 18.9 feet of water cover above the top of its well screen without installation of the custom extended pump sleeve (CEPS), calculated as follows: 18.9'=108'−89.1'. After installation of a 15-foot-long CEPS, Well A now has 33.9 feet of water cover above the bottom of the CEPS calculated as follows: 33.9'=(108'−89.1')+15'. The 15-foot-long CEPS was installed in 2019 post-redevelopment which placed the water intake of the CEPS at a depth of 123 feet which is 5 feet above the bottom of the well. Thus, "reversing" the water column with respect to withdrawal of water from the aquifer. As described above in conjunction with FIG. 21 and FIG. 22A the CEPS lowers the principal depth zone of the aquifer over which water extraction occurs (aquifer extraction zone). Thus, with installation of the CEPS, Well A has increased water cover over the aquifer extraction zone. Well A has a permitted pumping capacity (PPC) of 415 gpm (gallons/minute). At the end of the time period illustrated in 2302 the pumping rate was at its PPC.

Well B has the bottom of the well screen at a depth of 130 feet, the top of the well screen is at 94 feet, the pumping level is at 67.7 feet, and the pump setting is at 82 feet. Thus, Well B has 26.3 feet of water cover above the top of the well screen, i.e., 26.3'=94'−67.7'. Well B has a permitted capacity of 950 gpm. At the end of the time period illustrated in 2302 the pumping rate had been reduced by 375 gpm to maintain water cover.

Well C has the bottom of the well screen at a depth of one hundred and thirty-five (135) feet, the top of the well screen is at 95 feet, the pumping level is at 75.4 feet, and the pump setting is at 90 feet. Thus, Well C has 19.6 feet of water cover above the top of the well screen, i.e., 19.6'=95'−75.4'. Well C has a permitted capacity of 700 gpm. At the end of the time period illustrated in 2302 the pumping rate had been reduced by 103 gpm to maintain water cover.

Specific Capacity for Well B is illustrated at 2312 and the specific capacity for Well C is illustrated at 2314. Well B and Well C did not, as noted in the plot of 2302, receive a CEPS. Both Well B and Well C are relatively shallow wells with well details discussed above which are similar to Well A. From these data, it is evident that over the 4 years since well redevelopment, Well A has generally sustained its yield at 2316, yet lost some 25% of its specific capacity. Whereas Well B at 2312 has lost some 11% of its yield but around 45% of specific capacity. Well C at 2314 has lost some 69% of its yield and nearly 95% of its specific capacity. In fact, Well C is yet again scheduled for redevelopment in only 4 years of operation since the prior redevelopment.

Note that both Well B and Well C (without CEPS) draw a majority of their water from an upper portion of the aquifer which has highly oxygenated water as illustrated in FIG. 21 (higher ORP at shallow depth and lower ORP at greater depth). Without a CEPS there has been no modification of the aquifer extraction zone and the redeveloped wells are destined to experience continued reduction in yield. The CEPS has accomplished what has not been previously possible in shallow wells. In other words, installation of a CEPS enables extended yield for a shallow well which is sensitive to the second and third clogging modalities with less than 30 feet of water cover over a top of a well screen. Note that the actual water cover over the top of the well screen for Well A is 18.9 feet. These results illustrate the usefulness of a CEPS in maintaining sustainable yields in shallow well settings.

Figure 23B:
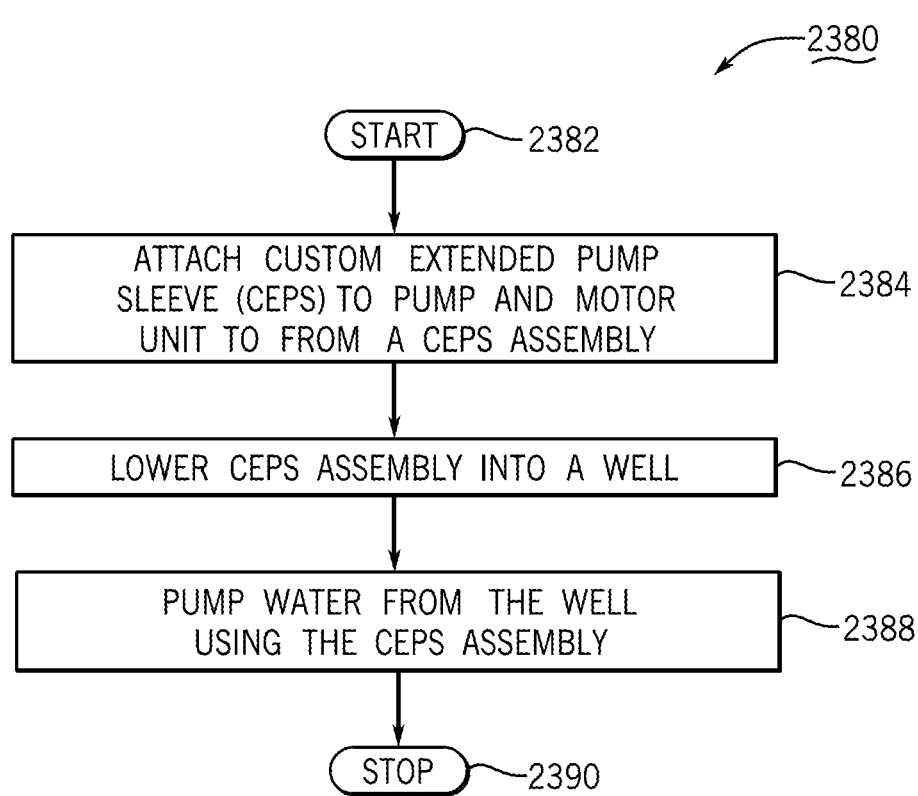
FIG. 23B illustrates a process for using a Custom Extended Pump Sleeve (CEPS), according to embodiments of the invention.

FIG. 23B illustrates, generally at 2380, a process for using a Custom Extended Pump Sleeve (CEPS), according to embodiments of the invention. With reference to FIG. 23B, a process commences at a block 2382. At a block 2384 a CEPS is attached to a pump and motor unit to form a CEPS assembly. In some embodiments one or more centralizers are part of the CEPS assembly as described above. At a block 2386 the CEPS assembly is lowered into a well. At a block 2388 water is pumped from the well using the CEPS assembly to provide a reversal of the water column as described herein. The process stops at a block 2390.

Dewatering

Another situation has to do with excessive oxygen migration into aquifer water in shallow wells during dewatering episodes that can result from stopping and starting pumping. In such situations, when the air/water interface is drawn down, due to pumping, atmospheric oxygen comes into contact with the inner surface of the well casing, essentially saturating the surfaces with oxygen. When the pump is shut off, the water level in the well casing rises rewetting the inner surface of the well casing that was just exposed to atmospheric oxygen. This dewatering process introduces oxygen into the aquifer when the water level in the well is close to the well screen, as in the case with shallow wells. Repeated stop/start dewatering cycles introduce more oxygen into the aquifer. In such a situation, the course of action for mitigation will be to minimize stop/start cycles, i.e. maintain constant pump operation.

Thus, in some situations, for example, if a well is precipitating iron, it is best to run the well pump as long as possible without starting and stopping the pump. This mode of operation minimizes introducing oxygen into the aquifer through start/stop dewatering cycles. Iron, Manganese, and Carbonates are the most common minerals/metals that are analyzed for with regard to precipitation and well clogging.

Some of the information obtained from the aquifer chemistry module (ACM) are used in the analysis framework to obtain: (1) how long to run the pump; and (2) at what flow rate to run the pump based on drawdown constraints presented from the considerations at work in situ within a given well. Or a CEPS can be installed as described above to "reverse" the water column thereby drawing more reduced water from a bottom of the well screen instead of a top of the well screen, as described above. In various embodiments, a CEPS can be combined with a modification to well pump operation to introduce even less oxygen into the aquifer, the combination can prolong time to the next well maintenance event. Thereby saving money while maintaining yield over what would be attained without employing embodiments of the invention described herein.

Aquifer Depletion—Reduction in Yield

As noted above, the three modalities of clogging can contribute to reduction in specific capacity and ultimately a reduction in well yield. Apart from the three modalities of clogging, an independent cause of loss of yield is reduction in the static water level of an aquifer, this can be referred to in the art as aquifer depletion. FIG. 24 illustrates a reduction in static water level of an aquifer and the effect on well yield, according to embodiments of the invention. With reference to FIG. 24, a water level record 2402 for an aquifer is illustrated in 2400. A corresponding well yield record 2452 for a well that draws water from the aquifer is illustrated in 2450.

The water level record 2402 presents static depth measurements plotted as a function of time with time on a horizontal axis 2406 and static depth to water on a vertical axis 2408 with the well in the OFF state. A first series of measurements is indicated at 2410. A second series of measurements is indicated at 2412. Note at the outset that the second series of depths 2412 is nominally 10 feet below the first series of depths 2410. In other words, the static level of the aquifer has fallen by 10 feet.

The well yield record 2452 is a plot of specific capacity measurements plotted as a function of time on the horizontal axis at 2456 and specific capacity is plotted along a vertical axis at 2458. A maximum specific capacity for this well is indicated by a reference line at 2460. An 80% of maximum specific capacity reference line is indicated at 2462. A 50% of maximum specific capacity reference line is indicated at 2464. Specific capacity measurements are created for this well using the processes and systems previously described above where a depth to water is extrapolated to a future time (nominally 3-Days using a mathematical model with empirically obtained data to predict aquifer transmission) based on a short pumping test (nominally 30 minutes), according to embodiments of the invention. Accordingly, a first specific capacity measurement is plotted at 2470, this value is at the maximum value for the well. A second measurement of specific capacity 2472 was made a number of months subsequent to 2470. The second value 2472 is less than 2470. A third measurement of specific capacity 2474 was made a number of months subsequent to 2472. The third value 2474 is less than 2472. The 2474 value is less than 80% of the maximum specific capacity for the well. The data illustrated in 2452 illustrates a decline in specific capacity for the well.

Some of the relevant well details for this well are its permitted pumping capacity is 500 gpm, its production pumping has been reduced to 313 gpm in order to maintain a pumping level of 54 feet, and the pump setting is at 55 feet. A yield of 313 gpm represents a loss of 37.5% relative to the well's permitted pumping capacity of 500 gpm. 37.5%= ((500–313)/500)×100.

Analysis of the water level record 2402 and the well yield record 2452 reveals that the loss of yield from 500 gpm to 313 gpm and specific capacity reduction from approximately 24.5 gpm/ft to 18.5 gpm/ft (due to clogging), as well as a loss of available well draw down caused by aquifer depletion. Precise and repeatable specific capacity measurements provide the ability to distinguish between the potential causes of loss of yield operative in a given well as demonstrated above by utilizing embodiments of the invention.

Well Evaluation Framework

In one or more embodiments, a well evaluation framework or equivalently a well analysis framework is taught. The well analysis framework is applied to individual wells and then a group of individual wells is analyzed collectively. The well analysis framework utilizes the specific capacity measurements and estimates thereof based on extrapolated pumping times to create well yield records as a function of time for a given well (embodiments of which are described above); time gating of water sample collection from a well utilizing a particle counter to support multi-modal clogging analysis and well chemistry analysis (embodiments of which are described above); compilation of water level records over time for an aquifer the well resides in, and analysis of the foregoing to provide findings and recommendations for future operation of the well. The findings and recommendations are directed to maintaining well yield by addressing the individual component causes that are causing well yield to decrease. The analysis framework includes capturing and presentation of well data that is used to assess, establish, and address the causes of loss of yield that are occurring in a given well. These causes include the causative modalities of well clogging as well as changes in the aquifer.

Over a period of time, a baseline of well data is acquired, through tests that are repeated for a given well or wells. The data are analyzed, and the analysis framework identifies wells in need of either treatment, redevelopment, or replacement due to declining yield. The analysis framework ranks a well according to the most expedient time frame for maintenance (such as treatment, mechanical alterations, operational alternations, redevelopment and/or replacement) with the goal of achieving long-term sustainable yields. The analysis framework facilitates quantifiable budget projections for well field operation and enables operational efficiency of a well field to be optimized.

Well Yield Evaluation Worksheet (WYEW)

The well evaluation framework, described directly above, is supported by Well Yield Evaluation Worksheets (WYEW). If a group of wells is under evaluation, then a WYEW is created for each well in the group. WYEWs are described in the figures that follow.

Figure 25:
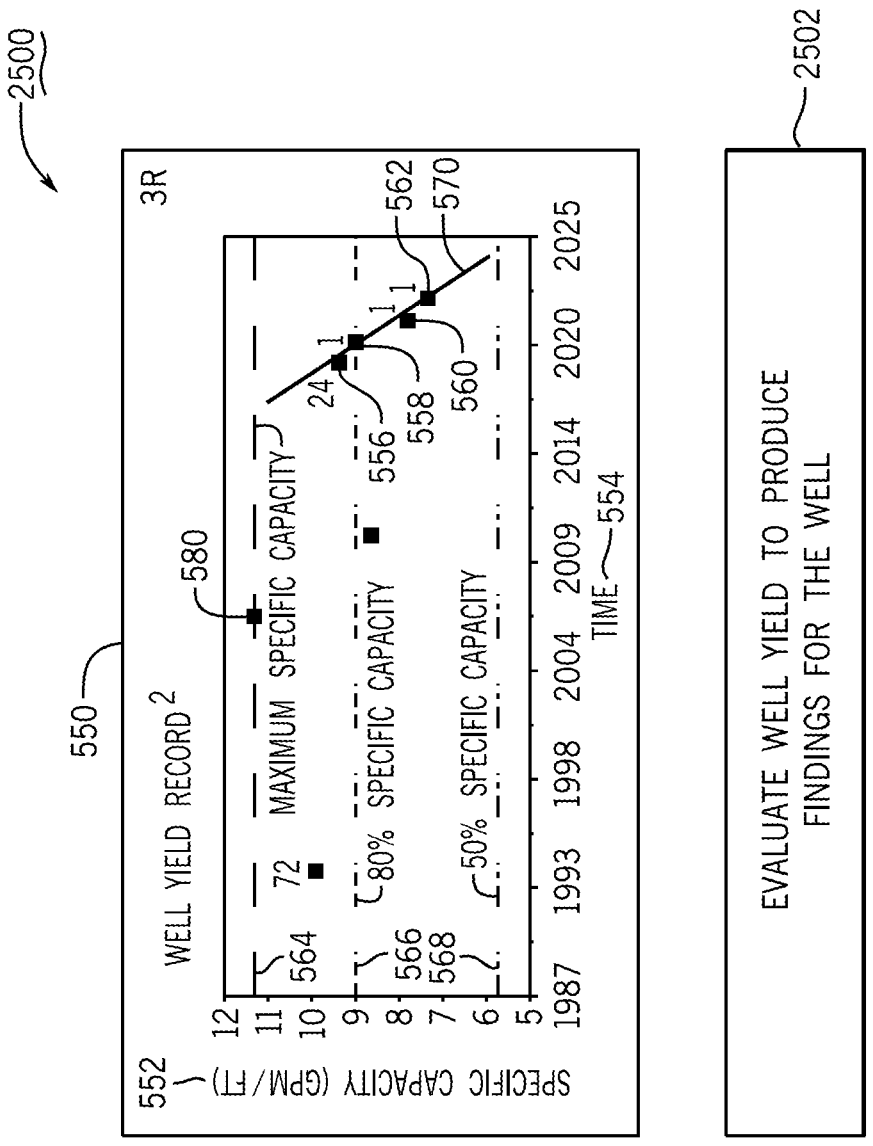
FIG. 25 illustrates a well yield evaluation worksheet (WYEW), according to embodiments of the invention.

FIG. 25 illustrates, generally at 2500, a well yield evaluation worksheet (WYEW), according to embodiments of the invention. With reference to FIG. 25, the well yield record described in FIG. 5 is illustrated again as an example of its use in a WYEW. The well yield record 550 provides a record of well yield 552 over the time period shown at 554. An evaluation of well yield occurs at 2502. The evaluation includes analysis of the behavior of specific capacity over time. Based on the evaluation of well yield, for example the declining specific capacity indicated at 570, findings are produced for the well. While the most recent specific capacity measurement at 562 is above the 50% reduction threshold of specific capacity 568 present yield does not need to be reduced. However, the declining specific capacity triggers recommendations to support future yield. In various embodiments, a WYEW can be generated with the well yield record 550 and findings for presentation to a user in various media, such as but not limited to, media for hardcopy such as paper, data file for storage on computer readable media, graphics file for display, etc.

Figure 26:
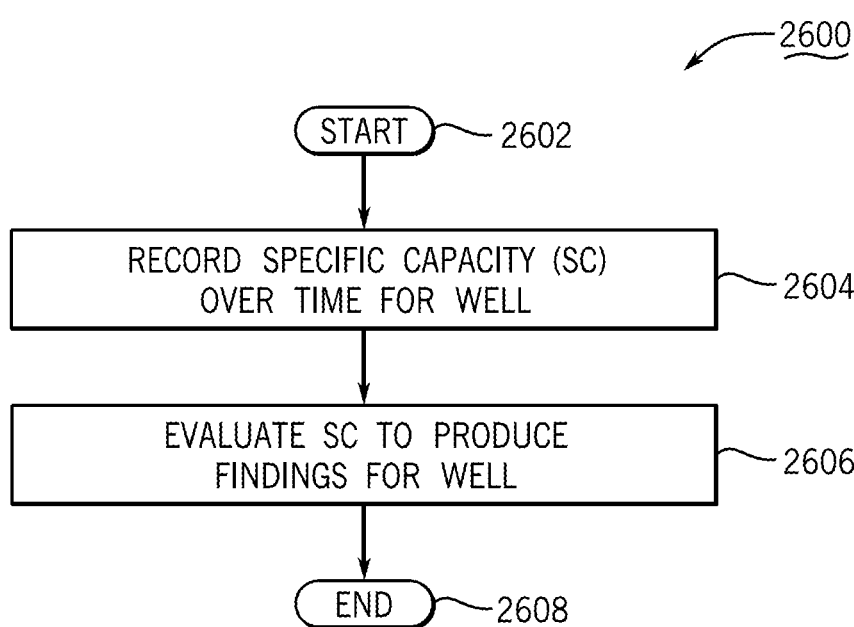
FIG. 26 illustrates a process for creating a well yield evaluation worksheet (WYEW), according to embodiments of the invention.

FIG. 26 illustrates, generally at 2600, a process for creating a well yield evaluation worksheet (WYEW), according to embodiments of the invention. With reference to FIG. 26, a process commences at a block 2602. At a block 2604 a record of specific capacity is made over a period of time as described above in conjunction with embodiments of the invention utilizing depth to water extrapolated to future pumping times based on pumping tests that occur for a first period of time. At a block 2606 the specific capacity data from the block 2604 are evaluated to produce findings the well. The process ends at a block 2608.

Figure 27:
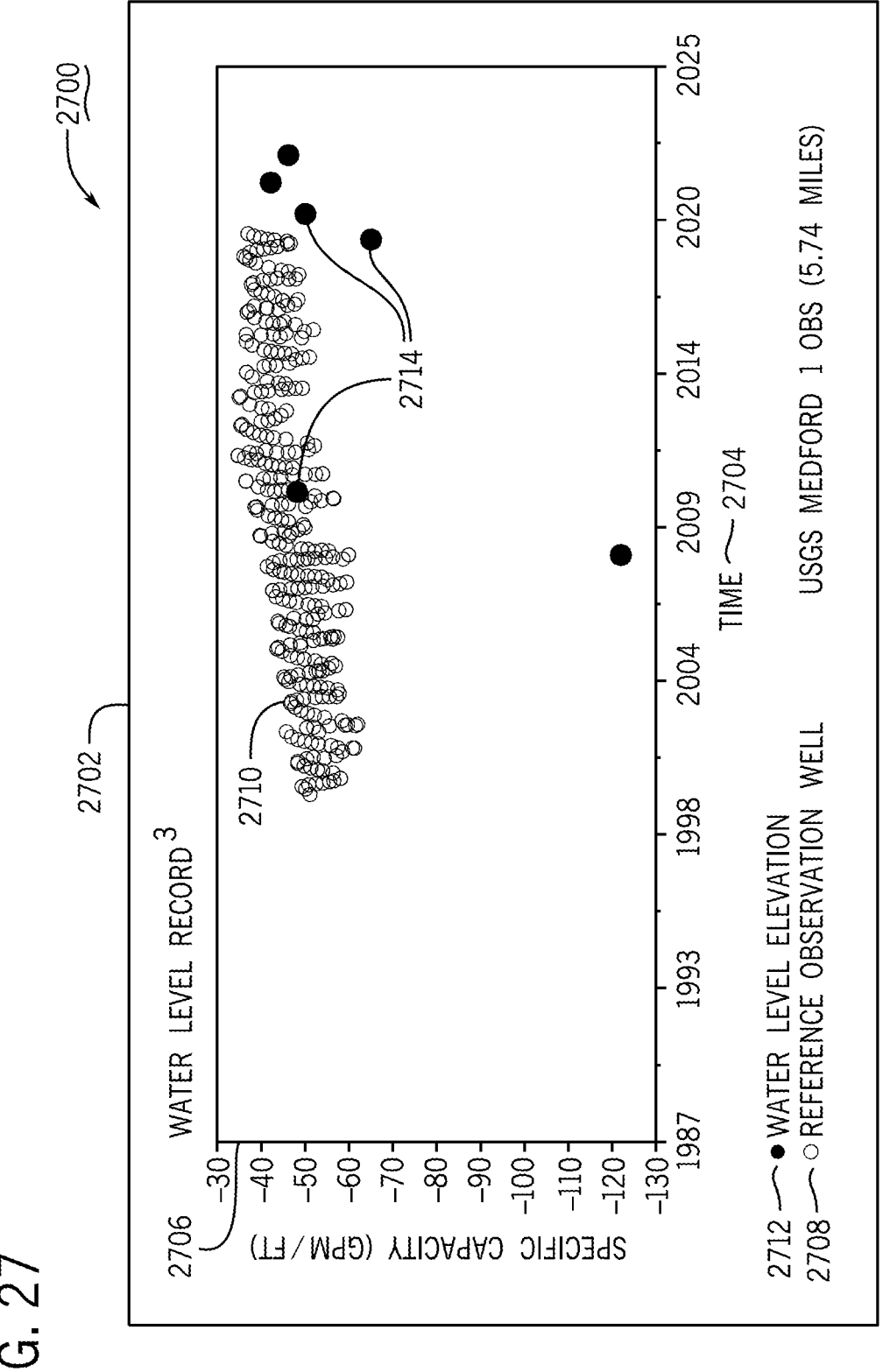
FIG. 27 illustrates a water level record component of a well yield evaluation worksheet (WYEW), according to embodiments of the invention.

FIG. 27 illustrates, generally at 2700, a water level record component of a well yield evaluation worksheet (WYEW), according to embodiments of the invention. With refence to FIG. 27, a water level record 2702 is illustrated with time along a horizontal axis 2704 and static elevation of the water level along a vertical axis 2706. The units applicable to the vertical axis 2706 are mean sea level (MSL). Data from two wells are plotted in 2702. A reference observation well at 2708 and 2710, which is also referred to in the art as a monitoring well. Data for the respective pumping well illustrated in FIG. 25 is shown in FIG. 27 at 2712 and 2714. Note that when the data 2714 are recorded the well has been in the OFF state for a time sufficient to allow the depth to water in the well to reach its static (non-moving) level.

In various embodiments, the data recorded in the water level record of 2702 is utilized in the analysis framework underlying generation of the WYEW to modify findings and recommendations for the particular well. In various embodiments, a WYEW can be augmented with the water level record 2702 for presentation to a user in various media, such as but not limited to, media for hardcopy such as paper, data file for storage on computer readable media, graphics file for display, etc.

Figure 28:
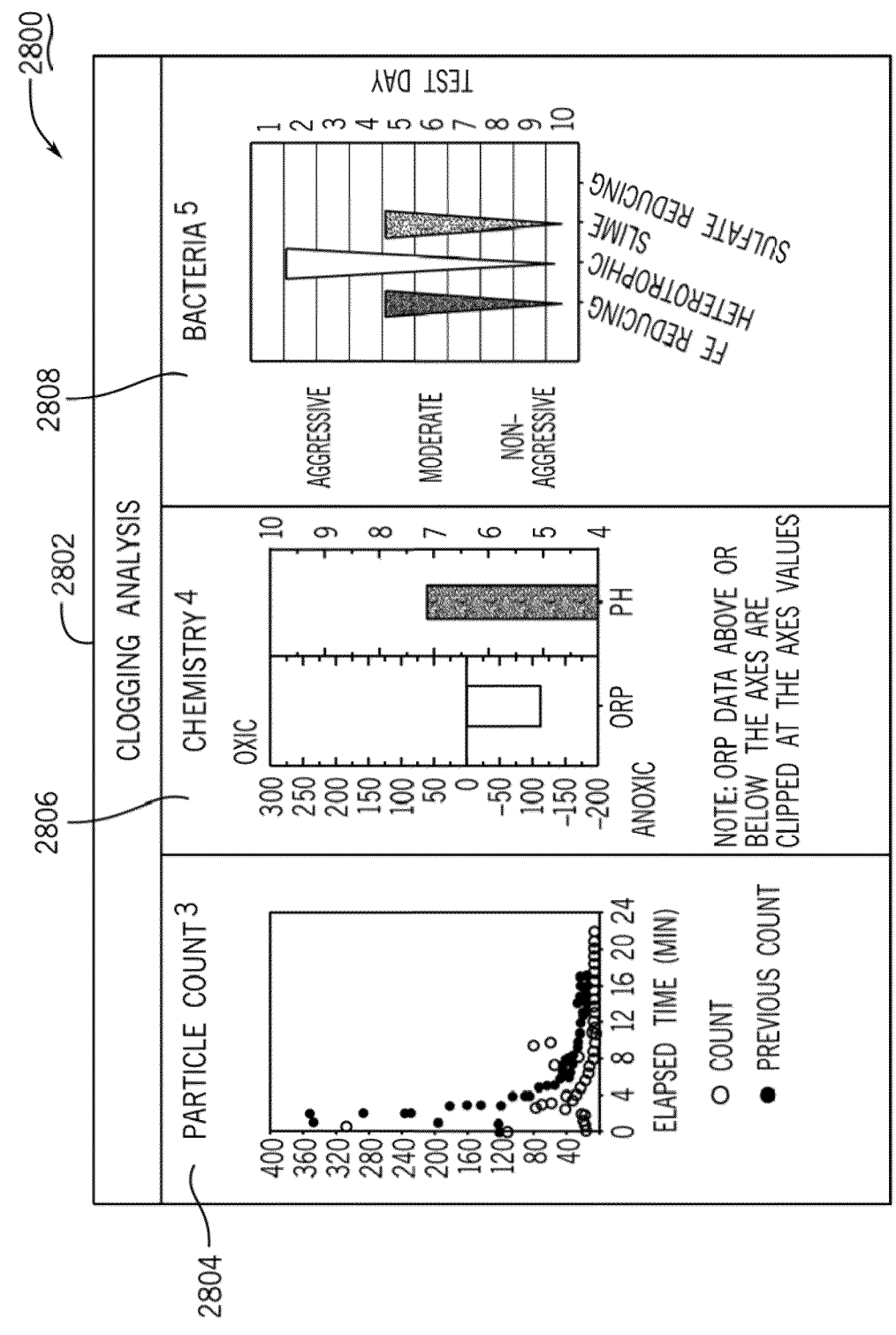
FIG. 28 illustrates a clogging analysis component of a well yield evaluation worksheet (WYEW), according to embodiments of the invention.

FIG. 28 illustrates, generally at 2800, a clogging analysis component of a well yield evaluation worksheet (WYEW), according to embodiments of the invention. With reference to FIG. 28, results of a clogging analysis 2802 are presented. The clogging analysis provides individual results for the three clogging modalities of mobile particles at 2804, well chemistry related to mineral/metal precipitation at 2806, and bacteria activity at 2808. In various embodiments, a WYEW can be augmented with the results of the clogging analysis 2802 for presentation to a user in various media, such as but not limited to, media for hardcopy such as paper, data file for storage on computer readable media, graphics file for display, etc.

FIG. 29 illustrates, generally at 2900, additional components of a well yield evaluation worksheet (WYEW), according to embodiments of the invention. With reference to FIG. 29, a well details component is illustrated at 2902. The well details component 2902 includes one or more of the specific elements of data shown in 2902, such as but not limited to date drilled, well permit number, permit number, permitted pumping capacity (PPC), ground elevation, M.P. Elevation, screen diameter, pump setting, top of screen, bottom of screen, maximum drawdown, aquifer material, and aquifer name. Note that the well details component can have one or more of the specific elements shown in 2902 and in some cases additional elements not shown. Abbreviations used with the elements in 2902 are: gpm (gallons per minute), feet (ft), inches (in), fbg (feet below ground), elev (ft-North American Vertical Datum of 1988 (NAVD88)), FMP (feet from measuring point), and M.P. (measuring point).

A first depth to water extrapolation component is illustrated at 2904 with sub label "1-Hour Pumping Conditions." The component 2904 presents an extrapolated depth to water using a 1-hour extrapolation time at the listed pumping rate of 778 gpm utilizing the process for estimating specific capacity described above. This extrapolated depth to water is labeled "Pumping level." The static depth to water is listed as 53.1 ft. Note that the component 2904 is based on a 30-minute pumping test, where the pumping rate was 778 gpm.

A well diagram component is illustrated at 2906. The well diagram component 2906 provides a pictorial presentation of the well including depths to the well screen, the pump setting, the pumping level, the static level, the ground elevation, and the riser elevation. The vertical scale provided in 2906 is labeled as feet below ground surface (fbg).

A second depth to water component is illustrated at 2908 with sub-label "THREE-DAY YIELD EVALUATION." The second depth to water component 2908 is based on the 30-minute pumping test described above extrapolated to a depth corresponding with a 3-Day extrapolated pumping time utilizing the mathematical model for aquifer transmission also described above. Note that the component 2908 can have one or more of the following sub-elements. The list of sub-elements described herein is given by way of example and does not limit embodiments of the invention. Sub-elements listed in 2908 are, but are not limited to, production pumping rate (gpm), production deficiency (gpm), evaluation pumping level (fbg), specific capacity (gpm/ft), safety interference factor (ft), available drawdown (ft), additional yield (gpm), and BWA permit restriction. In various embodiments, a WYEW can be augmented with the additional components shown at 2900 for presentation to a user in various media, such as but not limited to, media for hardcopy such as paper, data file for storage on computer readable media, graphics file for display, etc.

FIG. 30 illustrates, generally at 3000, an analysis results component of a well yield evaluation worksheet (WYEW), according to embodiments of the invention. With reference to FIG. 30, the analysis results component 3002 includes a sub-element of findings 3004 and a sub-element of operational improvements at 3006. Operational improvements are also referred to interchangeably as recommendations. The findings 3004 and operational improvements 3006 pertain to FIG. 25 through FIG. 29 above.

Findings address one or more of the following well-specific evaluation categories: (1) aquifer stability; (2) well yield record; (3) particle count (during surge); (4) aquifer oxidation properties; (5) bacteria presence in the well; and (6) well yield evaluation. At 3004 Finding #1 states that: "The aquifer is stable." The corresponding operational improvement at 3006 is: "No action is necessary." Instability in the aquifer can be related to movement of the static water level, such as declining or increasing aquifer static water level. The water level record 2702 (FIG. 27) illustrates aquifer stability since the static depth to water measurements 2714 are similar to the historical record illustrated at 2710 from the reference observation well.

At 3004 Finding #2 states that: "The specific capacity is between 50% and 80% of the Maximum specific capacity for the well. SC is stable." The multiyear analysis reveals that the specific capacity is declining as can be seen at 570 in FIG. 25, therefore the finding is: "SC is stable but declining." The corresponding operational improvement at 3006 is: "Enact recommendations below to support yield."

At 3004 Finding #3 states: "Particle count percent decline less than or equal to 20%." The corresponding operational improvement at 3006 is: "No action necessary." Alternatively, if the particle count percent decline had been greater, e.g., 50% then the recommended operational improvement at 3006 would have stated "Start and stop the pump more frequently."

At 3004 Finding #4 states: "Oxidation reduction potential less than-50 mV." The corresponding recommended operational improvement at 3006 states: "Reduced conditions—no action necessary." Alternatively, if the ORP measurement had been above +50 mV together with other specific clogging information relevant to mineral/metal precipitation, such as pH and location of pH and ORP on relevant phase diagrams for mineral/metals of concern the system would have directed the operational improvement(s) to decreasing the dissolved oxygen in the aquifer and/or installation of a custom extended pump sleeve (CEPS) as described in the figures above to "reverse" the water column.

At 3004 Finding #5 states: "Bacteria is moderately aggressive." The corresponding recommended operational improvement at 3006 states: "Treat well annually. Monitor growth." Treatments of bacteria to reduce growth and lower activity level have been described above in conjunction with the preceding figures, such as for example FIG. 11 through FIG. 14B.

At 3004 Finding #6 states: "Productivity is not within 20% of Permitted Pumping Capacity. Cannot attain PPC." The corresponding recommended operational improvement at 3006 states: "Maintenance required." The WYEW components listed above in FIG. 29 illustrate the #6 Finding and corresponding recommendation. With reference to FIG. 29, the well has a Permitted Pumping Capacity (PPC) of one thousand (1000) gpm as indicated in 2902. The 1-Hr Pumping Condition" used 778 gpm as the pumping rate and a one 1-Hour extrapolation time to estimate that the well would drawdown to 159.5 feet. The pump setting is at 190 fbg. After the one 1-Hour extrapolation time, only 30 feet of water cover remained above the pump. If this pump level were allowed to proceed the pumping rate would draw the pumping level down to the pump inlet resulting in cavitation and failure of water yield. Uncovering the pump is a condition to be avoided. Therefore, the pumping rate was reduced to 500 gpm in the simulation presented at 2908 for the 3-Day extrapolation time. The extrapolated depth to water is listed in 2908 as: "Evaluation pumping level (fbg): 141.1. Five hundred (500) gpm is a production deficit of minus −500 gpm, hence the operational improvement at 3006 in FIG. 30 maintenance is required. Taken together the 6 findings point to the third clogging modality, i.e., excessive bacteria growth, as the causative clogging modality that has caused the 500 gpm production deficiency. In various embodiments, a WYEW can be augmented with the additional components shown at 3000 for presentation to a user in various media, such as but not limited to, media for hardcopy such as paper, data file for storage on computer readable media, graphics file for display, etc.

Figure 31:
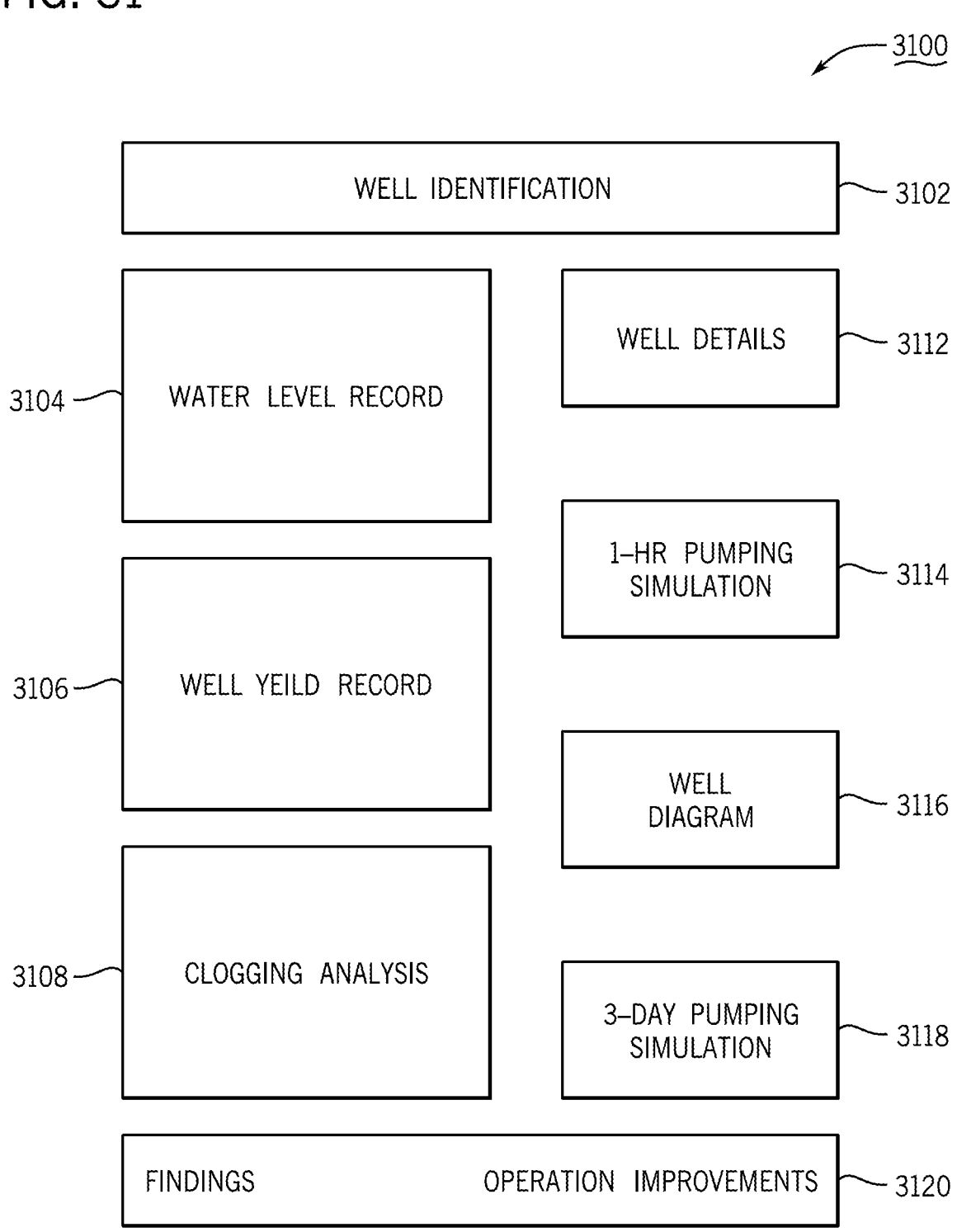
FIG. 31 illustrates a format of data presentation for a well yield evaluation worksheet (WYEW), according to embodiments of the invention.

FIG. 31 illustrates, generally at 3100, a format of data presentation for a well yield evaluation worksheet (WYEW), according to embodiments of the invention. With reference to FIG. 31, a region 3102 provides well identification. A non-limiting list of information that can be included in 3102 for well identification is, but is not limited to, such information as well name, well number, well address, aquifer location for the well, date of WYEW create, etc.

A non-limiting example of a location on the WYEW for a water level record is indicated at 3104. A non-limiting example of a water level record is illustrated in FIG. 27 and elsewhere in this description of embodiments.

A non-limiting example of a location on the WYEW for a water yield record is indicated at 3106. A non-limiting example of a water yield record for a well is illustrated in FIG. 25 and elsewhere in this description of embodiments.

A non-limiting example of a location on the WYEW for a clogging analysis is indicated at 3108. A non-limiting example of a clogging analysis is illustrated in FIG. 28 and elsewhere in this description of embodiments.

A non-limiting example of a location on the WYEW for well details is indicated at 3112. A non-limiting example of a well details is illustrated at 2902 in FIG. 29 and elsewhere in this description of embodiments. A non-limiting example of a location on the WYEW for a one 1-Hour pumping simulation is indicated at 3114. A non-limiting example of a one 1-Hour pumping simulation is illustrated at 2904 in FIG. 29 and elsewhere in this description of embodiments. A non-limiting example of a location on the WYEW for a well diagram is indicated at 3116. A non-limiting example of a well diagram is illustrated at 2906 in FIG. 29 and elsewhere in this description of embodiments. A non-limiting example of a location on the WYEW for a 3-Day pumping simulation is indicated at 3118. A non-limiting example of a 3-Day pumping simulation is illustrated at 2908 in FIG. 29 and elsewhere in this description of embodiments. A non-limiting example of a location on the WYEW for findings and operational improvements is indicated at 3120. A non-limiting example of findings and operational improvements is illustrated at 3000 in FIG. 30 and elsewhere in this description of embodiments.

In various embodiments, a WYEW can be augmented with one or more of the additional components shown at 3100 for presentation to a user in various media, such as but not limited to, media for hardcopy such as paper, data file for storage on computer readable media, graphics file for display, etc.

As described above, a Well Yield Evaluation Worksheet (WYEW) is created for each well under evaluation. The findings and recommendations associated with a WYEW identify the conditions that are affecting yield as well as the operational improvements that are available to remediate the conditions so that yield can be restored. In sum, the WYEW provide a well operator with the tools needed to optimize well yield for the well. WYEWs can be applied to a group of wells within the well evaluation framework. Introduction of a Well Performance Metric (WPM), in various embodiments, provides a flexible metric for comparisons of wells within a group of wells. The WPM presents a well ranking paradigm that is used to prioritize well maintenance and well maintenance dollars across a group of wells. When the Well Yield Evaluation Framework includes WYEWs and WPMs applied to a group of wells, a well field operator has the tools needed to optimize well field yield while minimizing dollars spent.

Well Performance Metric (WPM)

Figure 32:
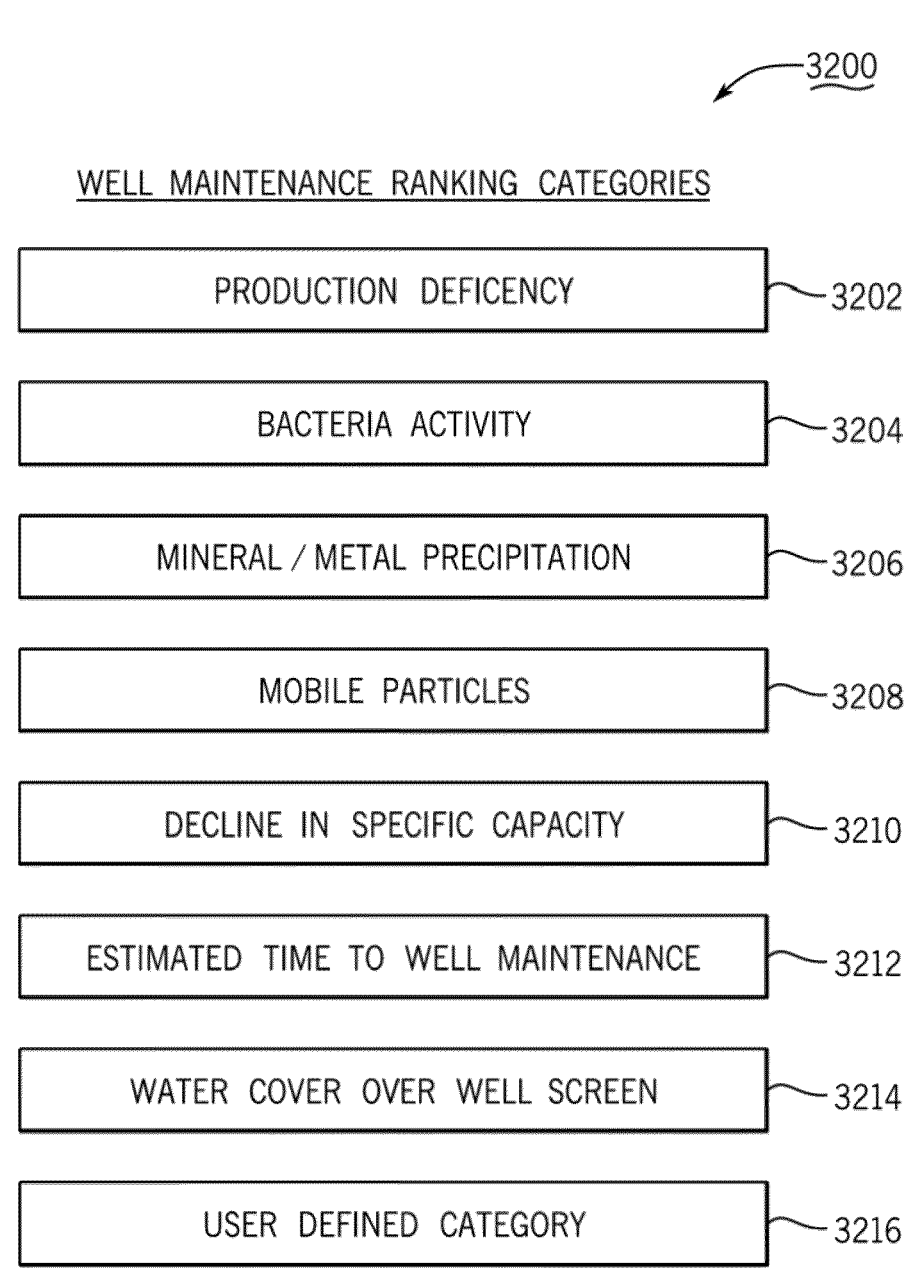
FIG. 32 illustrates a list of Well Performance Metric (WPM) categories, according to embodiments of the invention.

As used in this description of embodiments, the following terms are interchangeable, Well Performance Metric (WPM), Well Maintenance Ranking Number (WMRN), and Normalized Score. No limitation is implied by the use of one term over another. FIG. 32 illustrates, generally at 3200, a list of WPM categories, according to embodiments of the invention. With reference to FIG. 32, it has been discovered that reduction in yield of a well can be quantified using a small set of categories (also referred to equivalently as factors) that are applied to a well or wells within the analysis framework. These categories are, but are not limited to: production deficiency 3202, which is also referred to as loss of yield; a second category 3204 is bacteria activity; a third category 3206 is mineral/metal precipitation; a fourth category 3208 is mobile particles; a fifth category 3210 is decline in specific capacity; a sixth category 3212 is estimated time to well maintenance; a seventh category 3214 is water cover over well screen; and an eight category 3216 is a user defined category. In various embodiments, at one end of the complexity scale a WPM can be cast with various levels of granularity incorporating only one of the categories shown above in FIG. 32. At the other end of the complexity scale, a WPM can be constructed to include multiple categories. In various embodiments, a WPM is based on one or more of the categories illustrated in FIG. 32.

Figure 33:
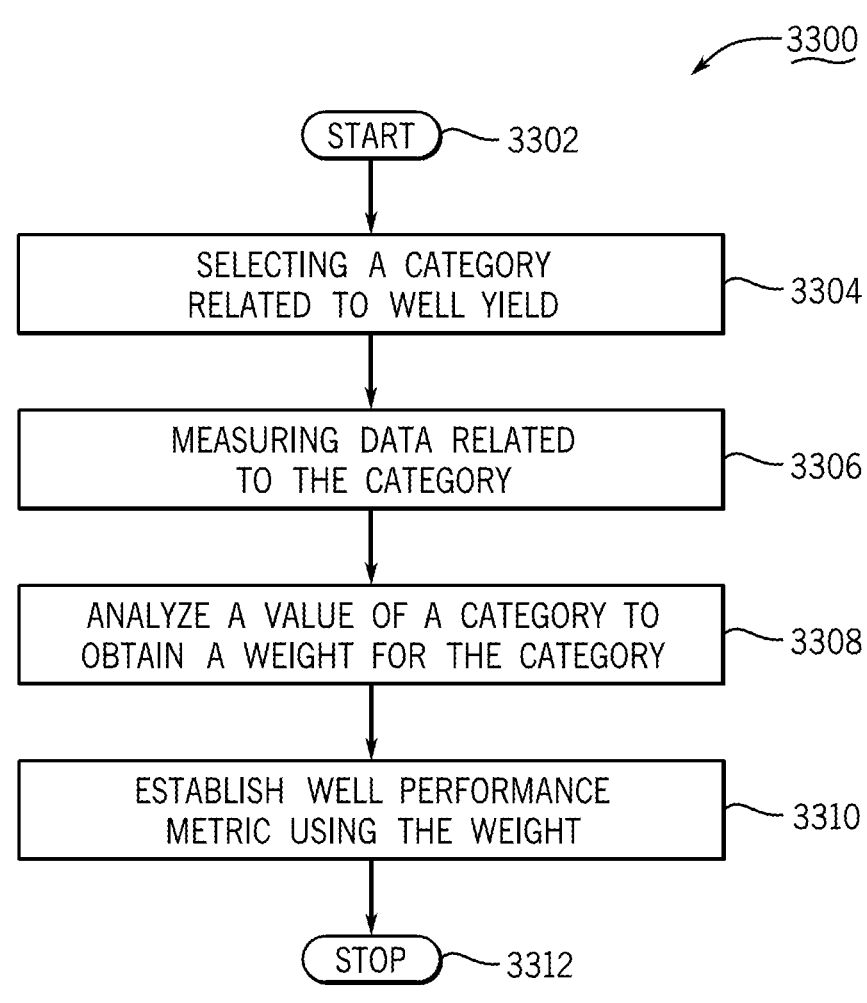
FIG. 33 illustrates a process to calculate a Well Performance Metric (WPM), according to embodiments of the invention.

FIG. 33 illustrates, generally at 3300, a process to calculate a Well Performance Metric (WPM), according to embodiments of the invention. With reference to FIG. 33, a process commences at a block 3302. At a block 3304 a category is selected. The category is related to well yield. At a block 3306 data is collected for the category. The data is used to establish a current value for the category. At a block 3308 the current value is analyzed and one or more of: (1) historical values for the category, and (2) an estimated future value for the category, which are used to obtain a weight for the category. For some categories, the weight for the category is equal to the category value. At a block 3310 the weight for the category is used to establish the well WPM. The process stops at a block 3312. In various embodiments of the invention, the process of FIG. 33 is applied to one or more of the categories shown in FIG. 32 to formulate the WPM.

FIG. 34 illustrates first equations used to calculate a Well Performance Metric (WPM), according to embodiments of the invention. With reference to FIG. 34, an equation 3402 is used to establish well performance metrics ($WPM_i$) for a general number of M wells 3416 and a general number of N categories 3418. $CATEGORY_{i,j}$ at 3406 represents either a category value for the jth category of the ith well or a weight for the category value. $ADJFAC_j$ at 3408 represents an adjustment factor to be multiplied by the jth category value or weight for the category value $CATEGORY_{i,j}$. The normalized $NWPM_i$ is the normalized well performance metric for the ith well and is given by 3404. $WPM_{NORM}$ is the normalization value used in 3404 and is given by 3414. $WPM_{NORM}$ is usually the maximum $WPM_i$ value in the WPM array. In various embodiments, a scaling can be applied to the array of normalized $NWPM_i$ values to shift the values to a range of approximately zero (0) to 100 for example.

FIG. 35 illustrates second equations used to calculate a Well Performance Metric (WPM), according to embodiments of the invention. With reference to FIG. 35, an offset for a category is defined at 3504, where $OFFSET_j$ is an offset added to the ith well's category value $CATEGORY_{i,j}$. Equation 3502 illustrates the use of $OFFSET_j$ in the $WPM_i$ calculation, i.e., $OFFSET_j$ is a value added to $CATEGORY_{i,j}$ for the jth category.

Figure 36:
FIG. 36 illustrates Well Performance Metrics (WPMs) for a group of 35 wells based on the category of production deficiency, according to embodiments of the invention.

As an illustration of establishing Well Performance Metrics (WPMs) for a group of wells, the equations shown above in conjunction with FIG. 34 are used for a group of 35 wells for the category of production deficiency, which is lost flow rate expressed as volume per unit time, such as for example gallons per minute (gpm). FIG. 36 illustrates WPMs for the group of wells based on the category of production deficiency, according to embodiments of the invention. With reference to FIG. 36, i is equal to 35, j is equal to 1, and $ADJFAC_1$ is equal to 1. In one or more embodiments, for the category of production deficiency, the category value is directly equal to the category weight. The results of the analysis are normalized and plotted in ascending order using a bar chart in 3600 with well number along a horizontal axis 3602 and relative normalized magnitude along a vertical axis 3604. The results of the analysis presented at 3600 reveal that WELL 05, WELL 12, and WELL 13 indicated at 3606 have the greatest production deficiency. The group of wells beginning on the left with WELL 25 up through WELL 07 indicated at 3608 have the least production deficiency. Other wells between 3608 and 3606 have increasing production deficiency. The well field analysis results present in 3600 illustrate establishing WPMs for the group of 35 wells based on the category of production deficiency. As an example, and with no limitation implied thereby, a production deficiency category value is based on the number of gpm that the well is not producing. Thus, in this embodiment, category value is directly equal to the production deficiency which is directly equal to the category weight. In other embodiments, a production deficiency value is assigned to a weight and the weight is used in equation 3402. Assigning a weight to a category value is described in more detail below.

Figure 37:
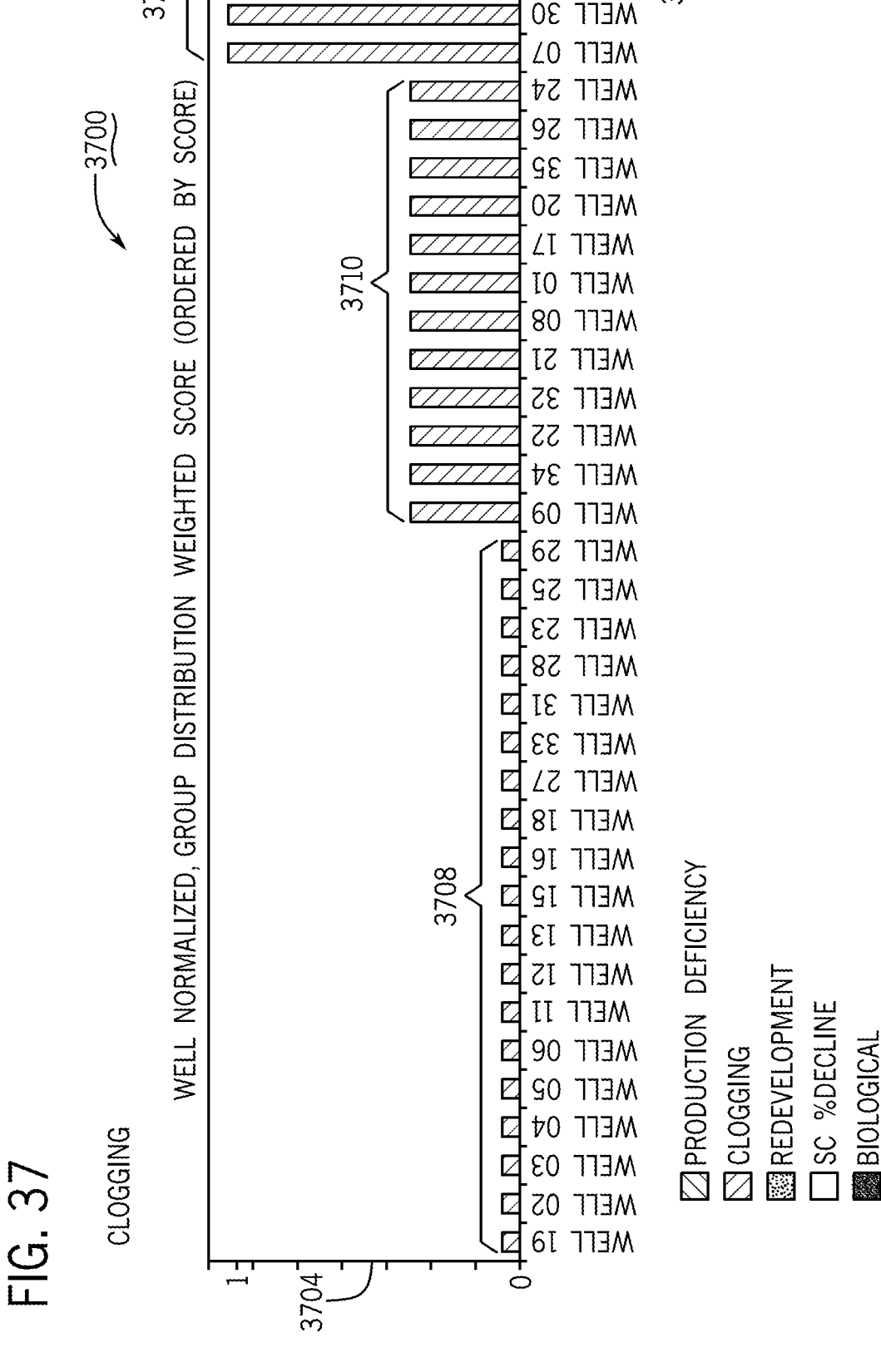
FIG. 37 illustrates Well Performance Metrics (WPMs) for the group of 35 wells based on the category of clogging potential, according to embodiments of the invention.

As an illustration of establishing WPMs for the group of wells, the equations shown above in conjunction with FIG. 34 are used for the group of 35 wells for the category of clogging potential. FIG. 37 illustrates WPMs for a group of wells based on the category of clogging potential, according to embodiments of the invention. With reference to FIG. 37, i is equal to 35, j is equal to 1, and $ADJFAC_1$ is equal to 1. In the embodiment illustrated in FIG. 37 the category of "clogging potential" includes the following components: (1) ORP measurement, (2) water column height above the well screen, (3) aquifer type (confined or unconfined), and (4) estimated time to redevelopment. Weights are assigned to the components, the weights are summed and used in equation 3402. Assigning weights to components is described more fully below. The results of the analysis are normalized using equation 3404 and are plotted in ascending order as a bar chart in 3700 with well number along a horizontal axis 3702 and relative normalized magnitude along a vertical axis 3704. The results of the analysis presented at 3700 reveal that WELL 07, WELL 30, WELL 14, and WELL 10 indicated at 3706 have the greatest effects from the clogging modalities. The group of wells beginning on the left with WELL 19 up through WELL 29 indicated at 3708 have the least effects from the clogging modalities. Other wells at 3710 are experiencing intermediate effects from the clogging modalities. The well field analysis results present in 3700 illustrate establishing WPMs for the group of 35 wells based on the category of clogging potential. The clogging category illustrated in FIG. 37 is formulated by consideration of several of the categories shown in FIG. 32. Note that in other embodiments the category of "clogging potential" can be formulated in a different way, for example use of other clogging specific information such as presence of mineral/metals, pH, and phase charts for minerals/metals, etc. The example of the category of clogging potential used in the analysis underlying the establishment of the WPMs shown in 3700 using the combination of: (1) ORP measurement, (2) water column height above the well screen, (3) aquifer type (confined or unconfined), and (4) estimated time to redevelopment is given merely for example and does not limit embodiments of the invention.

Figure 38:
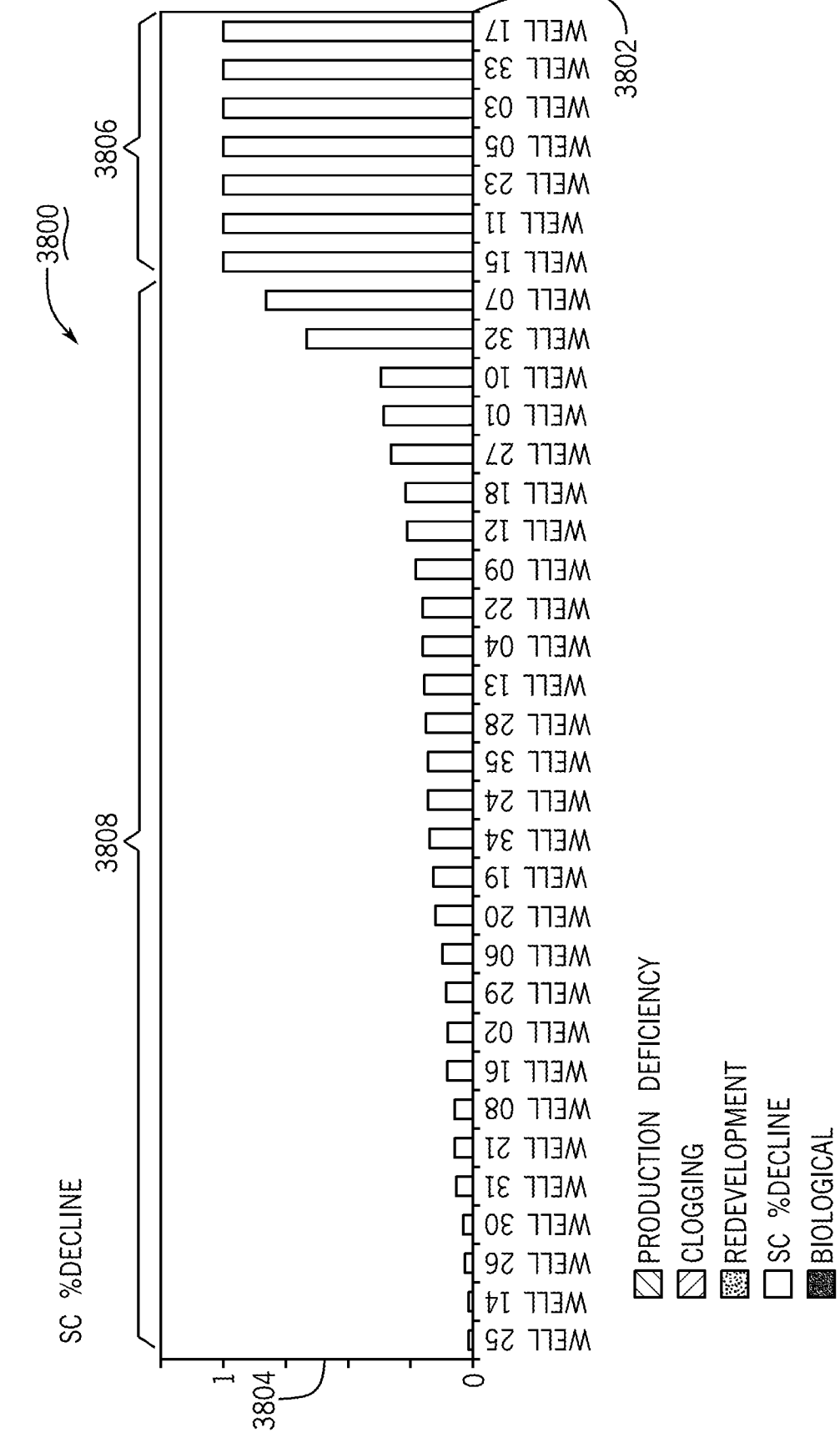
FIG. 38 illustrates Well Performance Metrics (WPMs) for the group of 35 wells based on the category of percent decline of specific capacity, according to embodiments of the invention.

As a further illustration of establishing Well Performance Metrics (WPMs) for the group of wells, the equations shown above in conjunction with FIG. 34 are used for the group of 35 wells for the category of specific capacity decline as a percentage of maximum specific capacity. FIG. 38 illustrates WPMs for the group of wells based on the category of percent decline of specific capacity, according to embodiments of the invention. With reference to FIG. 38, i is equal to 35, j is equal to 1, and $ADJFAC_1$ is equal to 1. In one or more embodiments, for the category of percent decline of specific capacity, a category value is directly equal to the category weight. The results of the analysis are normalized and plotted in ascending order as a bar chart in 3800 with well number along a horizontal axis 3802 and relative normalized magnitude along a vertical axis 3804. The results of the analysis presented at 3800 reveal that wells indicated at 3806 have the greatest decline in specific capacity. The group of wells indicated at 3808 have the least decline in specific capacity increasing from left to right. The well field analysis results present in 3600 illustrate establishing WPMs for the group of 35 wells based on the category of decline in specific capacity.

Figure 39A:
FIG. 39A illustrates Well Performance Metrics (WPMs) for the group of 35 wells based on the category of biological activity, according to embodiments of the invention.

As a further illustration of establishing Well Performance Metrics (WPMs) for the group of wells, the equations shown above in conjunction with FIG. 34 are used for the group of 35 wells for the category of biological activity. FIG. 39A illustrates Well Performance Metrics ($WPM_i$) for the group of wells based on the category of biological activity, according to embodiments of the invention. With reference to FIG. 39A, i is equal to 35, j is equal to 1, and $ADJFAC_1$ is equal to 1. In one or more embodiments, for the category of biological activity, a category value is directly equal to a category weight. The biological category weights are obtained from a measure of how aggressive the different types of bacteria are during the analysis of a water sample taken from the well as described above. Biological category weights are discussed in more detail below. The results of the analysis are normalized and plotted in ascending order as a bar chart in 3900 with well number along a horizontal axis 3902 and relative normalized magnitude along a vertical axis 3904. The group of wells illustrate variation in biological activity ranging from zero for WELL 09 at the far left of the horizontal axis 3902 to a maximum at WELL 25 on the far right of the horizontal axis 3902. The well field analysis results present in 3900 illustrate establishing WPMs for the group of thirty (35) wells based on the category of biological activity.

Figure 39B:
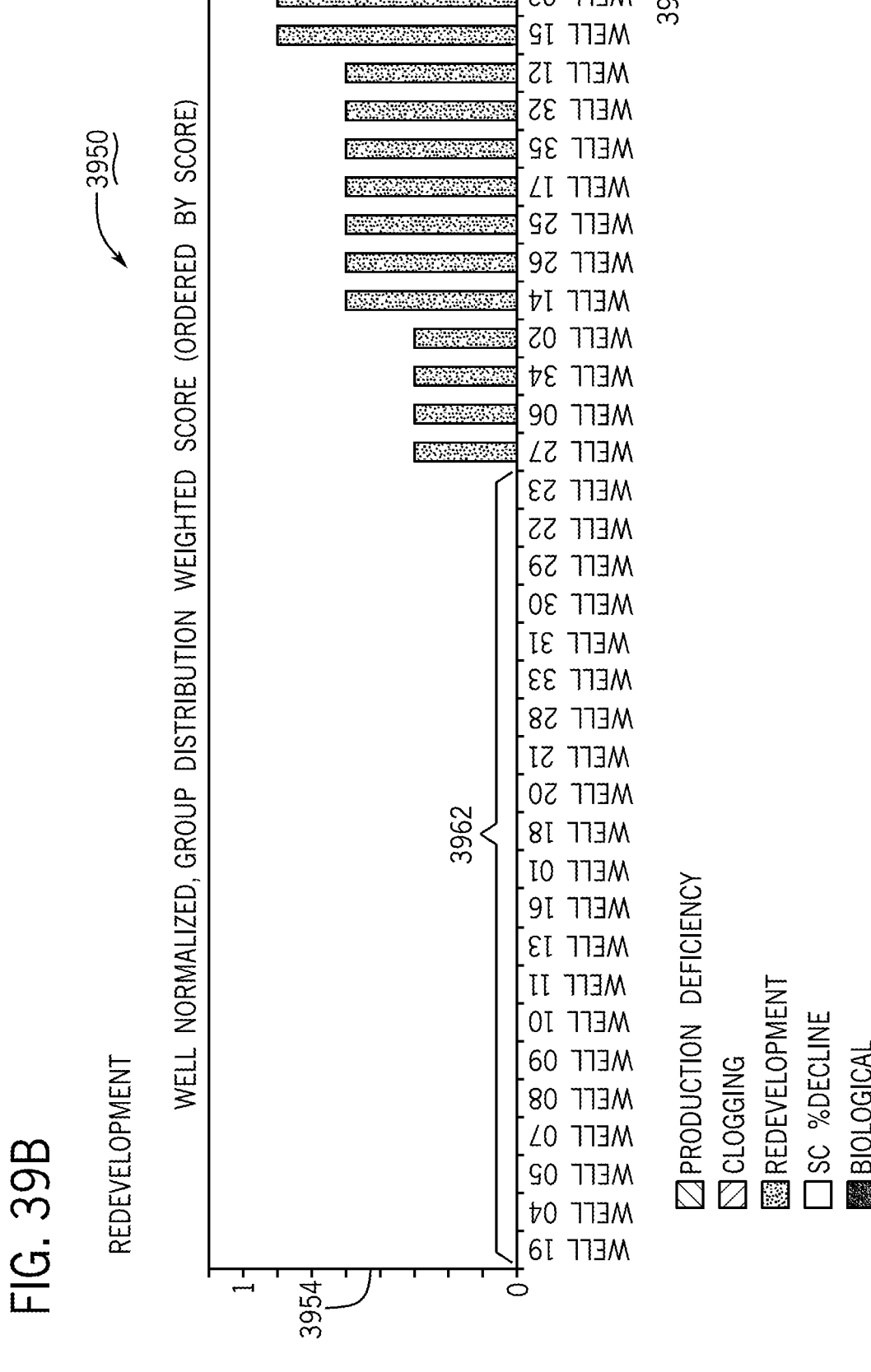
FIG. 39B illustrates Well Performance Metrics (WPMs) for the group of 35 wells based on the category of estimated time to development, according to embodiments of the invention.

As a further illustration of establishing Well Performance Metrics (WPMs) for the group of wells, the equations shown above in conjunction with FIG. 34 are used for the group of 35 wells for the category of estimated time to redevelopment. FIG. 39B illustrates WPMs for the group of wells based on the category of estimated time to redevelopment, according to embodiments of the invention. With reference to FIG. 39B, i is equal to 35, j is equal to 1, and $ADJFAC_1$ is equal to 1. In one or more embodiments, for the category of estimated time to redevelopment, a category value is obtained from a category weight. Obtaining category values and weights is described more fully below. The results of the analysis are normalized and plotted in ascending order as a bar chart in 3950 with well number along a horizontal axis 3952 and relative normalized magnitude along a vertical axis 3954. The results of the analysis presented at 3950 reveal that WELL 24, having WPM indicated at 390 is the well with the shortest estimated time to redevelopment. The group of wells indicated at 3962 have the longest estimated time to redevelopment. The WPMs for these wells, i.e., zero (0) are consistent with healthy wells that are having the least amount of maintenance issues. The well field analysis results present in 3950 illustrate establishing WPMs for the group of 35 wells based on the category of estimated time to redevelopment.

Figure 40:
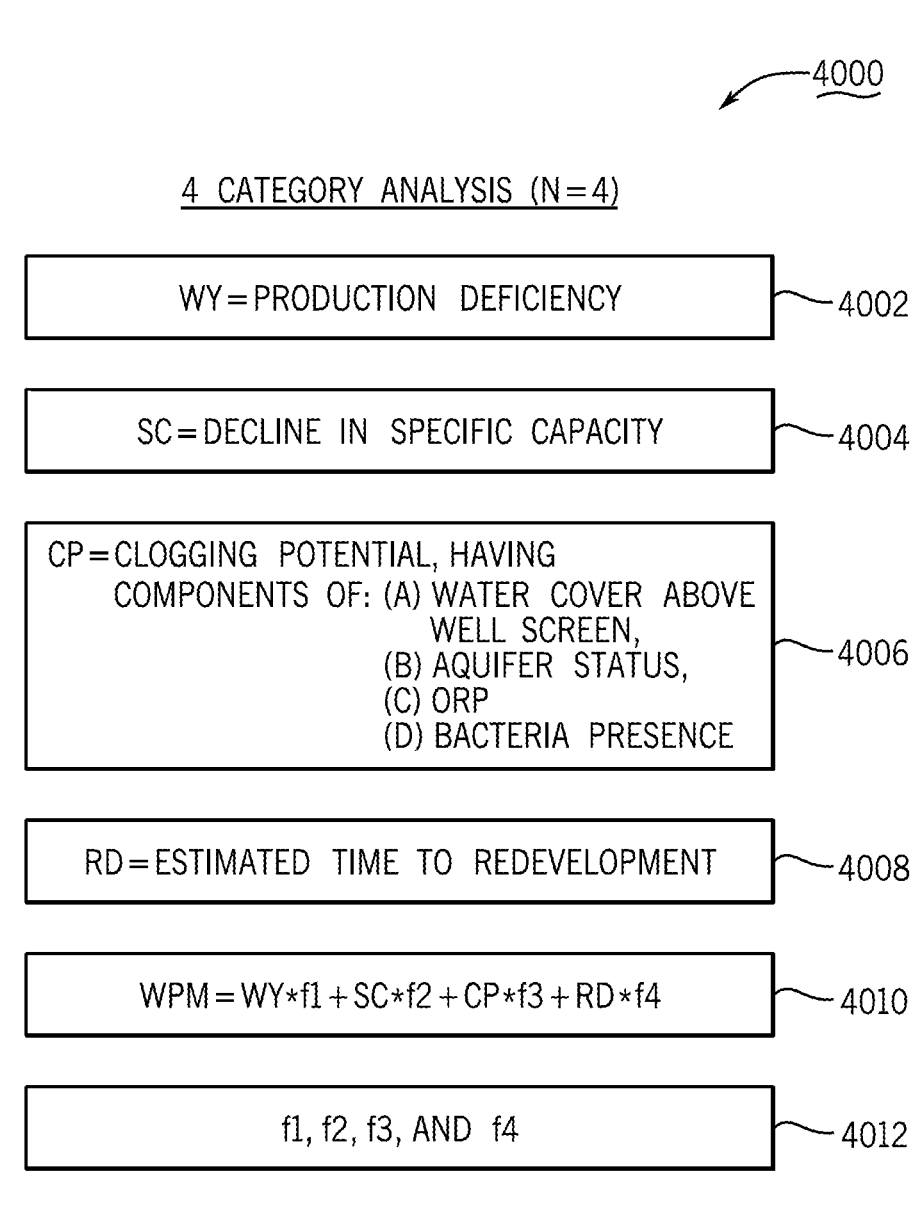
FIG. 40 illustrates formulating Well Performance Metrics (WPMs) for a well based on four categories, according to embodiments of the invention.

FIG. 40 illustrates, generally at 4000, formulating Well Performance Metrics (WPMs) for a well based on four categories, according to embodiments of the invention. With reference to FIG. 40, an analysis formulation for WPMs utilizes four categories. A first category 4002 is production deficiency. A second category 4004 is decline in specific capacity as a percentage of maximum specific capacity. A third 4006 category is clogging potential. In this formulation, clogging potential 4006 is based on the components of: (a) water cover over screen, (b) aquifer status (confined verses unconfined), (c) ORP measurement, and (d) bacteria presence. A fourth category 4008 is estimated time to well maintenance. An equation for WPM is given at 4010. Category adjustment factors f1, f2, f3, and f4 are given at 4012. In the formulation of 4010, values for the four categories are multiplied by their respective category adjustment factor, i.e., f1, f2, f3, and f4 and the results are summed to form a WPM value for a given well. Indices for well number i and category j have been omitted to preserve clarity in 4010. Adjustment factors f1, f2, f3, and f4 can be the same number or different numbers depending on the adjustment factors established by a user for a group of wells. Adjustment factors can be used to change the relative importance of one category as compared to another during the WPM calculation. For example, uniform adjustment factors imply that f1, f2, f3 and f4 have the same value. As a non-limiting example of adjustment factors having different values, if the well yield (WY) category is twice as important to calculation of a WPM as the decline in specific capacity (SC) category, then f1 will be twice as large as f2 and so on.

Category Values and Weights

In various embodiments, a value for a category can be directly used as the weight, for example the numerical value of production deficiency in gpm described above. Which means that if a production deficiency for a well is 350 gpm then the value 350 is used for the category value in for example equation 3402. In some embodiments, some parameters like ORP measurements are not used directly but are instead converted into a weight. The following example for ORP measurements is used for illustration with no limitation implied thereby. For ORP measurements greater than 50 mV a weight of 50 points is assigned to the ORP measurement. For ORP measurements of less than 50 mV then zero (0) points are assigned.

Weights for a category value can be established according to different paradigms. One paradigm given only for illustration, and with no limitation implied thereby, is a weight of one (1) is given for a value that is unchanged from a design specification. A current fraction of the original design specification value is obtained from testing and, for the example of well yield, the reciprocal of the current fraction is used to establish a current weight. Thus, for well yield, reduction in performance results in weights greater than 1. A well yield which is 20% of the design specification would produce a weight of 5 as follows: 5=(1/0.2). A well yield of 10% of the design specification would produce a weight of 10 as follows: 10=1/0.1. Thus, a larger value for a weight (10 verses 5) means that a WPM of 10 is greater than a well maintenance number of 5 and that well having the WPM of 10 is in need of maintenance sooner than is the well with the WPM of 5.

Another example of using weights instead of a category value directly occurs in some embodiments with percent decline in specific capacity (DSC). In one or more embodiments, weights are assigned as follows: 75 points for a 50% or more decline in specific capacity; 25 points for a decline of specific capacity in the range of 20%-50%; and zero (0) points for a decline in specific capacity of less than 20%. Decline in specific capacity can be alternatively quantified by using the category value for the reduction in gpm/ft directly instead of using the decline expressed as a percentage of maximum.

In various embodiments, category values for bacteria activity can be formulated in different ways. In one method of quantification of category values for bacteria activity, noting that the BART analysis runs for 10 days, with the day number recorded that corresponds to the first day that bacteria is observed. The highest score is given to appearance of bacteria on the first day and the lowest score is given to the first appearance of bacteria on the last day of the 10-day period. Thus, 10 points is awarded to bacteria first observed on day one (1), 9 points is awarded to bacteria first observed on day 2, . . . , One (1) point is awarded to bacteria first observed on day 10. The number of different BART analysis bottles used in the biological analysis are handled similarly and are summed to provide the biological category value. Another method of quantifying category values for bacteria takes into account the degree to which bacteria contribute to the clogging modality, Slime bacteria contribute more to the bacteria clogging modality than does Aerobic Heterotrophic bacteria. Thus, the point allocation for Iron or Heterotrophic bacteria can be divided by two relative to slime bacteria.

In various embodiments, a value for the clogging potential category can be formed by a summation of the contributions from several different clogging components. In one example given only for illustration, with no limitation implied thereby, a worst case clogging value has a total of 130 available points distributed as follows. If water cover over screen is less than 20 feet, then 20 points are assigned. If the aquifer status is unconfined 50 points are assigned. If the aquifer status is confined zero (0) points are assigned. If ORP is greater than 50 mV, then 50 points are assigned. If ORP is less than 50 mV, then zero (0) points are assigned. If bacteria is present, then 10 points are assigned. If bacteria are not present, then zero (0) points are assigned. In various embodiments, the Well Analysis Engine (WAE) retrieves the relevant data from storage and applies the proper points for each clogging component to arrive at a clogging value that is used in equation 4006 for each well.

Estimated time to well redevelopment is an important category and can be scored in different ways within the WAE. In one or more embodiments, a rate of decline in specific capacity is estimated for a well utilizing the process described above and illustrated with line 570 in FIG. 5. A slope of line 570 is measured, and in some embodiments using the most recent year of data and at least two separate measurements of specific capacity, the slope is transformed into a weight for the category of estimated time to redevelopment. One transformation and set of weights will assign points as follows: If the estimated time to redevelopment is in the window of 1-2 years, then a weight of 500 points is assigned. If the estimated time redevelopment is in the window of 3-4 years, then a weight of 200 points is assigned. If the estimated time redevelopment is in the window of 5-10 years, then a weight of 25 points is assigned. If the estimated time redevelopment is greater than 10 years, then a weight of zero (0) points is assigned.

Estimated time to development is an example of how a category can be used simultaneously as a category and as a component of a category. Note that the category of "estimated time to redevelopment" appears above in the category of "clogging potential" FIG. 37. Estimated time to redevelopment is used in FIG. 39B, FIG. 40, and FIG. 41 as a category. Thus, in the processing of the 35 well group, described herein "estimated time to redevelopment" is used both as a component of a category and as a category.

After the category values and/or category weights are established equation 4010 is then applied to the relevant category weights for each well in a group of wells to establish WPMs for the group. Noting that with some categories the category value can be equal to the category weight as described above for production deficiency.

Note that the adjustment factor $ADJFAC_j$ and the offset parameter $OFFSET_j$ can be used either together or independently to shift a contribution of one category relative to another category. Use of the adjustment factor $ADJFAC_j$ and/or the offset parameter $OFFSET_j$ can influence allocation of weight to a category or to one or more components of categories. Thus, the WAE provides a flexible analysis environment that can handle the many variations present in real world well fields. Note that to preserve clarity in equation 4010, the offset parameters have been omitted. However, the offset parameters can be included in equation 4010 following the form shown in FIG. 34.

Well Performance Metric (WPM) Using a Five Category Example

Figure 41:
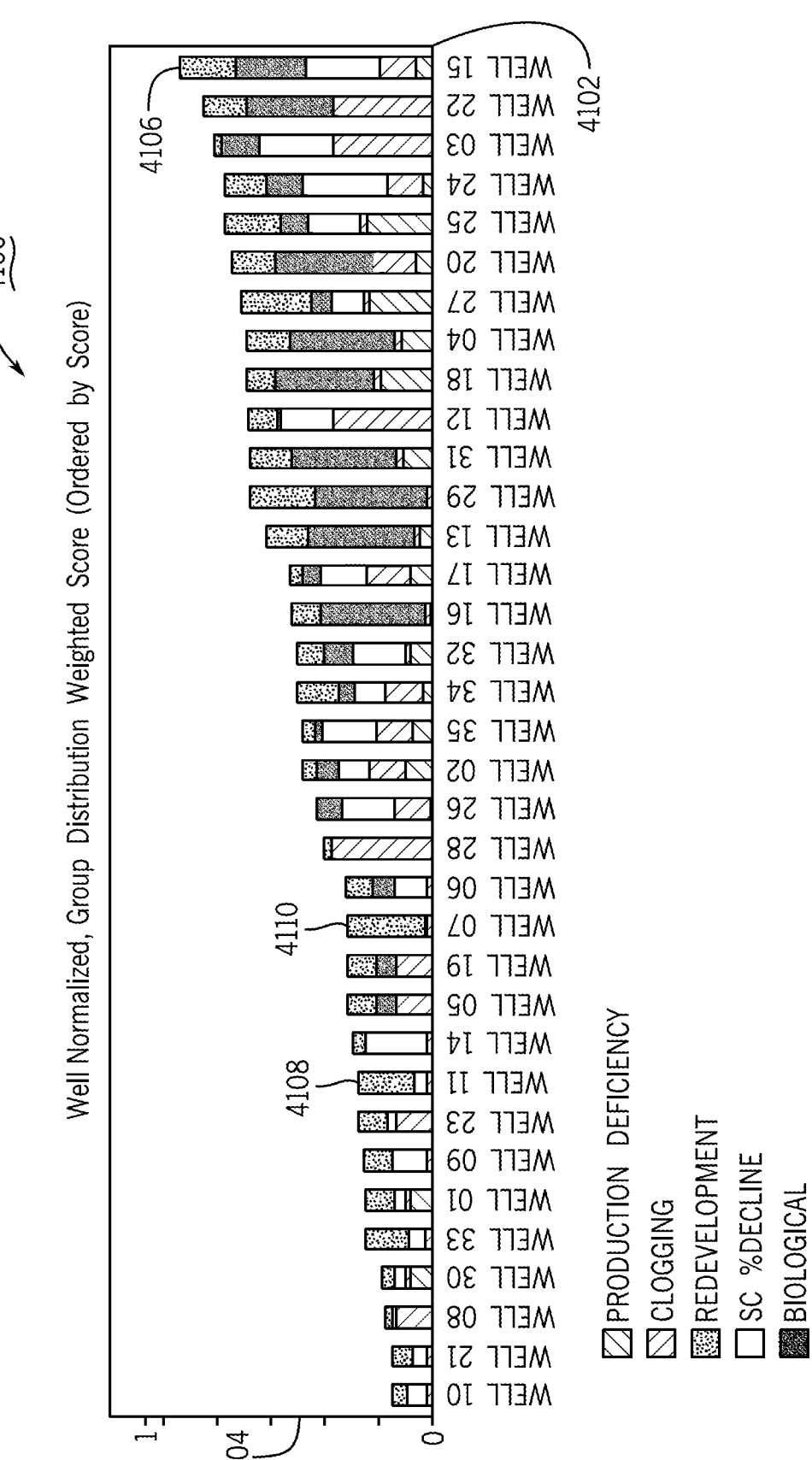
FIG. 41 illustrates Well Performance Metrics (WPMs) for the group of the group of 35 wells based on the categories of time to redevelopment, and the categories shown in FIG. 36, FIG. 37, FIG. 38, and FIG. 39A, according to embodiments of the invention.

FIG. 41 illustrates, generally at 4100, Well Performance Metrics (WPMs) for the group of the group of 35 wells based on the categories shown in FIG. 36, FIG. 37, FIG. 38, FIG. 39A, and FIG. 39B, according to embodiments of the invention. With reference to FIG. 41, the group of 35 wells previously described above in conjunction with FIG. 36 through FIG. 39B are analyzed in the Well Yield Analysis Framework to produce composite WPMs representative of combining the five categories shown individually in FIG. 36, FIG. 37, FIG. 38, FIG. 39A, and FIG. 39B. The results of the analysis are normalized and plotted in ascending order as a bar chart in 4100 with well number along a horizontal axis 4102 and relative normalized magnitude along a vertical axis 4104. The contribution to the Well Performance Metric (WPM) from each of the four categories is illustrated by line type. The composition of a WPM provides information on what is needed to restore well yield to an individual well, while the ordering by ascending WPM indicates which wells are in the most urgent need of maintenance. For example, the well at 4106 has the largest WPM meaning that this well is experiencing decline in specific capacity, production deficiency, and the third modality of clogging high bacteria activity. What the WPM component analysis reveals for WELL 15, as shown at 4106, is that it is necessary to address the third modality of clogging and that the estimated time to redevelopment is approaching. Treatments such as those described above using biocides will kill bacteria populations and restore well yield to WELL 15.

Other wells, such as WELL 11 at 4108 and WELL 07 at 4110, have WPMs that are approximately one-third the magnitude of 4106, these two wells have not yet experienced production deficiency and only WELL 11 has experienced a slight decline in specific capacity. WPM at 4108 (WELL 11)

and WPM at 4110 (WELL 07) indicate that both of these wells have high bacteria activity. Without an accompanying significant reduction in specific capacity, it would be premature to take WELL 11 or WELL 07 offline to treat these wells for high bacteria activity. Some wells have high bacteria activity, but that activity does not result in the bacteria clogging modality negatively impacting performance. In light of the analysis presented for the 35 wells at 4100 maintenance is needed for the Well 15 based on its WPM at 4106 in order to increase its production and overcome its production deficiency. Other wells, some of which are discussed below, require different remediation following the teachings presented herein. The five category example of WPM scoring is given only for example and does not limit embodiments of the invention.

Well Maintenance Tracking Record

Figure 42A:
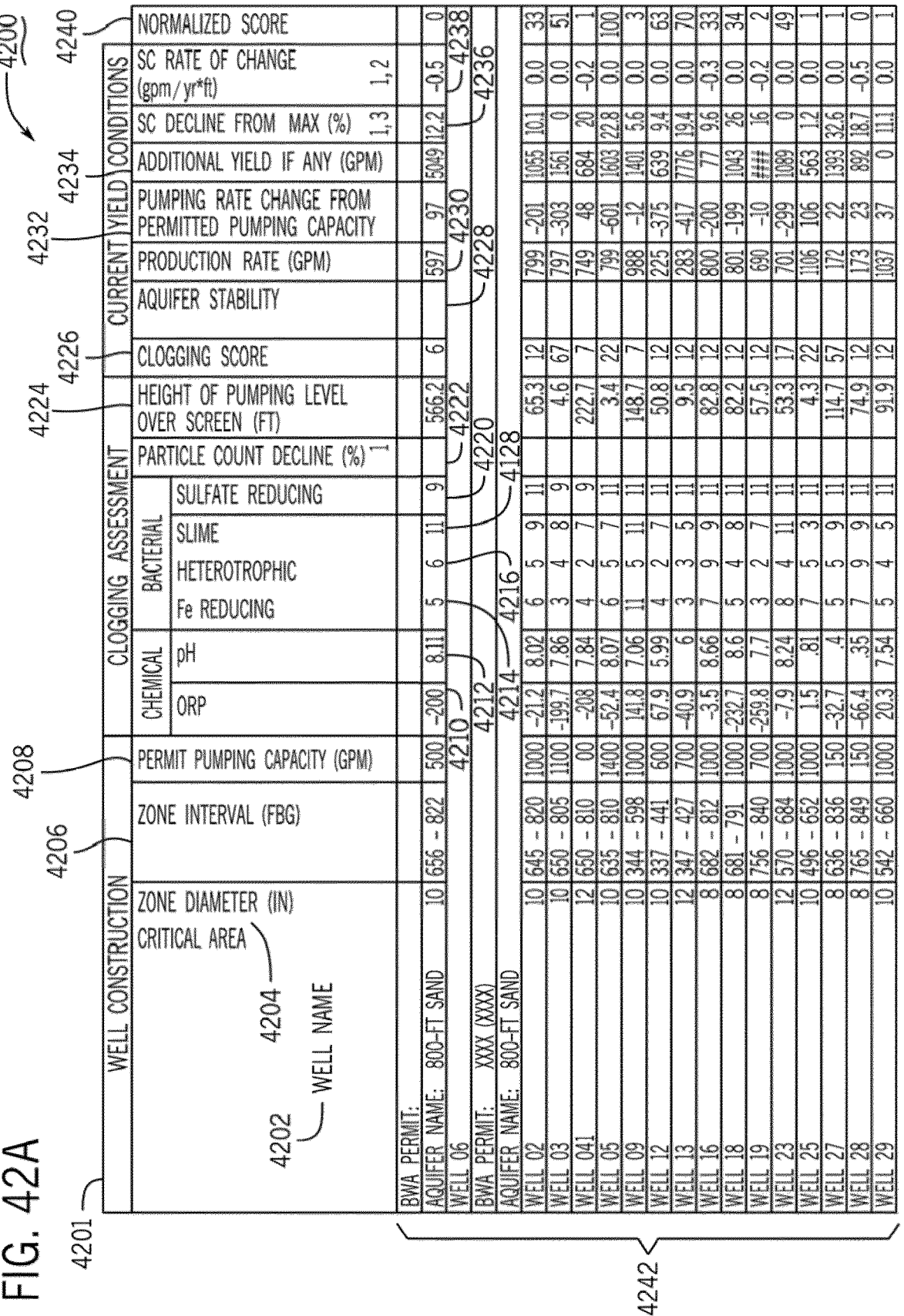

FIGS. 42A-42B illustrate, generally at 4200 and 4250 a Well Maintenance Tracking Record 4201 for the group of 35 wells, according to embodiments of the invention. With reference to FIG. 42A and FIG. 42B collectively, an output of the Well Analysis Engine (WAE) is illustrated. A column format is used to present data and analysis results for individual wells, where individual wells are arranged by row at 4242. The descriptions of the columns in 4201, provided directly below, are made with respect to a given well. Therefore, it is understood that reference to "a well" or "a given well" will not be made in order to maintain clarity in the description of the columns of 4201 that follows directly below.

A column at 4202 labeled "Well name" is used for well identification. A column at 4204 labeled "Zone diameter" indicates well screen diameter in inches. A column at 4206 labeled "Zone Interval (fbg)" indicates the depth to the top and the depth to the bottom of a well screen. A column at 4208 labeled "Permit Pumping Capacity (gpm)" indicates the maximum pumping capacity in gallons per minute (gpm) that is available under permit.

Clogging assessment spans the columns of 4210, 4212, 4214, 4216, 4218, 4220, 4222, 4224 and 4226. Aquifer chemistry includes a column at 4210 labeled "ORP" indicating oxidation reduction potential in millivolts (mV) and the column at 4212 labeled "pH" indicating potential of Hydrogen. The bacteria modality of clogging includes columns 4214, 4216, 4218, and 4220. A column at 4214 labeled "Fe Reducing" indicates activity level of Iron reducing bacteria. A column at 4216 labeled "Heterotrophic" indicates activity level for Aerobic Heterotrophic bacteria. A column at 4218 labeled "Slime" indicates activity level of Slime bacteria. A column at 4220 labeled "Sulfate reducing" indicates activity level for Sulfate reducing bacteria. A column at 4222 labeled "Particle Count decline (%)" indicates a reduction that requires at least two evaluations to calculate. A column at 4224 labeled "Height of Pumping Level over screen (ft)" indicates the height of the water cover over the screen at the current pumping rate. A column at 4226 labeled "Clogging Score" indicates an overall score for the three clogging modalities.

Yield and specific capacity span the columns of 4228, 4230, 4232, 4234, 4236, and 4238. A column at 4228 labeled "Aquifer Stability" refers to one of the Findings discussed previously above on the Well Yield Evaluation Worksheet (WYEW). A column at 4230 labeled "Production Rate (gpm)" indicates the current pumping rate. A column at 4232 labeled "Pumping Rate Change From Permitted Pumping Capacity" indicates either an increase or a decrease relative to the permitted pumping capacity shown in column 4208, units are gpm. A column at 4234 labeled "Additional Yield if Any (gpm)" indicates additional yield that is potentially available, this quantity is calculated using the current specific capacity and the Height of Pumping Level Over Screen column 4224. A column at 4236 labeled "SC Decline from Max (%)" indicates the percentage decline that the current specific capacity is at relative to the maximum specific capacity. This quantity requires at least two evaluations to compute decline. The maximum specific capacity is taken from available historical records. A column at 4238 labeled "SC rate of change (gpm/(yr*ft))" indicates the slope of the specific capacity time function which is illustrated above on a well yield record, such as for example 570 in FIG. 5 described above. Entries for column 4238 use the two most recent specific capacities recorded to calculate slope. Using the most recent specific capacity measurements enables the values listed in column 4238 to communicate the most recent performance.

An output of the Well Analysis Engine (WAE) is entered at a column 4240, which is labeled "Normalized score." This entry presents a normalized score which is also referred to as a normalized Well Performance Metric (WPM). Normalization and presentation of entries at 4240 can be done in different ways in different embodiments. For illustration of an example and with no limitation implied thereby the entries in 4240 have been normalized by the well with the largest value and then the group is scaled from zero (0) to 100. WELL 05, shown in 4242, is the well with the highest value, it has a normalized score of 100. The normalized score well performance metrics (WPMs) shown at 4240 are obtained using the clogging assessment and yield conditions in light of the PPC for each well.

Well Yield Classification Record

Figure 43B:
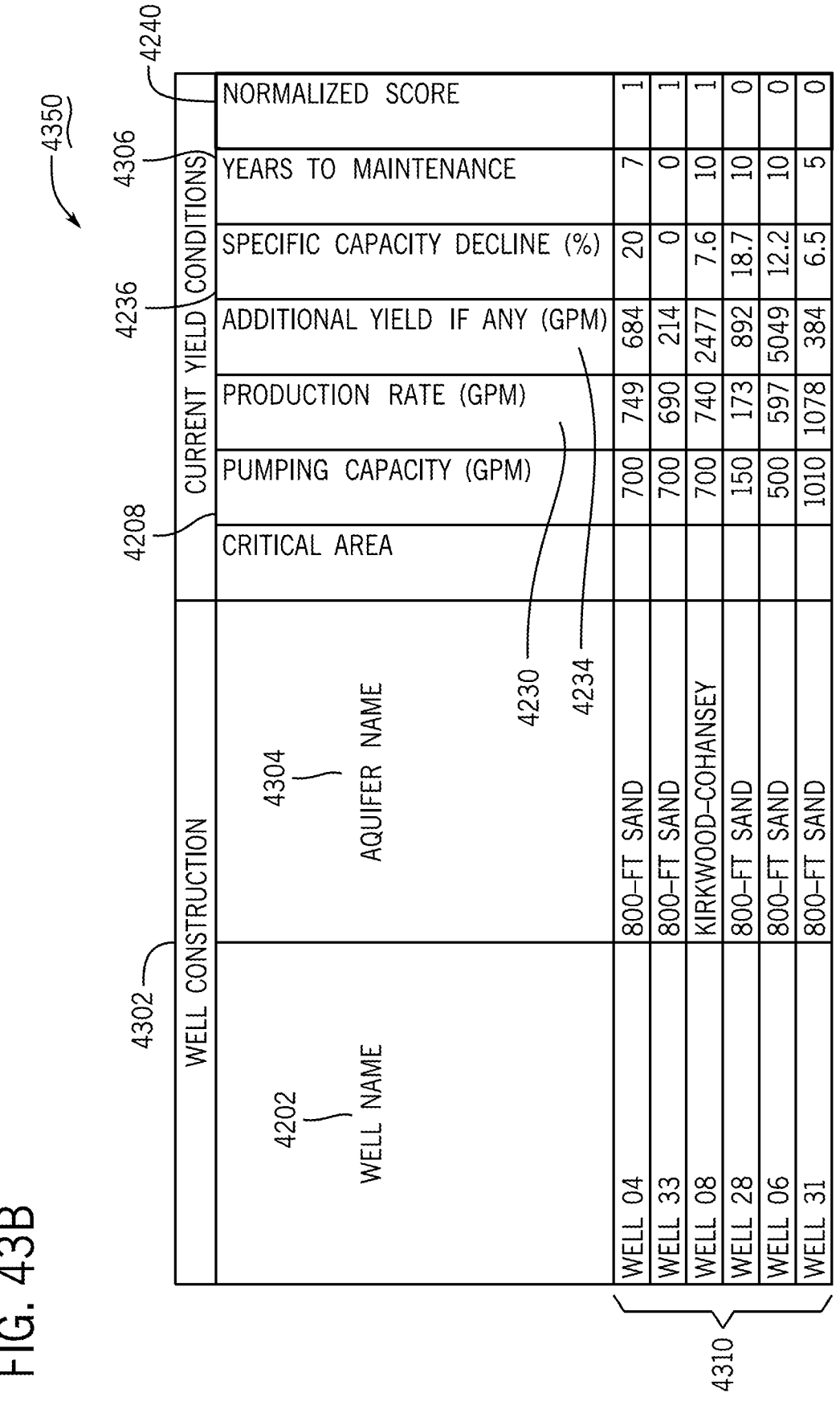

FIGS. 43A-43B illustrate, generally at 4300 and 4350, a Well Yield Classification Record for the group of 35 wells, according to embodiments of the invention. With reference to FIG. 43A and FIG. 43B collectively, the Well Yield Classification Record is another output of the Well Analysis Engine (WAE), illustrated at 4302. A column format is used to present data and analysis results for individual wells, where individual wells are arranged by row in 4302. A column at 4304 identifies an aquifer where a given well is located. A column at 4306 indicates an estimated time to maintenance of a given well, in years. Estimated time to maintenance is an output of the WAE, which is in various embodiments is based the on one or more inputs described above which include: aquifer status, specific capacity measurements, specific clogging information (SCI) and associated clogging modalities, well yield conditions, permitted pumping level, and other parameters such as settings for pumping rate, pump setting depth, etc. which could be modified to increase yield. The rows of 4302 have been divided into two sub-groups.

A first sub-group 4308 is sorted by row according to Normalized Score 4240 and is presented in descending order of normalized score 4240. With the highest normalized score 100 as the first row and the lowest normalized score 12 as the last row of the sub-group 4308. The sub-group 4308 includes those wells that have the potential to meet or exceed their permitted pumping capacity with modifications.

A second sub-group 4310 is sorted by row according to Normalized Score 4240 and is presented in descending order of normalized score 4240. With the highest normalized score 35 as the first row and the lowest normalized score zero (0) as the last row of the sub-group 4310. The sub-group 4310 includes those wells that currently meet their permitted pumping capacity. No action is necessary for the wells in the sub-group 4310.

Various other outputs from the WAE are possible. The outputs illustrated in FIG. 42A/FIG. 42B and FIG. 43A/FIG. 43B are given by way of example and do not limit embodiments of the invention.

Well Analysis Engine (WAE) Outputs

Figure 44:
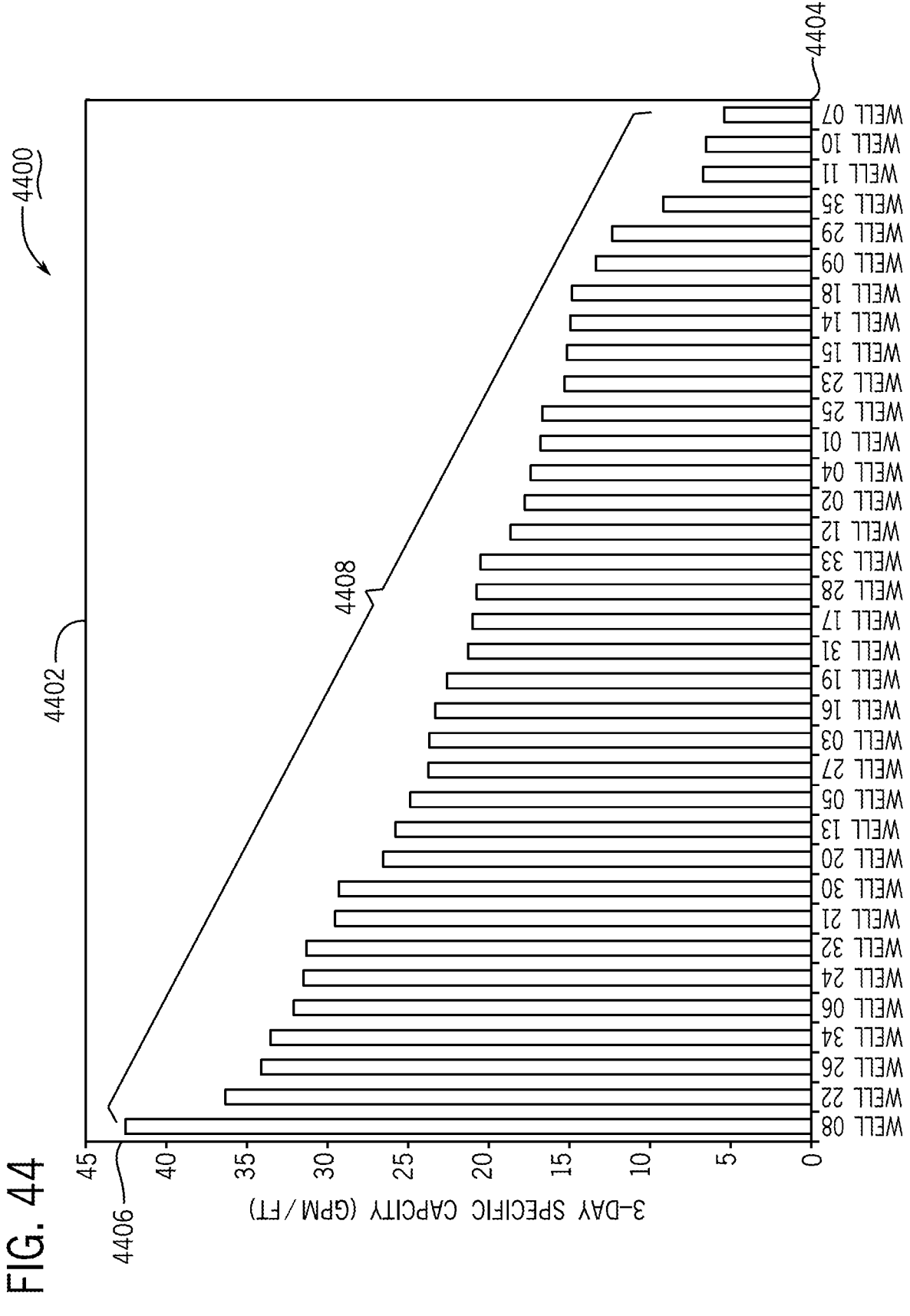
FIG. 44 illustrates 3-Day Specific Capacity Simulations for the group of 35 wells, according to embodiments of the invention.

FIG. 44 illustrates, generally at 4400, 3-Day Specific Capacity Simulations for the group of 35 wells, according to embodiments of the invention. With reference to FIG. 44, the bar chart at 4402 illustrates another WAE output for the group of 35 wells discussed above in conjunction with FIG. 42A/FIG. 42B and FIG. 43A/FIG. 43B. Wells are plotted along a horizontal axis at 4404. Specific capacity is plotted on a vertical axis at 4406. The results of 3-Day specific capacity simulations for the 35 wells are plotted as bars at 4408 in descending order from left to right along the horizontal axis 4404. Specific capacity is a measure of the productivity of a well. From the data 4408 the most productive wells are easily identified. The most productive well is WELL 08 and the least productive well is WELL 07.

Specific capacity data for a group of wells is useful for the task of improving efficiency for groundwater diversions within a well field. For example, in light of the information presented in FIG. 44, a groundwater well field manager has the information needed to lodge informed requests with a water regulating authority to request transfer of water from wells with low specific capacities and chronic maintenance issues to those wells with higher specific capacity and less maintenance issues. Specific capacity is considered in the process of assigning a well for redevelopment within the WAE. Thus, FIG. 44 is a helpful guide in support of maintenance considerations for management of the well field.

Figure 45:
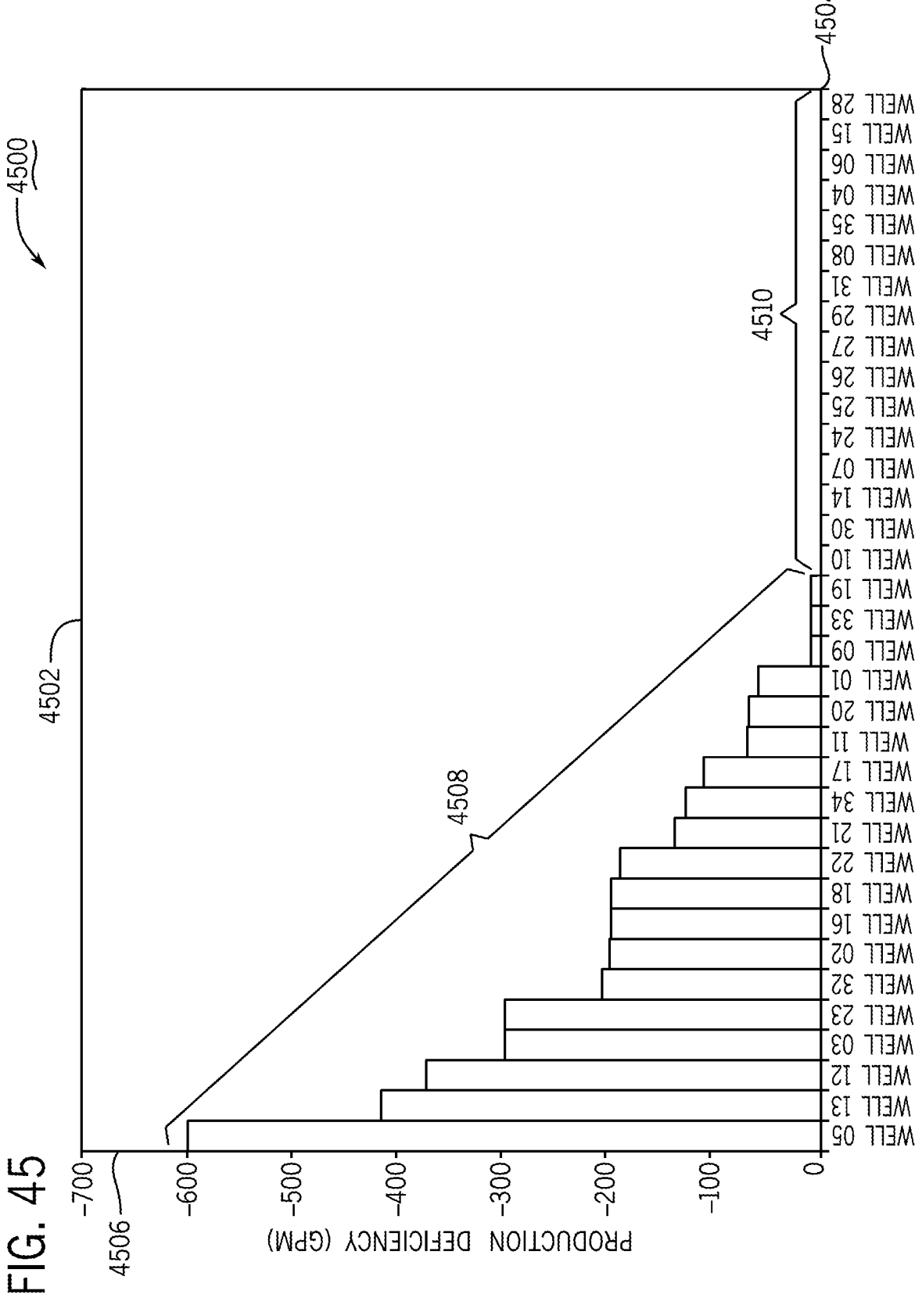
FIG. 45 illustrates Production Deficiency for the group of 35 wells, according to embodiments of the invention.

FIG. 45 illustrates, generally at 4500, Production Deficiency for the group of 35 wells, according to embodiments of the invention. With reference to FIG. 45, the bar chart at 4502 illustrates another WAE output for the group of 35 wells discussed above in conjunction with FIG. 42A/FIG. 42B and FIG. 43A/FIG. 43B. Wells in 4502 are plotted along a horizontal axis at 4504. Production deficiency (gpm) is plotted on a vertical axis at 4506 as bars in descending order from left to right along the horizontal axis 4504. The wells are divided into two sub-groups. A first sub-group 4508 contains those wells that are experiencing a production deficiency, hence the negative sign in front of the production deficiency number on the axis 4506. WELL 05 is experiencing the greatest production deficiency at –601 gpm. WELL 19, in sub-group 4508, is experiencing the least production deficiency at –10 gpm. The values for Production Deficiency plotted in 4502 are listed numerically in column 4232 FIG. 42A. A second sub-group 4510 contains those wells that are not experiencing production deficiency.

The WAE production deficiency output 4502 provides a concise focused graphical presentation of well field data that is useful to a well field manager. A well's present production deficiency as well as a well's growing deficiency in production over time represent valuable information to a well field manager. Information provided in FIG. 45 enables the well field manager to capture more ground water which can be used to meet system demand and/or to maximize profit by utilizing less expensive groundwater supply from non-problematic wells over that of other wells with more complex groundwater treatment needs. Thus, 4502 helps the well manager to maximize well yield and optimize dollars spent on a well field maintenance.

Figure 46:
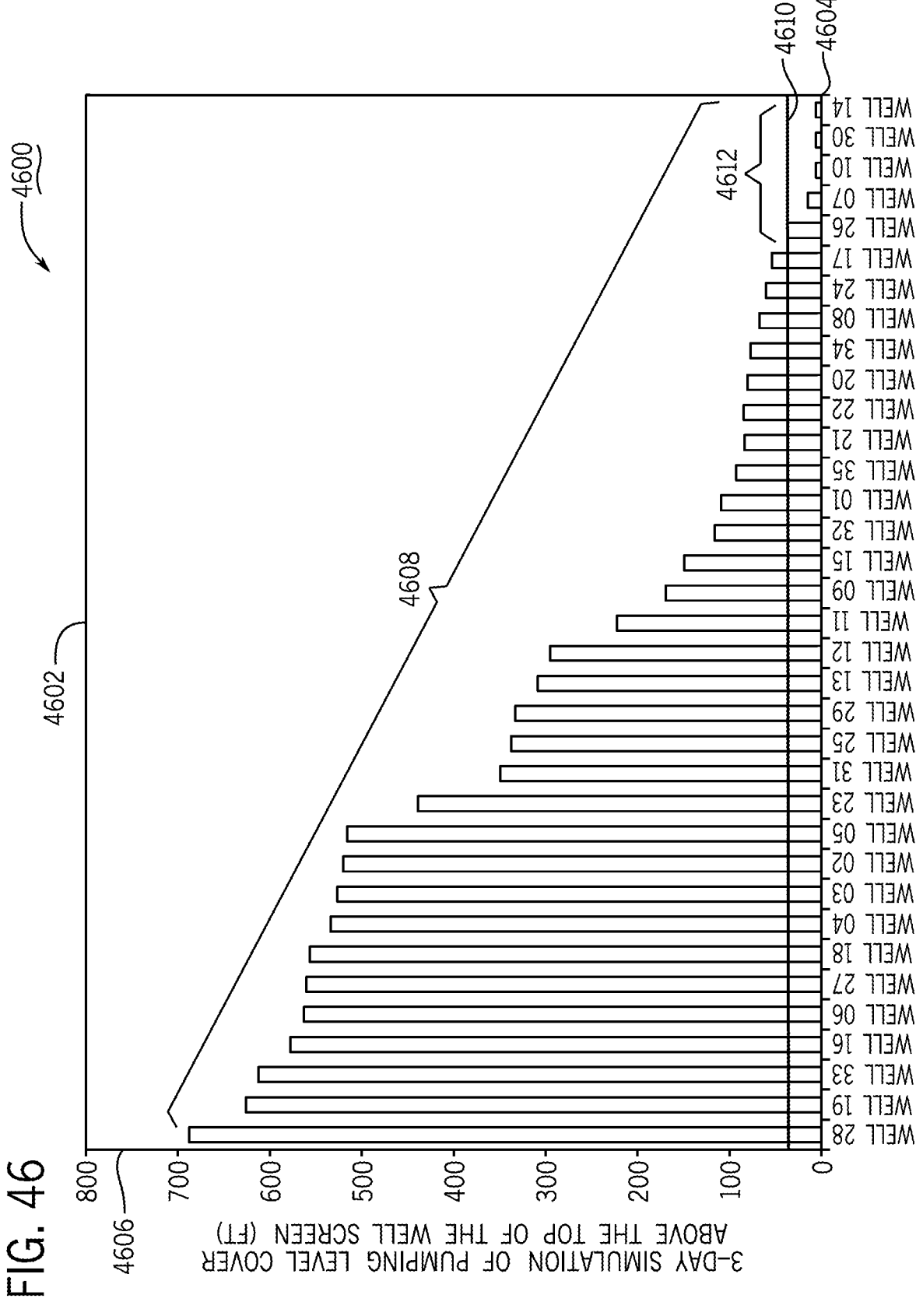
FIG. 46 illustrates water cover distances above the tops of the well screens from the 3-Day Specific Capacity Simulations for the group of 35 wells, according to embodiments of the invention.

FIG. 46 illustrates, generally at 4600, water cover distances above the tops of the well screens from the 3-Day Specific Capacity Simulations for the group of 35 wells, according to embodiments of the invention. With reference to FIG. 46, the bar chart at 4602 illustrates another WAE output for the group of 35 wells discussed above in conjunction with FIG. 42A/FIG. 42B and FIG. 43A/FIG. 43B. Wells in 4602 are plotted along a horizontal axis at 4604. Pumping level cover above a top of a well screen (ft) is plotted on a vertical axis at 4606 as bars in descending order from left to right along the horizontal axis 4604.

The well field picture provided at 4602 provides a well field manager with the ability to track water level cover above the top of the well screen in the system wells when the wells are pumping. Pumping levels near or at the top of the well screen promote well clogging through increases in mineral/metal oxide precipitation and bacterial growth as described above. These processes not only clog well screens, resulting in wells that require frequent redevelopment, but also clog pumps, piping, and filters, requiring more frequent cleaning and replacement.

Understanding where a pumping level stabilizes relative to a top of a well screen is critical to sustainable well operation. Such knowledge enables a well field manager to provide adequate water cover to a well, thereby ensuring that the well provides as much water as is possible with the least maintenance. As discussed above, water level cover of less than 30 feet generates problematic oxidizing conditions in the aquifer just outside the well screen. A reference line 4610 indicates a 30 foot cover limit above the well screen for reference. A sub-group of wells indicated at 4612 have water cover less than the reference line 4610. The wells in 4612 require modifications to prevent reductions in yield that are likely in view of their low cover.

Figure 47:
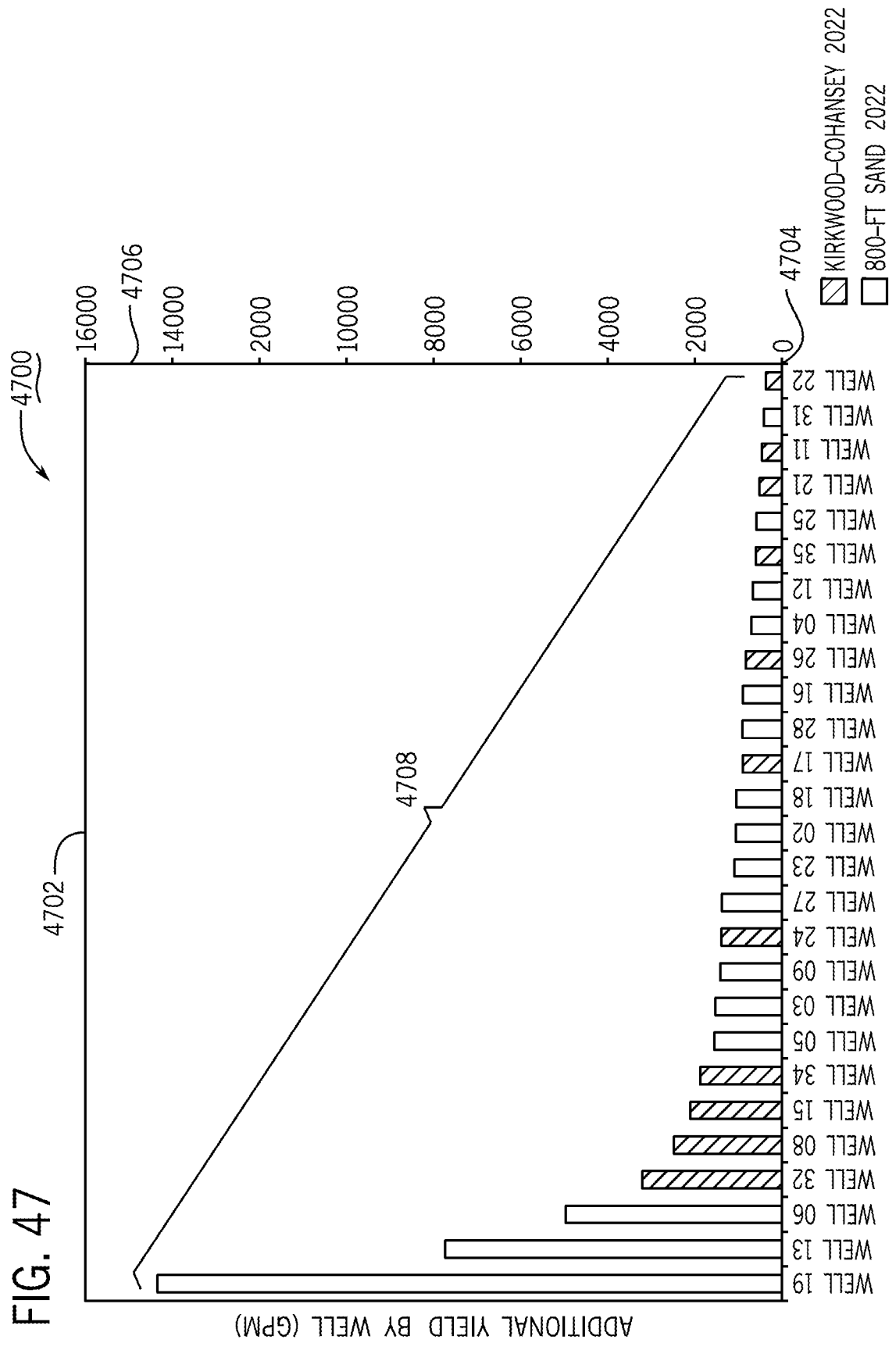
FIG. 47 illustrates additional yield by well for the group of 35 wells, according to embodiments of the invention.

FIG. 47 illustrates, generally at 4700, additional yield by well for the group of 35 wells, according to embodiments of the invention. With reference to FIG. 47, the bar chart at 4702 illustrates another WAE output for the group of 35 wells discussed above in conjunction with FIG. 42A/FIG. 42B and FIG. 43A/FIG. 43B. Wells in 4702 are plotted along a horizontal axis at 4704. Additional yield (gpm) is plotted on a vertical axis at 4706 as bars in descending order from left to right along the horizontal axis 4704. WELL 19 has the largest additional yield at 14,387 gpm. Numerical values of additional yield are also listed in column 4234 in FIG. 43A. WELL 22 has the smallest additional yield at 331 gpm. Out of the 35 well group, a sub-group of 27 wells have the potential for additional yield and are included in the chart at 4702. The wells in the 35 well group that do not have potential for additional yield are not listed in 4702. The aquifer that each well, in the 27 well sub-group, is located in is identified in FIG. 47.

In various embodiments, the WAE can be applied to diversion of groundwater to mitigate shortages caused by contamination of one or more wells. For example, per- and polyfluoroalkyl substances-known as PFAS contaminate occurs in some wells rendering the water unfit for human consumption. The diversion process would proceed as follows. First a review of well locations (not shown) experiencing PFAS or other contamination is conducted. Secondly, the wells in a well field with potential additional yield, such as hypothetically those wells shown in FIG. 7A, are identified. Thirdly, the wells with the potential for increased production enable a well field manager to select certain wells for increased production while taking off-line the wells experiencing contamination. Information similar to that contained in FIG. 7A can be used in conjunction with information on locations of contaminated wells within a group of wells in order to produce a plan for diversion of water thereby eliminating the contaminated wells from the group while supplementing the now off-line wells with additional yield from those so identified.

Figure 48:
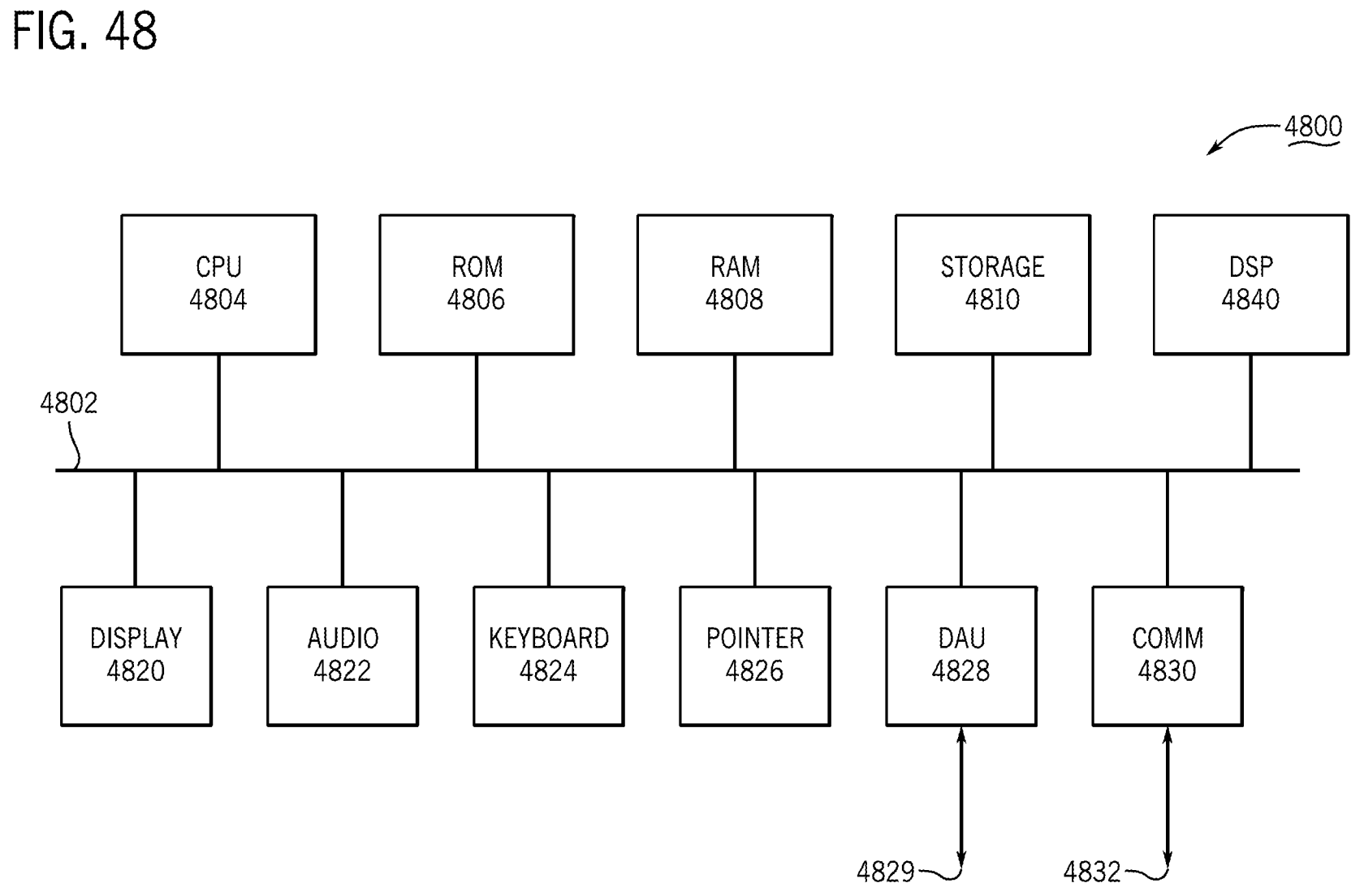

FIG. 48 illustrates, generally at 4800, an automated system in which embodiments of the invention may be used. The block diagram is a high-level conceptual representation and may be implemented in a variety of ways and by various architectures. With reference to FIG. 48, bus system 4802 interconnects a Central Processing Unit (CPU) 4804, Read Only Memory (ROM) 4806, Random Access Memory (RAM) 4808, storage 4810, display 4820, audio 4822, keyboard 4824, pointer 4826, data acquisition unit (DAU) 4828, and communications 4830. The bus system 4802 may be for example, one or more of such buses as a system bus, Peripheral Component Interconnect (PCI), Advanced Graphics Port (AGP), Small Computer System Interface (SCSI), Institute of Electrical and Electronics Engineers (IEEE) standard number 1394 (FireWire), Universal Serial Bus (USB), or a dedicated bus designed for a custom application, etc. The CPU 4804 may be a single, multiple, or even a distributed computing resource or a digital signal processing (DSP) chip. Storage 4810 may be Compact Disc (CD), Digital Versatile Disk (DVD), hard disks (HD), optical disks, tape, flash, memory sticks, video recorders, etc. In various embodiments, the system 4800 is configured and used to collect data from one or more wells as described above. In various embodiments, the system 4800 is configured to process and analyze data providing the Well Analysis Engine (WAE) described above. Note that depending upon the actual implementation of the system, the system may include some, all, more, or a rearrangement of components in the block diagram. In some embodiments, aspects of the system 4800 are performed in software. While in some embodiments, aspects of the system 4800 are performed in dedicated hardware such as a digital signal processing (DSP) chip 4840, or a system on a chip (SOC) which can also be represented at 4840, etc. as well as combinations of dedicated hardware and software as is known and appreciated by those of ordinary skill in the art.

Thus, in various embodiments, data is received at 4829 for processing by the system 4800. In some embodiments, data is received at 4829 from one or more components of the system illustrated in 700 (FIG. 7A), such as but not limited to, the particle counter 710, the bacteria analysis 734, the aquifer chemistry module 744, etc. Such data can be transmitted at 4832 via communications interface 4830 for further processing in a remote location. Connection with a network, such as an intranet or the Internet is obtained via 4832, as is recognized by those of skill in the art, which enables the system 4800 to communicate with other data processing devices or systems in remote locations. Following processing or analyzing the data in the remote location instructions can be sent back to a system to adjust parameters associated with the system that is controlling one or more wells.

For example, embodiments of the invention can be implemented on a computer system 4800 configured as a desktop computer or workstation, on for example a WINDOWS® compatible computer running operating systems such as WINDOWS® XP Home or WINDOWS® XP Professional, WINDOWS® 10 Home or WINDOWS® 10 Professional, WINDOWS® 11 Home or WINDOWS® 11 Professional, Linux, Unix, etc. as well as computers from APPLE COMPUTER, Inc. running operating systems such as OS X, etc. Alternatively, or in conjunction with such an implementation, embodiments of the invention can be configured with devices such as speakers, earphones, video monitors, etc. configured for use with a Bluetooth communication channel.

In yet other implementations, embodiments of the invention are configured to be implemented by mobile devices such as a smart phone, a tablet computer, or the like.

In various embodiments, the components of systems described in the previous figures are implemented in an integrated circuit device, which may include an integrated circuit package containing the integrated circuit. In some embodiments, the components of systems as well as the systems are implemented in a single integrated circuit die. In other embodiments, the components of systems as well as the systems are implemented in more than one integrated circuit die of an integrated circuit device which may include a multi-chip package containing the integrated circuit.

Thus, in various embodiments, as described above, a well analysis framework has been taught. The well analysis framework is applicable to individual wells or to a group of individual wells analyzed collectively. The well analysis framework utilizes: (1) the specific capacity measurements and estimates thereof based on simulations of depth to water using extrapolated pumping times to create well yield records as a function of time for a given well (embodiments of which are described above); (2) time gating of water sample collection from a well utilizing a particle counter to support multi-modal clogging analysis and well chemistry analysis (embodiments of which are described above); (3) compilation of water level records over time for an aquifer the well resides in; and (4) analysis of the foregoing to provide findings and recommendations for future operation of the well. The findings and recommendations are directed to maintaining well yield by addressing the individual component causes that are causing well yield to decrease. The analysis framework includes capturing and presentation of well data that is used to assess, establish, and address the causes of loss of yield that are occurring in a given well or in a group of wells. These causes include the causative modalities of well clogging as well as changes in the aquifer. Over a period of time, a baseline of well data is acquired, through tests that are repeated for a given well or wells. The data are analyzed, and the well analysis framework identifies wells in need of either treatment, redevelopment, or replacement due to declining yield. The analysis framework ranks a well according to the most expedient time frame for maintenance (such as treatment, mechanical alterations, operational alternations, redevelopment and/or replacement) with the goal of achieving long-term sustainable yields. The analysis framework facilitates quantifiable budget projections for well field operation and enables operational efficiency of a well field to be optimized.

For purposes of discussing and understanding the embodiments of the invention, it is to be understood that various terms are used by those knowledgeable in the art to describe techniques and approaches. Furthermore, in the description, for purposes of explanation, numerous specific details are set forth in order to provide a thorough understanding of the present invention. It will be evident, however, to one of ordinary skill in the art that the present invention may be practiced without these specific details. In some instances, well-known structures and devices are shown in block diagram form, rather than in detail, in order to avoid obscuring the present invention. These embodiments are described in sufficient detail to enable those of ordinary skill in the art to practice the invention, and it is to be understood that other embodiments may be utilized, and that logical, mechanical, electrical, and other changes may be made without departing from the scope of the present invention.

Some portions of the description may be presented in terms of algorithms and symbolic representations of operations on, for example, data bits within a computer memory. These algorithmic descriptions and representations are the means used by those of ordinary skill in the data processing arts to most effectively convey the substance of their work to others of ordinary skill in the art. An algorithm is here, and generally, conceived to be a self-consistent sequence of acts leading to a desired result. The acts are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, waveforms, data, time series or the like.

It should be borne in mind, however, that these and similar terms are to be associated with the appropriate physical quantities and are merely convenient labels applied to these quantities. Unless specifically stated otherwise as apparent from the discussion, it is appreciated that throughout the description, discussions utilizing terms such as "processing" or "computing" or "calculating" or "determining" or "displaying" or the like" can refer to action and processes of computer system or similar electronic computing device, that manipulates and transforms data represented as physical (electronic) quantities within the computer system's registers and memories into other data similarly represented as physical quantities within the computer system memories or registers or other such information storage, transmission, or display devices.

An apparatus for performing the operations herein can implement the present invention. This apparatus may be specially constructed for the required purposes, or it may comprise a general-purpose computer, selectively activated or reconfigured by a computer program stored in the computer. Such a computer program may be stored in a computer readable storage medium, such as, but not limited to, any type of disk including floppy disks, hard disks, optical disks, compact disk read-only memories (CD-ROMs), and magnetic-optical disks, read-only memories (ROMs), random access memories (RAMs), electrically programmable read-only memories (EPROM) s, electrically erasable programmable read-only memories (EEPROMs), FLASH memories, magnetic or optical cards, etc., or any type of media suitable for storing electronic instructions either local to the computer or remote to the computer.

The algorithms and displays presented herein are not inherently related to any particular computer or other apparatus. Various general-purpose systems may be used with programs in accordance with the teachings herein, or it may prove convenient to construct more specialized apparatus to perform the required method. For example, any of the methods according to the present invention can be implemented in hard-wired circuitry, by programming a general-purpose processor, or by any combination of hardware and software. One of ordinary skill in the art will immediately appreciate that the invention can be practiced with computer system configurations other than those described, including hand-held devices, multiprocessor systems, microprocessor-based or programmable consumer electronics, digital signal processing (DSP) devices, network PCs, minicomputers, mainframe computers, and the like. Embodiments of the invention can also be practiced in distributed computing environments where tasks are performed by remote processing devices that are linked through a communications network. In other examples, embodiments of the invention as described in the figures above can be implemented using a system on a chip (SOC), a digital signal processing (DSP) chip, or in other implementations of hardware and software.

The methods of the invention may be implemented using computer software. If written in a programming language conforming to a recognized standard, sequences of instructions designed to implement the methods can be compiled for execution on a variety of hardware platforms and for interface to a variety of operating systems. In addition, the present invention is not described with reference to any particular programming language. It will be appreciated that a variety of programming languages may be used to implement the teachings of the invention as described herein. Furthermore, it is common in the art to speak of software, in one form or another (e.g., program, procedure, application, driver, . . . ), as taking an action or causing a result. Such expressions are merely a shorthand way of saying that execution of the software by a computer causes the processor of the computer to perform an action or produce a result.

It is to be understood that various terms and techniques are used by those knowledgeable in the art to describe communications, protocols, applications, implementations, mechanisms, etc. One such technique is the description of an implementation of a technique in terms of an algorithm or mathematical expression. That is, while the technique may be, for example, implemented as executing code on a computer, the expression of that technique may be more aptly and succinctly conveyed and communicated as a formula, algorithm, mathematical expression, flow diagram or flow chart. Thus, one of ordinary skill in the art would recognize a block denoting A+B=C as an additive function whose implementation in hardware and/or software would take two inputs (A and B) and produce a summation output (C). Thus, the use of formula, algorithm, or mathematical expression as descriptions is to be understood as having a physical embodiment in at least hardware and/or software (such as a computer system in which the techniques of the present invention may be practiced as well as implemented as an embodiment).

Non-transitory machine-readable media is understood to include any mechanism for storing information in a form readable by a machine (e.g., a computer). For example, a machine-readable medium, synonymously referred to as a computer-readable medium, includes read only memory (ROM); random access memory (RAM); magnetic disk storage media; optical storage media; flash memory devices; except electrical, optical, acoustical or other forms of transmitting information via propagated signals (e.g., carrier waves, infrared signals, digital signals, etc.); etc.

As used in this description, "one embodiment" or "an embodiment" or similar phrases means that the feature(s) being described are included in at least one embodiment of the invention. References to "one embodiment" in this description do not necessarily refer to the same embodiment; however, neither are such embodiments mutually exclusive. Nor does "one embodiment" imply that there is but a single embodiment of the invention. For example, a feature, structure, act, etc. described in "one embodiment" may also be included in other embodiments. Thus, the invention may include a variety of combinations and/or integrations of the embodiments described herein.

While the invention has been described in terms of several embodiments, those of skill in the art will recognize that the invention is not limited to the embodiments described, but can be practiced with modification and alteration within the spirit and scope of the appended claims. The description is thus to be regarded as illustrative instead of limiting.

What is claimed is:

1. A system to determine precipitation of a first mineral or metal out of solution in a first water well, comprising:
   a well water analysis device, the well water analysis device further comprising:
      an aquifer chemistry module, the aquifer chemistry module to produce a measurement of oxidation reduction potential of a water sample from the first water well, wherein the water sample is taken from the first water well while water is produced from the first water well, the first water well having a well screen installed therein; and a measurement of pH of water taken from the first water well;
      an Eh-pH phase diagram for the first mineral or metal;
      a data processing system configured to accept the measurement of oxidation reduction potential and the measurement of pH; and
   a non-transient computer readable medium containing executable computer program instructions which, when executed by the data processing system, cause the data processing system to perform steps comprising:
      comparing the measurement of oxidation reduction potential and the measurement of pH with one or both of:
         (a) a precipitation zone on the Eh-pH phase diagram for the first mineral or metal; and
         (b) a border of a precipitation zone on the Eh-pH phase diagram; and
         determining the first mineral or metal is precipitating out of solution, the determining is based on the comparing, in response to the determining the system is configured to be reconfigured with the addition of a custom extended pump sleeve, the custom extended pump sleeve having a first end and a second end, the first end is attached to a well pump above a water inlet for the well pump, the second end extends down below a motor configured with the well pump.

2. The system of claim 1, the data processing system to perform steps further comprising:
   providing a prediction on need for redevelopment of the first water well, wherein the providing uses the determining.

3. The system of claim 1, wherein the first mineral or metal is selected from the group consisting of Iron, Manganese, Calcium Carbonate, Sulphate and a user specified mineral or metal.

4. The system of claim 1, where the second end extends down to a depth of the well screen.

5. The system of claim 1, wherein the second end extends down to approximately a bottom region of the well screen.

6. The system of claim 1, the data processing system to perform steps further comprising:
   establishing a well performance metric value for the first water well, wherein the well performance metric value is based on the determining.

7. The system of claim 1, the data processing system to perform steps further comprising:
   establishing a well performance metric value for each water well in a group of water wells to create a plurality of well performance metric values, wherein a well performance metric value for a given water well in the group is based on determining the first mineral or metal is precipitating out of solution, using the steps of claim 1 applied to the given water well.

8. The system of claim 1, the data processing system to perform steps further comprising:
   determining a second mineral or metal in each water well of the group of water wells is precipitating out of solution is accomplished using the steps of claim 1; and
   establishing a well performance metric for each water well in the group of water wells to create a plurality of well performance metric values, wherein a well performance metric value for a given water well in the group is based on determining the second mineral or metal is precipitating out of solution in the given water well.

9. The system of claim 1, the data processing system to perform steps further comprising:
   determining M different minerals or metals are precipitating out of solution in each water well of a group of N water wells using the steps of claim 1; and
   establishing a well performance metric value for each water well in the group, wherein a well performance metric value for a given water well in the group is based on determining the M different minerals or metals are precipitating out of solution.

10. A system to determine precipitation of a first mineral or metal out of solution in a first water well, comprising:
   a well water analysis device, the well water analysis device further comprising:
      an aquifer chemistry module, the aquifer chemistry module to produce a measurement of oxidation reduction potential of a water sample from the first water well, wherein the water sample is taken from the first water well while water is produced from the first water well, the first water well having a well screen installed therein; and a measurement of pH of water taken from the first water well;
      an Eh-pH phase diagram for the first mineral or metal;
      a data processing system configured to accept the measurement of oxidation reduction potential and the measurement of pH; and
   a non-transient computer readable medium containing executable computer program instructions which, when executed by the data processing system, cause the data processing system to perform steps comprising:
      comparing the measurement of oxidation reduction potential and the measurement of pH with one or both of:
         (a) a precipitation zone on the Eh-pH phase diagram for the first mineral or metal; and
         (b) a border of a precipitation zone on the Eh-pH phase diagram; and
         determining the first mineral or metal is precipitating out of solution, the determining is based on the comparing, in response to the determining a frequency of dewatering the first water well is adjusted.

11. The system of claim 10, the data processing system to perform steps further comprising:
   establishing a well performance metric value for the first water well, wherein the well performance metric value is based on determining the first mineral or metal is precipitating out of solution.

12. The system of claim 10, the data processing system to perform steps further comprising:
   establishing a well performance metric value for each water well in a group of water wells to create a plurality of well performance metric values, wherein a well performance metric value for a given water well in the group is based on determining the first mineral or metal is precipitating out of solution, using the steps of claim 10 applied to the given water well.

13. The system of claim 10, the data processing system to perform steps further comprising:

determining a second mineral or metal in each water well of the group of water wells is precipitating out of solution is accomplished using the steps of claim 10; and establishing a well performance metric for each water well in the group of water wells to create a plurality of well performance metric values, wherein a well performance metric value for a given water well in the group is based on determining the second mineral or metal is precipitating out of solution in the given water well.

14. The system of claim 10, the data processing system to perform steps further comprising:

determining M different minerals or metals are precipitating out of solution in each water well of a group of N water wells using the steps of claim 10; and establishing a well performance metric value for each water well in the group, wherein a well performance metric value for a given water well in the group is based on determining the M different minerals or metals are precipitating out of solution.

15. The system of claim 10, the data processing system to perform steps further comprising:

providing a prediction on need for redevelopment of the first water well, wherein the providing uses the determining.

16. The system of claim 10, wherein the first mineral or metal is selected from the group consisting of Iron, Manganese, Calcium Carbonate, Sulphate and a user specified mineral or metal.

17. A system to determine precipitation of a first mineral or metal out of solution in a first water well, comprising:

a well water analysis device, the well water analysis device further comprising:

an aquifer chemistry module, the aquifer chemistry module to produce a measurement of oxidation reduction potential of a water sample from the first water well, wherein the water sample is taken from the first water well while water is produced from the first water well, the first water well having a well screen installed therein; and a measurement of pH of water taken from the first water well;

an Eh-pH phase diagram for the first mineral or metal;

a data processing system configured to accept the measurement of oxidation reduction potential and the measurement of pH; and a non-transient computer readable medium containing executable computer program instructions which, when executed by the data processing system, cause the data processing system to perform steps comprising:

comparing the measurement of oxidation reduction potential and the measurement of pH with one or both of:

(a) a precipitation zone on the Eh-pH phase diagram for the first mineral or metal; and (b) a border of a precipitation zone on the Eh-pH phase diagram; and determining the first mineral or metal is precipitating out of solution, the determining is based on the comparing, in response to the determining, the system is configured to be reconfigured for a treatment with an acid mixture, wherein the first water well is placed in an OFF state, then the acid mixture is surged in the well screen, then the first water well remains in the OFF state with the addition of the acid mixture for a first period of time, after passage of the first period of time the first water well is pumped off to remove the acid mixture.

18. The system of claim 17, wherein a tremie is used during the treatment.

19. The system of claim 17, wherein a pH of the acid mixture is 2.0 or less.

20. The system of claim 17, wherein an acid used in the acid mixture is selected from the group consisting of hydrochloric, sulfuric, sulfamic, muriatic, and a user specified acid.

21. The system of claim 17, wherein the first period of time is sufficient to dissolve some or all of the first mineral or metal from the well screen.

22. The system of claim 21, wherein the first period of time is approximately twelve hours.

23. The system of claim 21, wherein the acid mixture is to be surged for approximately four to six hours.

24. The system of claim 17, the data processing system to perform steps further comprising:

producing an estimate of specific capacity for the first water well, wherein the producing occurs after the pumping off;

comparing the estimate with a previous estimate of specific capacity made before the steps of claim 17 were applied to the first water well; and repeating the steps of claim 17 if the estimate is less than the previous estimate.

25. The system of claim 17, the data processing system to perform steps further comprising:

establishing a well performance metric value for the first water well, wherein the well performance metric value is based on determining the first mineral or metal is precipitating out of solution.

26. The system of claim 17, the data processing system to perform steps further comprising:

establishing a well performance metric value for each water well in a group of water wells to create a plurality of well performance metric values, wherein a well performance metric value for a given water well in the group is based on determining the first mineral or metal is precipitating out of solution, using the steps of claim 10 applied to the given water well.

27. The system of claim 17, the data processing system to perform steps further comprising:

determining a second mineral or metal in each water well of the group of water wells is precipitating out of solution is accomplished using the steps of claim 10; and establishing a well performance metric for each water well in the group of water wells to create a plurality of well performance metric values, wherein a well performance metric value for a given water well in the group is based on determining the second mineral or metal is precipitating out of solution in the given water well.

28. The system of claim 17, the data processing system to perform steps further comprising:

determining M different minerals or metals are precipitating out of solution in each water well of a group of N water wells using the steps of claim 10; and establishing a well performance metric value for each water well in the group, wherein a well performance metric value for a given water well in the group is based on determining the M different minerals or metals are precipitating out of solution.

29. The system of claim 17, the data processing system to perform steps further comprising:

providing a prediction on need for redevelopment of the first water well, wherein the providing uses the determining.

30. The system of claim 17, wherein the first mineral or metal is selected from the group consisting of Iron, Manganese, Calcium Carbonate, Sulphate and a user specified mineral or metal.

31. A method to determine a first mineral or metal is precipitating out of solution in a first water well, the first water well having a well screen or an open borehole in bedrock comprising:

receiving a water sample from the first water well the water sample is taken from the first water well while water is produced from the first water well;

making a first oxidation reduction potential measurement on the water sample;

performing a first pH measurement on the water sample;

comparing the first oxidation reduction potential measurement and the first pH measurement with one or both of:

(a) a precipitation zone on an Eh-pH phase diagram for the first mineral or metal; and (b) a border of a precipitation zone on the Eh-pH phase diagram; and determining the first mineral or metal is precipitating out of solution, the determining is based on the comparing, in response to the determining, the method further comprising:

deepening a water intake location for the first water well using a custom extended pump sleeve.

32. The method of claim 31, further comprising:

providing a prediction on the need for redevelopment of the first water well, wherein the providing is based on the determining.

33. The method of claim 31, wherein the first mineral or metal is selected from the group consisting of Iron, Manganese, Calcium Carbonate, Sulphate and a user specified mineral or metal.

34. The method of claim 33, wherein an aquifer chemistry module is used for the making and the performing.

35. The method of claim 31, where the custom extended pump sleeve extends down to a depth of the well screen or the open borehole.

36. The method of claim 35, wherein the custom extended pump sleeve extends down to approximately a bottom region of the well screen or the open borehole.

37. The method of claim 31, further comprising:

establishing a well performance metric value for the first water well, wherein the well performance metric value is based on the determining.

38. The method of claim 31, further comprising:

establishing a well performance metric for each water well in a group of water wells to create a plurality of well performance metric values, wherein a well performance metric value for a given water well in the group is based on determining the first mineral or metal is precipitating out of solution in the given water well, using the steps of claim 31 applied to the given water well.

39. The method of claim 31, further comprising:

determining a second mineral or metal in each water well of a group of water wells is precipitating out of solution using the steps of claim 31; and establishing a well performance metric value for each water well in the group of water wells to create a plurality of well performance metric values, wherein a well performance metric value for a given water well in the group is based on determining the second mineral or metal is precipitating out of solution in the given water well.

40. The method of claim 31, further comprising:

determining M different minerals or metals are precipitating out of solution in each water well of a group of N water wells using the steps of claim 31; and establishing a well performance metric value for each water well in the group, wherein a well performance metric value for a given water well in the group is based on determining the M different minerals or metals are precipitating out of solution.

41. A method to determine a first mineral or metal is precipitating out of solution in a first water well, the first water well having a well screen or an open borehole in bedrock, comprising:

receiving a water sample from the first water well the water sample is taken from the first water well while water is produced from the first water well;

making a first oxidation reduction potential measurement on the water sample;

performing a first pH measurement on the water sample;

comparing the first oxidation reduction potential measurement and the first pH measurement with one or both of:

(a) a precipitation zone on an Eh-pH phase diagram for the first mineral or metal; and (b) a border of a precipitation zone on the Eh-pH phase diagram; and determining the first mineral or metal is precipitating out of solution, the determining is based on the comparing, the method further comprising:

reducing a frequency of dewatering for the first water well.

42. The method of claim 41, further comprising:

providing a prediction on the need for redevelopment of the first water well, wherein the providing is based on the determining.

43. The method of claim 41, wherein the first mineral or metal is selected from the group consisting of Iron, Manganese, Calcium Carbonate, Sulphate and a user specified mineral or metal.

44. The method of claim 43, wherein an aquifer chemistry module is used for the making and the performing.

45. The method of claim 41, further comprising:

establishing a well performance metric value for the first water well, wherein the well performance metric value is based on determining the first mineral or metal is precipitating out of solution.

46. The method of claim 41, further comprising:

establishing a well performance metric for each water well in a group of water wells to create a plurality of well performance metric values, wherein a well performance metric value for a given water well in the group is based on determining the first mineral or metal is precipitating out of solution in the given water well, and determining the first mineral or metal is precipitating out of solution in the given water well using the steps of claim 41 applied to the given water well.

47. The method of claim 41, further comprising:

determining a second mineral or metal in each water well of a group of water wells is precipitating out of solution using the steps of claim 41; and establishing a well performance metric value for each water well in the group of water wells to create a plurality of well performance metric values, wherein a well performance metric value for a given water well in the group is based on determining the second mineral or metal is precipitating out of solution in the given water well.

48. The method of claim 41, further comprising:

determining M different minerals or metals are precipitating out of solution in each water well of a group of N water wells using the steps of claim 41; and establishing a well performance metric value for each water well in the group, wherein a well performance metric value for a given water well in the group is based on determining the M different minerals or metals are precipitating out of solution.

49. A method to determine a first mineral or metal is precipitating out of solution in a first water well, the first water well having a well screen or an open borehole in bedrock, comprising:

receiving a water sample from the first water well the water sample is taken from the first water well while water is produced from the first water well;

making a first oxidation reduction potential measurement on the water sample;

performing a first pH measurement on the water sample;

comparing the first oxidation reduction potential measurement and the first pH measurement with one or both of:

(a) a precipitation zone on an Eh-pH phase diagram for the first mineral or metal; and (b) a border of a precipitation zone on the Eh-pH phase diagram; and determining the first mineral or metal is precipitating out of solution, the determining is based on the comparing, in response to the determining, the method further comprising:

dissolving at least one mineral or metal from the well screen installed in the first water well, in sequential order the dissolving further comprising:

adding an acid mixture to the first water well when the first water well is in an OFF state;

surging the acid mixture into the well screen;

waiting a first period time; and pumping off the first water well to remove the acid mixture.

50. The method of claim 49, wherein a tremie is used during the adding.

51. The method of claim 49, wherein a pH of the acid mixture is 2.0 or less.

52. The method of claim 49, wherein an acid used in the acid mixture is selected from the group consisting of hydrochloric, sulfuric, sulfamic, malonic, and a user specified acid.

53. The method of claim 49, wherein the first period of time is sufficient to dissolve some or all of the first mineral or metal from the well screen.

54. The method of claim 53, wherein the first period of time is at least twelve hours.

55. The method of claim 53, wherein the surging continues for approximately four to six hours.

56. The method of claim 49, the method further comprising:

producing an estimate of specific capacity for the first water well, wherein the producing occurs after the pumping off;

comparing the estimate with a target estimate of specific capacity made before the method of claim 51 was applied to the first water well; and repeating the method of claim 51 if the estimate is less than the target estimate.

57. The method of claim 49, further comprising:

providing a prediction on the need for redevelopment of the first water well, wherein the providing is based on the determining.

58. The method of claim 49, wherein the first mineral or metal is selected from the group consisting of Iron, Manganese, Calcium Carbonate, Sulphate and a user specified mineral or metal.

59. The method of claim 58, wherein an aquifer chemistry module is used for the making and the performing.

60. The method of claim 49, further comprising:

establishing a well performance metric value for the first water well, wherein the well performance metric value is based on determining the first mineral or metal is precipitating out of solution.

61. The method of claim 49, further comprising:

establishing a well performance metric for each water well in a group of water wells to create a plurality of well performance metric values, wherein a well performance metric value for a given water well in the group is based on determining the first mineral or metal is precipitating out of solution in the given water well, using the steps of claim 49 applied to the given water well.

62. The method of claim 49, further comprising:

determining a second mineral or metal in each water well of a group of water wells is precipitating out of solution using the steps of claim 49; and establishing a well performance metric value for each water well in the group of water wells to create a plurality of well performance metric values, wherein a well performance metric value for a given water well in the group is based on determining the second mineral or metal is precipitating out of solution in the given water well.

63. The method of claim 49, further comprising:

determining M different minerals or metals are precipitating out of solution in each water well of a group of N water wells using the steps of claim 49; and establishing a well performance metric value for each water well in the group, wherein a well performance metric value for a given water well in the group is based on determining the M different minerals or metals are precipitating out of solution.

\* \* \* \* \*